United States Patent
Cobb et al.

(10) Patent No.: US 10,906,932 B2
(45) Date of Patent: Feb. 2, 2021

(54) CYCLISING PEPTIDES

(71) Applicant: The University of Durham, Durham (GB)

(72) Inventors: Steven Cobb, Durham (GB); Christopher Coxon, Durham (GB); Graham Sandford, Durham (GB)

(73) Assignee: The University of Durham, Durham (GB)

( * ) Notice: Subject to any disclaimer, the term of this patent is extended or adjusted under 35 U.S.C. 154(b) by 181 days.

(21) Appl. No.: 15/312,562

(22) PCT Filed: May 28, 2015

(86) PCT No.: PCT/GB2015/051543
§ 371 (c)(1),
(2) Date: Nov. 18, 2016

(87) PCT Pub. No.: WO2015/181545
PCT Pub. Date: Dec. 3, 2015

(65) Prior Publication Data
US 2017/0204134 A1 Jul. 20, 2017

(30) Foreign Application Priority Data
May 29, 2014 (GB) .................................. 1409538.4

(51) Int. Cl.
C07K 7/52 (2006.01)
C07K 1/08 (2006.01)
C07K 1/113 (2006.01)
C07K 1/107 (2006.01)

(52) U.S. Cl.
CPC .............. *C07K 1/088* (2013.01); *C07K 1/084* (2013.01); *C07K 1/1072* (2013.01); *C07K 1/113* (2013.01); *C07K 7/52* (2013.01)

(58) Field of Classification Search
CPC ........... C07K 1/088; C07K 1/084; C07K 7/52
See application file for complete search history.

(56) References Cited

U.S. PATENT DOCUMENTS

| 8,586,707 | B2* | 11/2013 | Lin | C07K 1/045 |
| | | | | 530/300 |
| 9,796,758 | B2* | 10/2017 | Melnyk | C07K 1/088 |
| 2017/0081360 | A1 | 3/2017 | Cobb et al. | |

OTHER PUBLICATIONS

Sanford (Macrocycles from Perhalogenated Heterocycles, Chem. Eur. J. 2003, 9, No. 7) (Year: 2003).*
Brotzel (Nucleophilicities of amino acids and peptides, Organic & Biomolecular Chemistry 2007, 5:3814-3820) (Year: 2007).*
Libre (Nucleophiles and Electrophiles—Chemistry LibreTexts, 2014) (Year: 2014).*
Montalbetti (Amide bond formation and peptide coupling, Tetrahedron 2005, 61: 10827-10852) (Year: 2005).*
Sandford (Macrocycles from Perhalogenated Heterocycles, Chem. Eur. J. 2003, 9, No. 7, of record) (Year: 2003).*

(Continued)

*Primary Examiner* — Sudhakar Katakam
(74) *Attorney, Agent, or Firm* — Rudy J. Ng; Bozicevic, Field & Francis LLP

(57) ABSTRACT

A method for preparing a cyclic peptide, derivative or analogue thereof is described. The method comprises contacting a peptide, derivative or analogue thereof with a fluoro-heteroaromatic compound to cyclise the peptide, derivative or analogue thereof.

18 Claims, 33 Drawing Sheets

Specification includes a Sequence Listing.

Formation of mono-cyclic peptides

Formation of multicyclic peptides

(56) References Cited

OTHER PUBLICATIONS

Brotzel (Nucleophilicities of amino acids and peptides, Organic & Biomolecular Chemistry 2007, 5:3814-3820, of record) (Year: 2007).*
Senger (The Element Effect Revisited: Factors Determining Leaving Group Ability in Activated Nucleophilic Aromatic Substitution Reactions, JOC 2012, 77:9535-9540) (Year: 2012).*
Han (Solvent Effect and Time-Dependent Behavior of C-Terminus Cysteine Modified Cecropin P1 Chemically Immobilized onto Polymer Surface, Langmuir 2011, 27:7042-7051) (Year: 2011).*
Montalbetti (Amide bond formation and peptide coupling, Tetrahedron 2005, 61: 10827-10852, of record) (Year: 2005).*
Cobb (2012) "Pentafluoropyridine: A useful peptide and peptoid building block," American Chemical Society 234th(1) p. Flou-28 1-1.
Hudson et al., (2013) "Synthesis of a novel tetrafluoropyridine containing amino acid and tripeptide," Tetrahedron Letters 54(36): 4865-4867.
Lee et al., (2011) "Design and Fcile Solid-Phase Synthesis of Conformationally Constrained Bicyclic Peptoids," Organic Letters 13(19) 5012-5015.
Li and Xu (2000) "1-Ethyl 2-Halopyridinium Salts, Highly Efficient Coupling Reagents for Hindered Peptide Synthesis both in Solution and Solid-Phase," Tetrahedron 56 8119-8131.
Webster et al., (2014) "A mild method for the synthesis of a novel dehydrobutyrine-containing amino acid," Tetrahedron 70(31) 4661-4020.

* cited by examiner

Formation of mono-cyclic peptides

Formation of multicyclic peptides

Side chain-to-side chain

Head-to-side chain

Side chain-to-tail

Head-to-tail

R1 = H, F, Br, Cl, $CH_3$, CN, $OCH_3$, $NH_2$, NHR, $CF(CF_3)_2$, $CF_3$, $SO_2Ph$, $NO_2$
R2 = H, F, Br, Cl, $CH_3$, CN, $OCH_3$, NH2, NHR, $CF(CF_3)_2$, $CF_3$, $SO_2Ph$, $NO_2$
R3 = H, F, Br, Cl, $CH_3$, CN, $OCH_3$, $NH_2$, NHR, $CF(CF_3)_2$, $CF_3$, $SO_2Ph$, $NO_2$
R4 = H, F, Br, Cl, $CH_3$, CN, $OCH_3$, $NH_2$, NHR, $CF(CF_3)_2$, $CF_3$, $SO_2Ph$, $NO_2$
R5 = H, F, Br, Cl, $CH_3$, CN, $OCH_3$, $NH_2$, NHR, $CF(CF_3)_2$, $CF_3$, $SO_2Ph$, $NO_2$

Chemical Formula: $C_{47}H_{46}F_{12}N_{12}O_{10}S_2$
Molecular Weight: 1231.06

Chemical Formula: $C_{37}H_{48}F_4N_{10}O_{12}$
Molecular Weight: 900.84

2.490 minutes            2.932 minutes

AcNH-Y-K-G-G-G-K-A-L-CONH₂

Ac-Tyr-Lys-Gly-Gly-Gly-Lys-Ala-Leu-NH₂

P7a

Chemical Formula: $C_{37}H_{48}F_4N_{10}O_{10}S_2$
Molecular Weight: 932.96

P14

Chemical Formula: $C_{42}H_{47}F_8N_{11}O_{10}S_2$
Exact Mass: 1081.28
Molecular Weight: 1082.01

Chemical Formula: $C_{116}H_{117}F_{16}N_{19}O_{12}S_2$
Molecular Weight: 2337.43

Chemical Formula: $C_{104}H_{117}F_4N_{19}O_{12}S_2$
Molecular Weight: 1965.31

Chemical Formula: $C_{106}H_{117}F_6N_{21}O_{12}S_2$
Molecular Weight: 2117.37

Chemical Formula: $C_{112}H_{117}F_{12}N_{23}O_{12}S_2$
Molecular Weight: 2269.42

Chemical Formula: $C_{112}H_{99}F_{32}N_{25}O_{12}S_4$
Molecular Weight: 2723.38

Chemical Formula: $C_{84}H_{103}F_8N_{23}O_{12}S_4$
Molecular Weight: 1907.12

Chemical Formula: $C_{88}H_{103}F_{12}N_{25}O_{12}S_4$
Molecular Weight: 2059.18

Chemical Formula: $C_{96}H_{99}F_{16}N_{29}O_{12}S_4$
Molecular Weight: 2283.25

Chemical Formula: $C_{100}H_{99}F_{20}N_{31}O_{12}S_4$
Molecular Weight: 2435.31

P5

Chemical Formula: $C_{47}H_{46}F_{12}N_{12}O_{10}S_2$
Molecular Weight: 1231.06

6a

Chemical Formula: $C_{42}H_{47}F_8N_{11}O_{10}S_2$
Molecular Weight: 1082.01

6b

Chemical Formula: $C_{42}H_{47}F_8N_{11}O_{10}S_2$
Molecular Weight: 1082.01

P7a

Chemical Formula: $C_{37}H_{48}F_4N_{10}O_{10}S_2$
Molecular Weight: 932.96

P7b

Chemical Formula: $C_{37}H_{48}F_4N_{10}O_{10}S_2$
Molecular Weight: 932.96

9a

Chemical Formula: $C_{42}H_{47}F_8N_{11}O_{12}$
Molecular Weight: 1049.89

9b

Chemical Formula: $C_{42}H_{47}F_8N_{11}O_{12}$
Molecular Weight: 1049.89

P10

Chemical Formula: $C_{47}H_{46}F_{12}N_{12}O_{12}$
Molecular Weight: 1198.94

P11

Chemical Formula: $C_{53}H_{60}F_{12}N_{14}O_{10}$
Molecular Weight: 1281.13

P12

Chemical Formula: $C_{37}H_{48}F_4N_{10}O_{12}$
Molecular Weight: 900.84

CYCLISING PEPTIDES

CROSS-REFERENCE TO RELATED APPLICATIONS

This application is the U.S. national phase under 35 U.S.C. § 371 of PCT International Application No. PCT/GB2015/051543, which has an international filing date of May 28, 2015 and designated the United States of America, which application claims benefit of priority to GB Application No. 1409538.4, filed May 29, 2014, the disclosures of each of which are incorporated by reference herein.

The present invention relates to cyclising peptides, derivatives or analogues thereof. More specifically, the invention relates to the formation of mono-cyclic and multi-cyclic peptides, derivatives or analogues thereof.

Protein-protein interactions are attractive drug targets due to their importance in cellular signalling, and their frequent alteration in a variety of disease states, including cancer (e.g. p53-MDM2 interaction) and cardiovascular disease (e.g. cAMP signalling pathways), as well as infectious diseases and those affecting the nervous system. Disruption of the interaction between two proteins in a signalling pathway can facilitate a beneficial effect in a range of disorders, many of which were previously considered to be extremely challenging targets. Compared with small molecules, peptides and peptide mimetics have great potential for very selectively and potently inhibiting intracellular protein-protein interactions (PPIs) due to their ability to mimic native protein structures and cover a large area of the often flat and featureless PPI interface. As such, peptide drugs have shown considerable promise as medicines, and investment in this area by the pharmaceutical industry continues to increase. Areas of significant interest lie in the use of stabilised or stapled α-helices, (multi)cyclic peptides and peptidomimetics.

However, many peptide drugs are readily broken down in the human body, presenting drug formulation and delivery challenges. Moreover, physical properties such as water-solubility and membrane-permeability remain highly problematic. Many drugs fail in development at the pre-clinical stage due to poor physical properties and many limitations remain in developing peptide-based drugs with suitable pharmaceutical properties e.g. membrane permeability, bio-availability and water solubility. Stapled peptides are an emerging class of therapeutic agent, which have superior proteolytic stability in vivo when compared with standard (non-constrained) peptide-based drugs. The foremost method of peptide stapling employs the use of the all-hydrocarbon (alkene) linker pioneered by Grubbs and Verdine.[i,ii] This strategy is used to stabilise a peptide α-helix and can often improve biological activity.[iii,iv] Moreover, Aileron Therapeutics (USA) have completed a 'first in human' clinical study on a stapled peptide and have also announced that they will soon be evaluating a stapled peptide inhibitor of the p53-MDM2 interaction as an anticancer agent in clinical trials. Roche have recently invested $1.1 billion in Aileron underlining the growing importance of this drug modality.

A number of methods are currently available to facilitate the constraint of peptides by cyclisation and involve either: head-to-tail cyclisation; side chain-to-tail cyclisation; head-to-side chain cyclisation or side chain-to-side chain cyclisation.[v] These typically involve cyclisation through cysteine residues, which react with an electrophilic aromatic molecule as a template.

As previously mentioned, there is a large demand for synthesis of cyclic peptide products. Accordingly, research is being carried out in industry. An example of this is the research carried out by Pepscan Therapeutics NV. Pepscan have developed technology called the CLIPS™ (Chemical LInkage of Peptides onto Scaffold) technology platform that can be used to make cyclic and multi-cyclic peptides. However, this technology is limited because it can only be used to facilitate reactions with cysteine residues. It would be advantageous to be able to carry out reactions using other amino acids residues, such as lysine or tyrosine. Additionally, Pepscan use reagents containing bromine for cyclisation. A problem is that these reagents do not allow for easy in-situ monitoring of the cyclisation reactions. Finally, Pepscan's technology has only been used with peptides and proteins, and it would be highly advantageous to have technology which is compatible with peptoids, i.e. poly-N-substituted glycine.

As well as research being conducted in industry, a large amount of research has also been carried out in academia. One such group focused on this area is the Pentelute group at MIT. The Pentelute group have reported using hexafluorobezene derivatives to make cyclic peptides. They have published two papers in the area, namely: Zou et al. Pentelute *Org. & Biomol. Chem.* 2014, 12, 566-573 and Spokoyny et al. Pentelute *J. Am. Chem. Soc.* 2013, 135, 5946-5949. However, as with the technology developed by Pepscan, the MIT team carry out reactions using peptides that cyclise only via a cysteine residue. As mentioned previously, it would be advantageous to be able to carry out cyclisation reactions using other amino acid residues. Additionally, the Pentelute group have not carried out any reactions using peptoid substrates and they also have not prepared multi-cyclic peptide scaffolds.

Finally, the Lim group has also published a paper in a related area: Lee, J. H. et al. *"Design and facile solid-phase synthesis of conformationally constrained bicyclic peptoids."* Org. Lett. 2011, 13, 5012-5015. The Lim group have been able to form cyclic and multi-cyclic peptide-peptoid hybrids using cyanuric chloride. However, the tagging and cyclisation reactions are carried out with the peptides attached to a resin support, because cyanuric chloride reacts with the side chains of amino acids and gives rise to by-products if the reactions are carried out on un-protected (i.e. unsupported) peptoids. It would therefore be beneficial to use more selective reactions that are less prone to unwanted side reactions, which would enable cyclisation reactions to be conduced in solution rather than on a resin support. Additionally, the Lim group only used peptoid-peptide hybrids, and the use of cyanuric chloride does not allow for easy in-situ real-time monitoring of the reactions.

This invention arises from the inventors' work in trying to overcome the disadvantages of the prior art. The inventors have investigated the direct $S_NAr$ reaction between perfluoroheteroaromatic based reagents and peptides with nucleophilic side chains, and have found that such reagents can be effectively used to prepare cyclic peptides, derivative or analogue thereof. The inventors have also highlighted the various exploitable outcomes from the reaction between perfluoroheteroaromatic reagents with cysteine, serine, tyrosine and lysine, as well as mixed functionality-containing peptides and peptoids.

Thus, according to a first aspect of the invention, there is provided a method for preparing a cyclic peptide, derivative or analogue thereof, the method comprising contacting a peptide, derivative or analogue thereof with a fluoro-heteroaromatic compound to cyclise the peptide, derivative or analogue thereof.

In a second aspect, there is provided use of a fluoro-heteroaromatic compound to cyclise a peptide, derivative or analogue thereof.

Advantageously, and preferably, the method of the invention enables the cyclisation of peptides, derivatives or analogues thereof using the direct $S_NAr$ reaction between fluoro-heteroaromatic-based reagents and peptides with nucleophilic side chains. This also allows the reaction to be monitored in-situ in real-time using $^{19}F$ NMR. Prior art approaches for forming cyclic peptides only utilise cysteine residues as nucleophiles, whereas the method of the first aspect surprisingly enables cyclisation with other nucleophilic amino acids in a peptide system, including cysteine, serine, lysine and tyrosine.

The term "derivative or analogue thereof" can mean that the amino acids residues of the peptide, which is cyclised, are replaced by residues (whether natural amino acids, non-natural amino acids or amino acid mimics) with similar side chains or peptide backbone properties. Additionally, the terminals of such peptides may be protected by N- and C-terminal protecting groups with similar properties to acetyl or amide groups.

Derivatives and analogues of peptides according to the invention may also include those that increase the peptide's half-life in vivo. For example, a derivative or analogue of the peptide of the invention may include peptoid and retropeptoid derivatives of the peptides, peptide-peptoid hybrids and D-amino acid derivatives of the peptides.

Peptoids, or poly-N-substituted glycines, are a class of peptidomimetics whose side chains are appended to the nitrogen atom of the peptide backbone, rather than to the alpha-carbons, as they are in amino acids. Peptoid derivatives of the peptides of the invention may be readily designed from knowledge of the structure of the peptide. A retropeptoid is expected to bind in the opposite direction in the ligand-binding groove, as compared to a peptide or peptoid-peptide hybrid containing one peptoid residue. As a result, the side chains of the peptoid residues are able point in the same direction as the side chains in the original peptide.

Preferably, the peptide comprises at least two, three, four or five amino acid residues. Preferably, the peptide comprises a polypeptide. Preferably, the polypeptide comprises at least five, ten or fifteen amino acid residues.

Preferably, the fluoro-heteroaromatic compound contains at least one nitrogen atom in its aromatic ring. The fluoro-heteroaromatic compound may contain one, two or three nitrogen atoms in the aromatic ring. Accordingly, the fluoro-heteroaromatic compound may comprise a fluoropyridine, a fluoropyrazine, a fluoropyrimidine, a fluoropyridazine or a fluorotriazine. In one preferred embodiment, the fluoro-heteroaromatic compound comprises a fluoropyridine. In an alternative preferred embodiment, the fluoro-heteroaromatic compound comprises a fluoropyrimidine or a fluoropyridazine.

The fluoro-heteroaromatic compound may comprise a fused six-membered ring. Accordingly, the fluoro-heteroaromatic may comprise a fluoroquinoline, a fluoroisoquinoline, a fluoroquinoxaline, a fluoroquinazoline, a fluorocinnoline, a fluorophthalazine or a fluoroacridine. Preferably, the fluoro-heteroaromatic compound comprises a fluoroquinoline.

Preferably, the fluoro-heteroaromatic compound contains at least two halogen atoms, wherein at least one of the halogen atoms is a fluorine atom, and each halogen atom is covalently bonded to a carbon atom in the aromatic ring.

Accordingly, in embodiments where the heteroaromatic compound comprises one six-membered ring which contains one nitrogen atom in the aromatic ring then it may contain two, three, four or five halogen atoms, wherein each halogen atom is bonded to a carbon atom in its aromatic ring. In embodiments where the heteroaromatic compound one six-membered ring which contains two nitrogen atoms in the aromatic ring then it may contain two, three or four halogen atoms, wherein each halogen atom is bonded to a carbon atom in its aromatic ring. In embodiments where the heteroaromatic compound one six-membered ring which contains three nitrogen atoms in the aromatic ring then it may contain two or three halogen atoms, wherein each halogen atom is bonded to a carbon atom in its aromatic ring.

In one preferred embodiment, the at least two halogen atoms only comprise fluorine atoms.

In embodiments where the heteroaromatic compound comprises one six-membered ring which contains one nitrogen atom in the aromatic ring then it may contain one, two, three, four or five fluorine atoms, wherein each fluorine atom is bonded to a carbon atom in its aromatic ring. In embodiments where the heteroaromatic compound comprises one six-membered ring which contains two nitrogen atoms in the aromatic ring then it may contain one, two, three or four fluorine atoms, wherein each fluorine atom is bonded to a carbon atom in its aromatic ring. In embodiments where the heteroaromatic compound comprises one six-membered ring which contains three nitrogen atoms in the aromatic ring then it may contain one, two or three fluorine atoms, wherein each fluorine atom is bonded to a carbon atom in its aromatic ring.

In one embodiment, the fluoro-heteroaromatic compound comprises at least one hydrogen atom, wherein each hydrogen atom is covalently bonded to a carbon atom in the aromatic ring. Preferably, the fluoro-heteroaromatic compound comprises 2,3,4,6-tetrafluoropyridine.

In a preferred embodiment, therefore, the fluoro-heteroaromatic compound comprises a perfluoroaromatic compound. Preferably, the fluoro-heteroaromatic compound comprises perfluoropyridine, perfluoropyridazine or perfluoroquinoline.

In another preferred embodiment, the fluoro-heteroaromatic compound comprises a pentafluoroaromatic compound, most preferably pentafluoropyridine.

Alternatively, the at least two halogen atoms may comprise at least one chlorine atom, at least one bromine atom and/or at least one iodine atom.

In an alternative preferred embodiment, the at least two halogen atoms comprise at least one fluorine atom and at least one chlorine atom.

The heteroaromatic compound may comprise 1, 2, 3 or 4 chlorine atoms, wherein each chlorine atom is bonded to a carbon atom in its aromatic ring.

In another preferred embodiment, the fluoro-heteroaromatic compound comprises a chloro-fluoro-heteroaromatic compound, most preferably 3,5-dichloro-2,4,6-trifluoropyridine, 2,3,4,5-tetrachloro-6-fluoropyridine or 5-chloro-2,4,6-trifluoropyrimidine.

Preferably, the peptide, derivative or analogue thereof contains at least two nucleophilic side chains. Preferably, a first nucleophilic side chain reacts in an $S_NAr$ type reaction with the fluoro-heteroaromatic compound to displace a fluorine atom and create a covalent bond between the first nucleophilic side chain and the fluoro-heteroaromatic compound, and subsequently a second nucleophilic side chain reacts in an $S_NAr$ type reaction with the fluoro-heteroaromatic compound, which is covalently bonded to the first nucleophilic side chain, to displace a further fluorine ion and create a covalent bond between the second nucleophilic side chain and the fluoro-heteroaromatic compound, thereby creating a linker between the first and second nucleophilic side chains, and thereby forming the cyclic peptide, derivative or analogue thereof.

The term "linker" can mean a heteroaromatic molecule which has reacted in an $S_NAr$ type reaction with at least two nucleophilic side chains and is covalently bonded to each of the at least two nucleophilic side chains.

Preferably, the peptide, derivative or analogue thereof contains at least three nucleophilic side chains. Preferably, the peptide, derivative or analogue thereof contains at least four nucleophilic side chains.

In one embodiment, at least one of the nucleophilic side chains comprises a thiol group. The or each thiol may be provided on a cysteine residue or modified cysteine residue in the peptide, derivative or analogue thereof.

In another embodiment, at least one of the nucleophilic side chains comprises an amine group, wherein the amine group preferably comprises a primary amine or secondary amine. The or each amine group may be provided on any amino acid residue within the peptide, derivative or analogue thereof. For example, the or each amine group may be provided on a lysine residue in the peptide, derivative or analogue thereof.

In yet another embodiment, at least one of the nucleophilic side chains comprises an alcohol group, wherein the alcohol group preferably comprises a phenol group. The or each alcohol group may be provided on a tyrosine, serine or threonine residue within the peptide, derivative or analogue thereof. Preferably, the or each alcohol group may be provided on a tyrosine residue in the peptide, derivative or analogue thereof.

The cyclic peptide, derivative or analogue thereof that is prepared with the method of the first aspect may be monocyclic. Monocyclic can mean that one linker is created, which links a first nucleophilic side chain to a second nucleophilic side chain in the cyclic peptide, derivative or analogue thereof.

Alternatively, the cyclic peptide, derivative or analogue thereof that is prepared may be multi-cyclic. Multi-cyclic can mean that at least two linkers are created, whereby a first linker links a first nucleophilic side chain to a second nucleophilic side chain and a second linker links a third nucleophilic side chain to a fourth nucleophilic side chain in the peptide, derivative or analogue thereof. Alternatively, multi-cyclic can also mean that one linker is created whereby the linker links a first nucleophilic side chain to a second nucleophilic side chain, and additionally links both the first and second nucleophilic side chains to a third nucleophilic side chain.

It will be appreciated that the distance between the at least two, three or four nucleophilic side chains, and their type (i.e. thiol, amine or phenol group) will dictate the number and characteristics of the cyclisation of the peptide, derivative or analogue thereof. Therefore, the nucleophilic side chains which become linked by a linker as a result of the method of the first aspect may be at least one, two, three, four or five amino acid residues apart. However, in some embodiments, the nucleophilic side chains which become linked by a linker as a result of the method of the invention may be at least six, seven, eight, nine or ten amino acid residues apart.

Preferably, the peptide, derivative or analogue thereof being cyclised in the method of the invention is not attached to a support (e.g. a resin support). In contrast, the method is preferably carried out with the peptide, derivative or analogue thereof in solution using a solvent. The solvent used may be dimethylformamide (DMF). Preferably, however, the solvent used may be 2,2,2-trifluoroethanol (TFE). The inventors have also demonstrated that trifluoroethanol can be used as a solvent to tune the reactivity of the reaction and allows a more selective reaction with the nucleophilic residues on the peptides.

Hence, in an embodiment where the peptide, derivative or analogue thereof contains at least two nucleophilic side chains, the method may be used to selectively control which of the nucleophilic side chains react with the fluoro-heteroaromatic compound. The method may be selectively controlled due to selection of the solvent. Alternatively, the method may be controlled due to the temperature at which the reaction is carried out.

In one preferred embodiment, the at least two nucleophilic side chains comprise at least one thiol group and at least one phenol group. Advantageously, in this embodiment, it is possible to selectively react the fluoro-heteroaromatic compound with the at least one thiol group. Preferably, 2,2,2-trifluoroethanol (TFE) solvent is used.

In another preferred embodiment, the at least two nucleophilic side chains comprise at least one amine group and at least one phenol group. Advantageously, in this embodiment, it is possible to selectively react the fluoro-heteroaromatic compound with the at least one amine group. Preferably, 2,2,2-trifluoroethanol (TFE) solvent is used.

In yet another preferred embodiment, the at least two nucleophilic side chains comprise at least one thiol group and at least one amine group. In this embodiment, it is possible to selectively react the fluoro-heteroaromatic compound with the at least one thiol group. Preferably, 2,2,2-trifluoroethanol (TFE) solvent is used.

Preferably, the method comprises dissolving a peptide, derivative or analogue thereof in a solvent, and adding a base thereto before the fluoro-heteroaromatic compound is added to the dissolved peptide to create a reaction solution. Preferably, the reaction solution is mixed (e.g. by shaking) for at least one hour. Preferably, the base is N,N-diisopropylethylamine (DIPEA).

Optionally, once the above steps have been completed the solution may be subjected to a vacuum to remove any volatile liquids.

Preferably, the step of mixing the solution lasts for at least two hours. Further preferably, the step of mixing the solution lasts for at least three hours. Further preferably, the step of mixing the solution lasts for at least four hours. Further preferably, the step of mixing the solution lasts for at least five hours.

Preferably, the step of mixing the solution is undertaken at room temperature. Alternatively, the step of mixing the solution is undertaken at at least 30° C. and preferably at least 40° C., and further preferably at least 50° C.

Preferably, the molar ratio of the peptide, derivative or analogue thereof to the fluoro-heteroaromatic compound is between 1:1 and 1:100. More preferably, the molar ratio is between 1:5 and 1:50, or even more preferably between 1:10 and 1:40, and most preferably between 1:20 and 1:30.

Preferably, the concentration of the peptide, derivative or analogue thereof in the reaction solution is less than 5 mM. More preferably, the concentration of the peptide, derivative or analogue thereof in the reaction solution is less than 4 mM, 3 mM, 2 mM, 1 mM, or 0.75 mM.

Preferably, the concentration of the peptide, derivative or analogue thereof in the reaction solution is at least 0.01 mM. More preferably, the concentration of the peptide, derivative or analogue thereof in the reaction solution is at least 0.05 mM, 0.10 mM, 0.15 mM, 0.20 mM or 0.25 mM.

Accordingly, in one preferred embodiment, the concentration of the peptide, derivative or analogue thereof in the reaction solution is between 5 mM and 0.01 mM. Preferably, the concentration of the peptide, derivative or analogue thereof in the reaction solution is between 4 mM and 0.05 mM, between 3 mM and 0.10 mM, between 2 mM and 0.15 mM, or between 1 mM and 0.2 mM. More preferably, the concentration of the peptide, derivative or analogue thereof in the reaction solution is between 0.75 mM and 0.25 mM.

However, in an alternative embodiment, the concentration of the peptide, derivative or analogue thereof in the reaction solution is preferably at least 0.5 mM, 1 mM, 1.5 mM or 2 mM.

Accordingly, in an alternative preferred embodiment, the concentration of the peptide, derivative or analogue thereof in the reaction solution is between 5 mM and 1 mM. Preferably, the concentration of the peptide, derivative or analogue thereof in the reaction solution is between 4 mM and 1.5 mM. More preferably, the concentration of the peptide, derivative or analogue thereof in the reaction solution is between 3 mM and 2 mM.

Preferably, the concentration of the fluoro-heteroaromatic compound in the reaction solution is less than 250 mM. More preferably, the concentration of the fluoro-heteroaromatic compound in the reaction solution is less than 200 mM, 150 mM, or 100 mM. Most preferably, the concentration of the fluoro-heteroaromatic compound in the reaction solution is less than 75 mM, 50 mM, 25 mM, 20 mM or 15 mM.

Preferably, the concentration of the fluoro-heteroaromatic compound is less in the reaction solution is at least 1 mM. More preferably, the concentration of the peptide, derivative or analogue thereof in the reaction solution is at least 2 mM, 3 mM, 4 mM, or 5 mM. Most preferably, the concentration of the peptide, derivative or analogue thereof in the reaction solution is at least 6 mM, 7 mM, 8 mM, 9 mM or 10 mM.

Accordingly, in one preferred embodiment, the concentration of the fluoro-heteroaromatic compound in the reaction solution is between 250 mM and 1 mM. Preferably, the concentration of the heteroaromatic compound in the reaction solution is between 200 mM and 2 mM, between 150 mM and 3 mM, or between 100 mM and 4 mM. More preferably, the concentration of the heteroaromatic compound in the reaction solution is between 75 mM and 5 mM, between 50 mM and 6 mM, between 25 mM and 7 mM or between 20 mM and 8 mM. Most preferably, the concentration of the heteroaromatic compound in the reaction solution is between 15 mM and 10 mM.

However, in an alternative embodiment, the concentration of the heteroaromatic compound in the reaction solution is preferably at least 15 mM, 20 mM, 25 mM or 30 mM. More preferably, the concentration of the heteroaromatic compound in the reaction solution is preferably at least 35 mM, 40 mM, 45 mM, or 50 mM.

Accordingly, in an alternative preferred embodiment, the concentration of the heteroaromatic compound in the reaction solution is between 250 mM and 15 mM. Preferably, the concentration of the heteroaromatic compound in the reaction solution is between 200 mM and 20 mM, between 150 and 30 mM. More preferably, the concentration of the heteroaromatic compound in the reaction solution is between 100 mM and 40 mM. Most preferably, the concentration of the heteroaromatic compound in the reaction solution is between 75 mM and 50 mM.

According to a third aspect of the invention, there is provided a method for producing a cyclic peptide, derivative or analogue thereof in a single step or "one-pot" reaction, the method comprising carrying out a method according to the first aspect of the invention once.

The phrase "one-pot" reaction can mean that the method step is carried out once to produce the cyclic peptide, derivative or analogue thereof.

According to a fourth aspect of the invention, there is provided a method for producing a cyclic peptide, derivative or analogue thereof in a "step-wise" fashion, the method comprising at least two steps sequentially, wherein the first step comprises carrying out a method according to the first aspect of the invention and the second step comprises carrying out a method according to the first aspect of the invention.

According to a fifth aspect of the invention, there is provided a method for producing a cyclic peptide, derivative or analogue thereof in a "step-wise" fashion, the method comprising at least two steps sequentially, wherein the first step comprises contacting a peptide, derivative or analogue thereof with a fluoro-heteroaromatic compound to create a chemically modified peptide, derivative or analogue thereof, and the second step comprises contacting the chemically modified peptide, derivative or analogue thereof with a fluoro-heteroaromatic compound to cyclise the chemically modified peptide, derivative or analogue thereof.

The solvent for the first step may be different to the solvent for the second step. For example, preferably TFE is the solvent for the first step and DMF is the solvent for the second step. This is because only selected nucleophilic side chains will react when TFE is the solvent leaving selected nucleophilic side chains unreacted after the first step has been carried out, but these unreacted nucleophilic side chains may then react when DMF is used as the solvent for the second step.

Alternatively, or additionally, the peptide, derivative or analogue thereof may comprise at least one protecting group. The at least one protecting group may be configured to protect one or more nucleophilic side chains on the peptide, derivative or analogue thereof. The method may comprise removing the at least one protecting group after the first step is completed and before the second step.

The second step may comprise contacting the peptide, derivative or analogue thereof with a fluoro-heteroaromatic compound which is added to the reaction during the second step. Alternatively, the second step may comprise further contacting the peptide, derivative or analogue thereof with a fluoro-heteroaromatic compound which is already attached to the peptide, derivative or analogue thereof by at least one chemical bond.

According to a sixth aspect of the invention, there is provided a cyclic peptide, derivative or analogue thereof obtained or obtainable by the method according to the first, third, fourth or fifth aspect of the invention.

The inventors have found that incorporation into the peptide, derivative or analogue thereof of a fluoro-heteroaromatic group provides a very useful functional group that enables both $^{19}$F NMR analysis and further chemical modification such as the formation of cyclic peptides.

Hence, in a seventh aspect, there is provided use of $^{19}$F NMR to monitor the method according to the first aspect of the invention.

This allows in-situ real-time monitoring of the reaction pathway and, given the properties of $^{19}$F NMR, precise structural information can also be obtained.

Monitoring may involve analysis by $^{19}$F NMR to see if the desired products have formed, checking to see if any additional products have formed, and/or checking to see if any unreacted reagents are present.

All features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying Figures, in which:—

FIG. 41 shows the chemical structure for product P7a;

EXAMPLES

Figure 2:
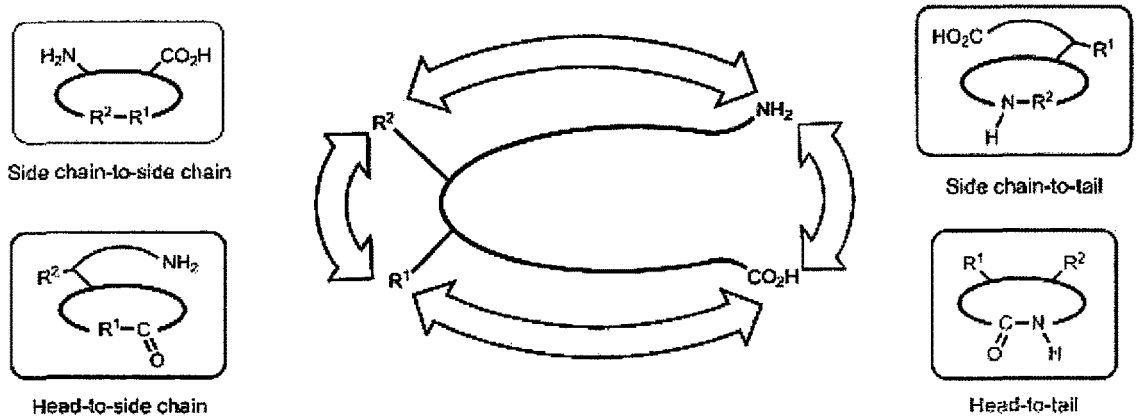
FIG. 2 is a schematic diagram showing the different types of cyclisation reactions for peptides.

As mentioned previously, it is desirable to be able to react peptides, derivatives or analogues thereof to form monocyclic or multi-cyclic products. These reactions can be at least one of: head-to-tail cyclisation; side chain-to-tail cyclisation; head-to-side chain cyclisation and/or side chain-to-side chain cyclisation, as shown in FIG. 2.

Figure 3:
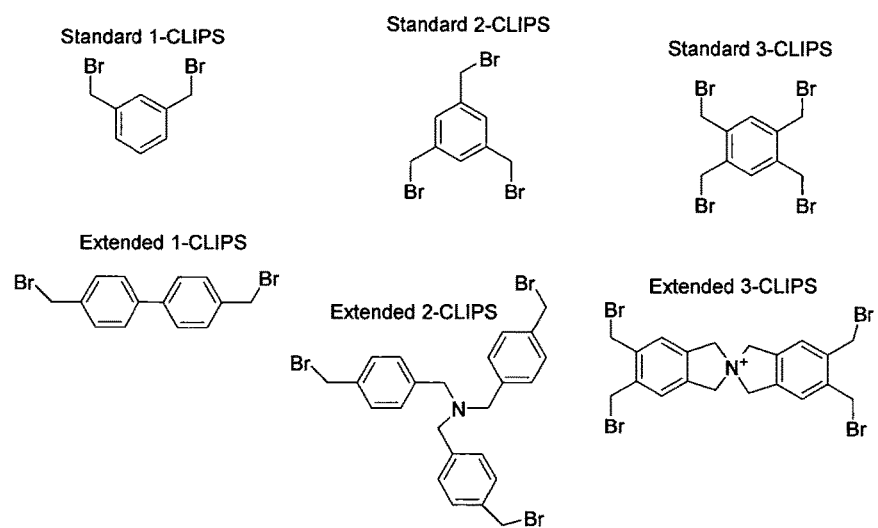
FIG. 3 shows the reagents used in the prior art by Pepscan Therapeutics NV.
Figure 4:
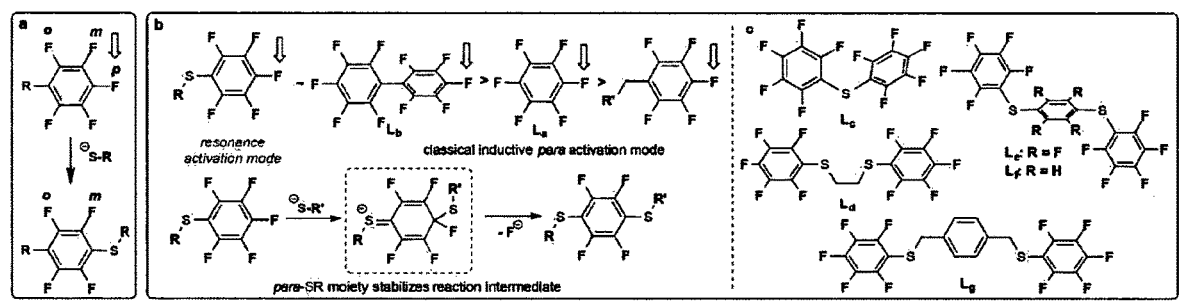
FIG. 4 shows the reagents used in the prior art by the Pentelute group at MIT.
Figure 5:
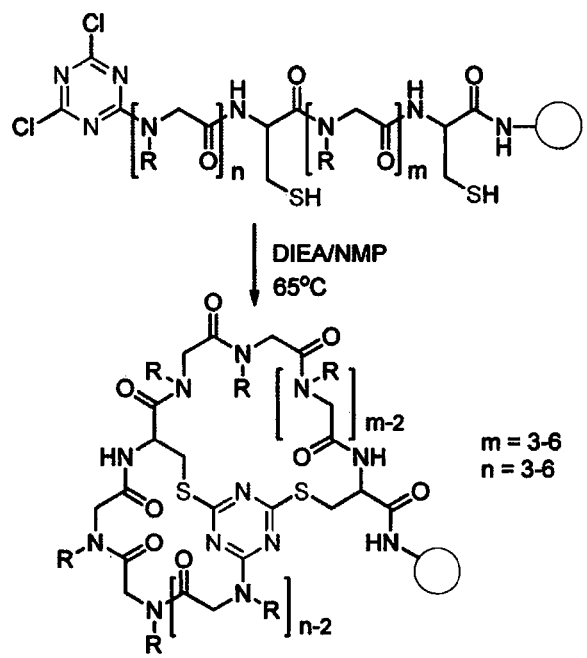
FIG. 5 shows a chemical reaction from the prior art resulting in the formation of a cyclic peptide-peptoid hybrid.

The reagents and methods used in the prior art have a number of drawbacks as discussed above. FIG. 3 shows reagents used by Pepscan. These reagents all contain bromine which does not allow for easy monitoring of the reactions. The reagents used by the Pentelute group are shown in FIG. 4. These reagents are fairly unreactive so, as with the Pepscan, they can only be used with peptides which contain cysteine. Finally, the reaction scheme developed by the Lim group is shown in FIG. 5. However, to avoid unwanted by-products this reaction must be carried out on resin. Additionally, as with the Pepscan reagents, the cyanuric chloride used by the Lim group does not allow for easy monitoring of the reactions.

Figure 1:
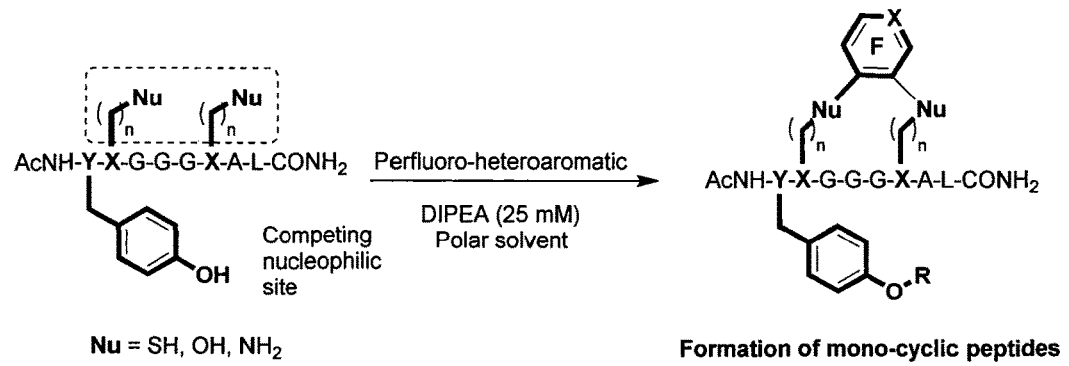
FIG. 1 shows two chemical reactions, the first resulting in the formation of a mono-cyclic peptide, and the second resulting in the formation of a multi-cyclic peptide.
Figure 6:
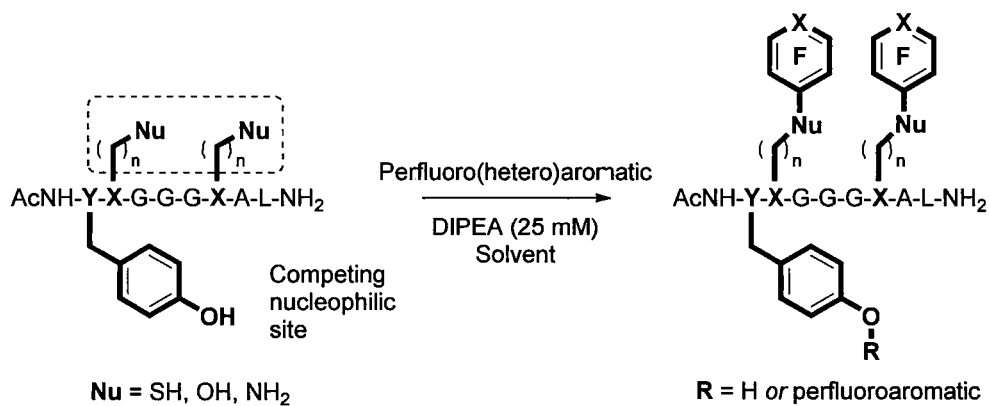
FIG. 6 shows a chemical reaction between a peptide and a perfluoro-heteroaromatic reagent.
Figure 7:
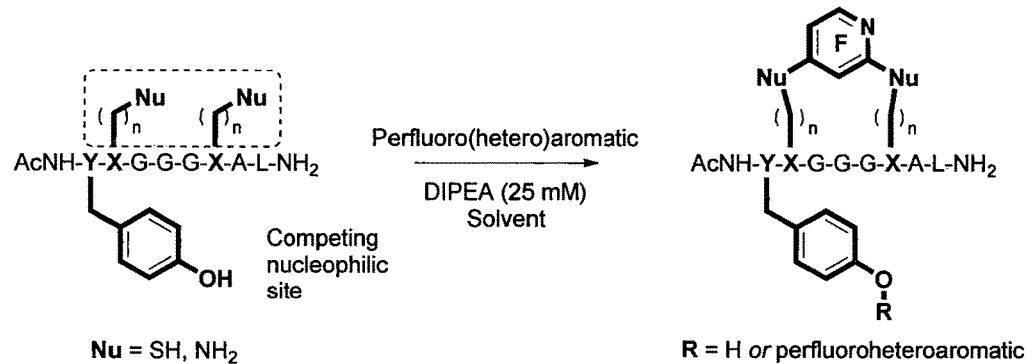
FIG. 7 shows a chemical reaction for peptide cyclisation using perfluoro-heteroaromatic reagents according to an embodiment of the invention.

The inventors' work has lead to the discovery of using fluoro-heteroaromatic compounds as a reagent in the cyclisation reactions of peptides, peptoids and peptide-peptoid hybrids. This can either be done as a one step reaction, as illustrated in FIGS. 1 and 7, or as a two step process, where the peptide, peptoid or peptide-peptoid hybrid is first tagged, as illustrated in FIG. 6, and then further reacted to cyclise.

Materials and Methods

The following examples were carried out on ten different peptides, referred to as peptides 1 to 10, and two different peptoids, referred to as peptoids 1 and 2, where:

Peptide 1 has the structure AcNH—Y—C-G-G-G-C-A-L-$CONH_2$;

Peptide 2 has the structure AcNH—Y—S-G-G-G-S-A-L-$CONH_2$;

Peptide 3 has the structure AcNH—Y—K-G-G-G-K-A-L-$CONH_2$;

Peptide 4 has the structure AcNH—F—K-A-C-G-K-G-C-A-$CONH_2$;

Peptide 5 is glutathione;

Peptide 6 has the structure AcNH—F—C(Acm)-G-G-C-G-G-C(Acm)-A-L-$CONH_2$;

Peptide 7 has the structure AcNH-A-C—W-G-S—I-L-A-R-T-$CONH_2$;

Peptide 8 has the structure AcNH-A-C—Y-G-S—I-L-A-R-T-$CONH_2$;

Peptide 9 has the structure AcNH—F—C-G-G-G-C-A-L-$CONH_2$; and

Peptide 10 has the structure AcNH—F—S-G-G-G-S-A-L-$CONH_2$;

Peptoid 1 is [(Nae-Nspe-Nspe)(NCys-Nspe-Nspe)]$_2$; and

Peptoid 2 is [Nae-NCys-Nspe]$_4$.

Peptides 1 to 4 and 6 to 10 were prepared using automated Fmoc-SPPS methods on a Liberty 1 peptide synthesiser (CEM) with microwave-assisted couplings (single coupling per amino acid; 10 min, 75° C. (50° C. for Fmoc-cys(trt)-OH coupling). Solid phase synthesis was conducted using Rink amide resin (0.7 mol/g loading) on a 0.1 mol scale, employing PyBOP and DIPEA as activator and base, respectively. Following on-resin synthesis of the appropriate sequence, N-terminal capping was achieved using $Ac_2O$/DMF (20%, 2×15 min) with shaking at room temperature. Finally, peptides were cleaved from the resin as the C-terminal amide by treatment of beads with a cleavage cocktail containing 90% TFA, 5% TIPS and 5% water with shaking at room temperature for 4 h. After removal of volatiles in vacuo, the product was triturated and washed using $Et_2O$.

Peptide 5, glutathione, can be bought commercially.

Peptoids 1 and 2 were prepared via automated peptoid synthesis using an Aapptec Apex 396 synthesiser. Solid phase synthesis was conducted using Rink Amide resin (0.1 mmol, loading 0.54 mmol g-1) by cycles of haloacetylation (either bromo- or chloroacetic acid, 1 ml, 0.6M in DMF) using DIC as activator (0.18 ml, 50% v/v in DMF, 20 min at RT) followed by halide displacement by the desired amine (1 ml, 1.5M in DMF, 60 min at RT) until the desired sequence was achieved. Finally peptoids were cleaved off the resin using 95:5:5 TFA:TIPS:H2O (4 ml, 30 min, RT). The cleavage cocktail containing the target peptoids was then filtered from the resin and evaporated in vacuuo and the resulting residue precipitated in Et2O (~20 ml). The crude peptoid was obtained via centrifugation to yield the crude product as a white/yellow powder.

Figure 8:
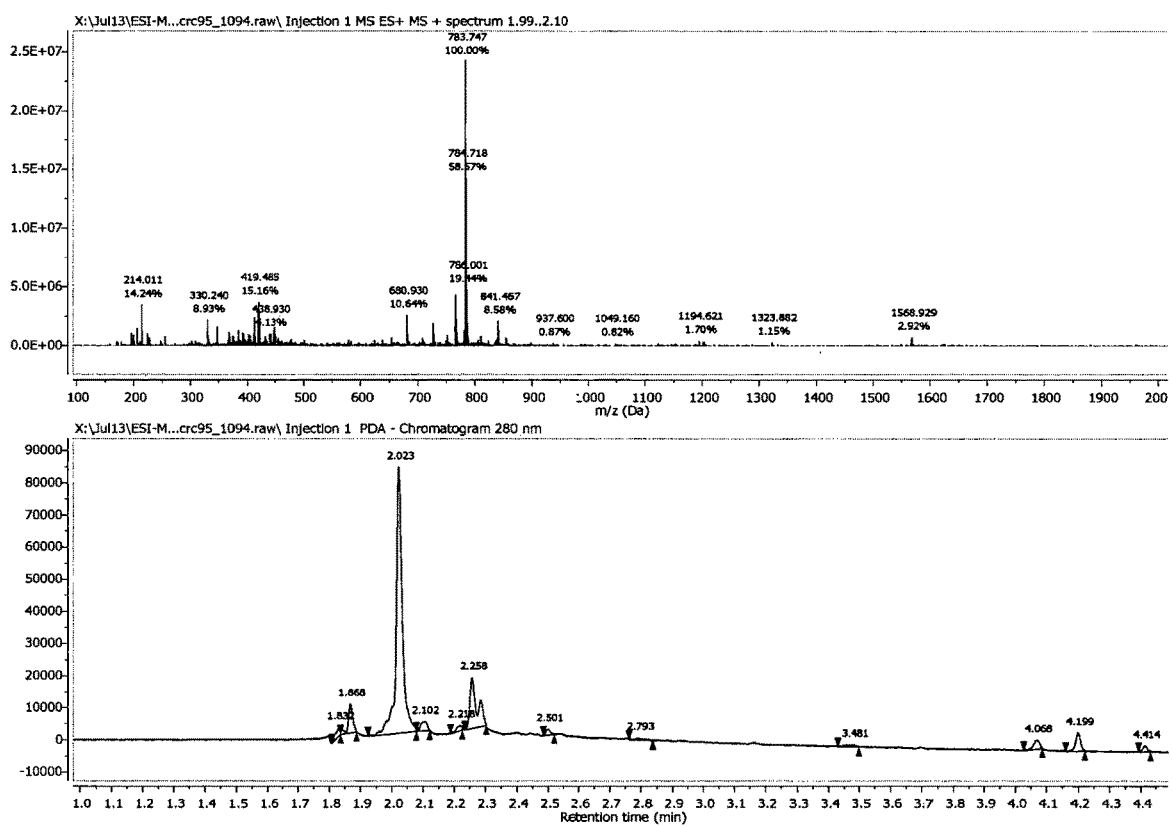
FIG. 8 is an LCMS spectrum and chromatogram at 280 nm for peptide 1, which has the structure AcNH—Y—C-G-G-G-C-A-L-CONH$_2$.
Figure 9:
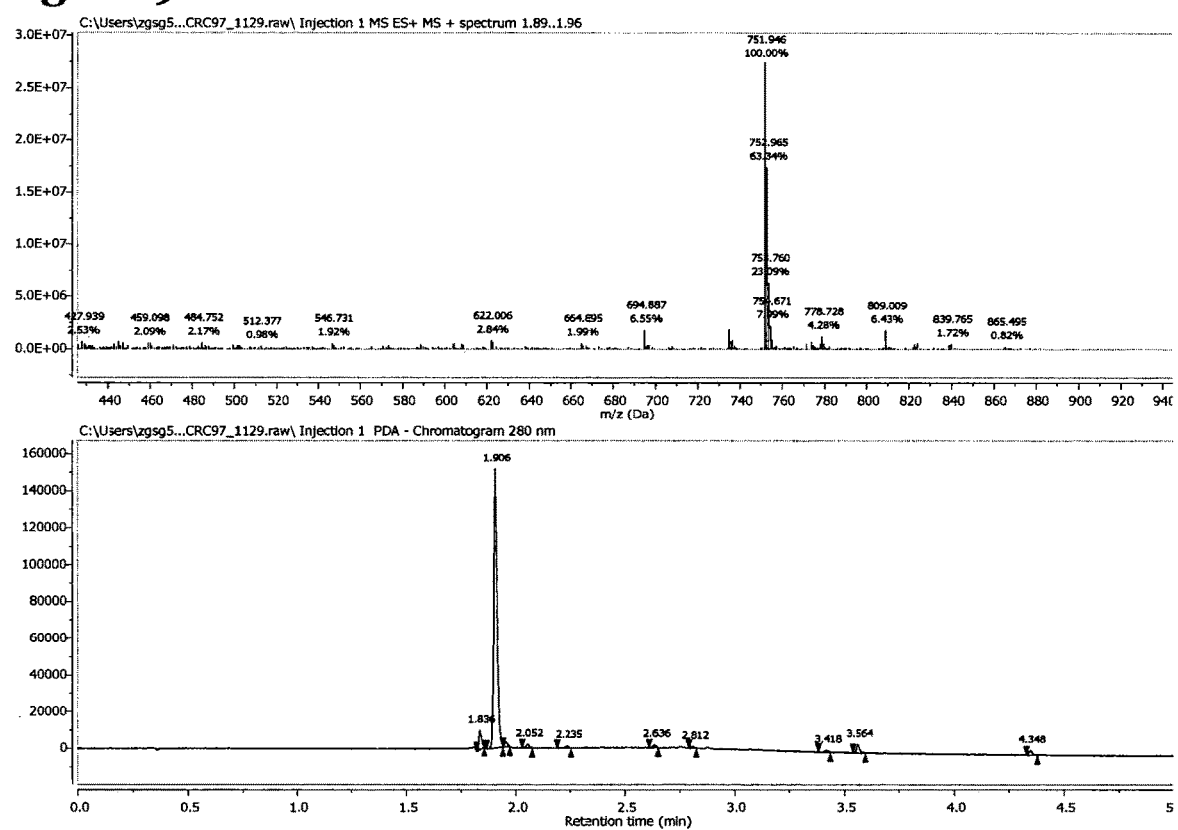
FIG. 9 is an LCMS spectrum and chromatogram at 280 nm for peptide 2, which has the structure AcNH—Y—S-G-G-G-S-A-L-CONH$_2$.
Figure 10:
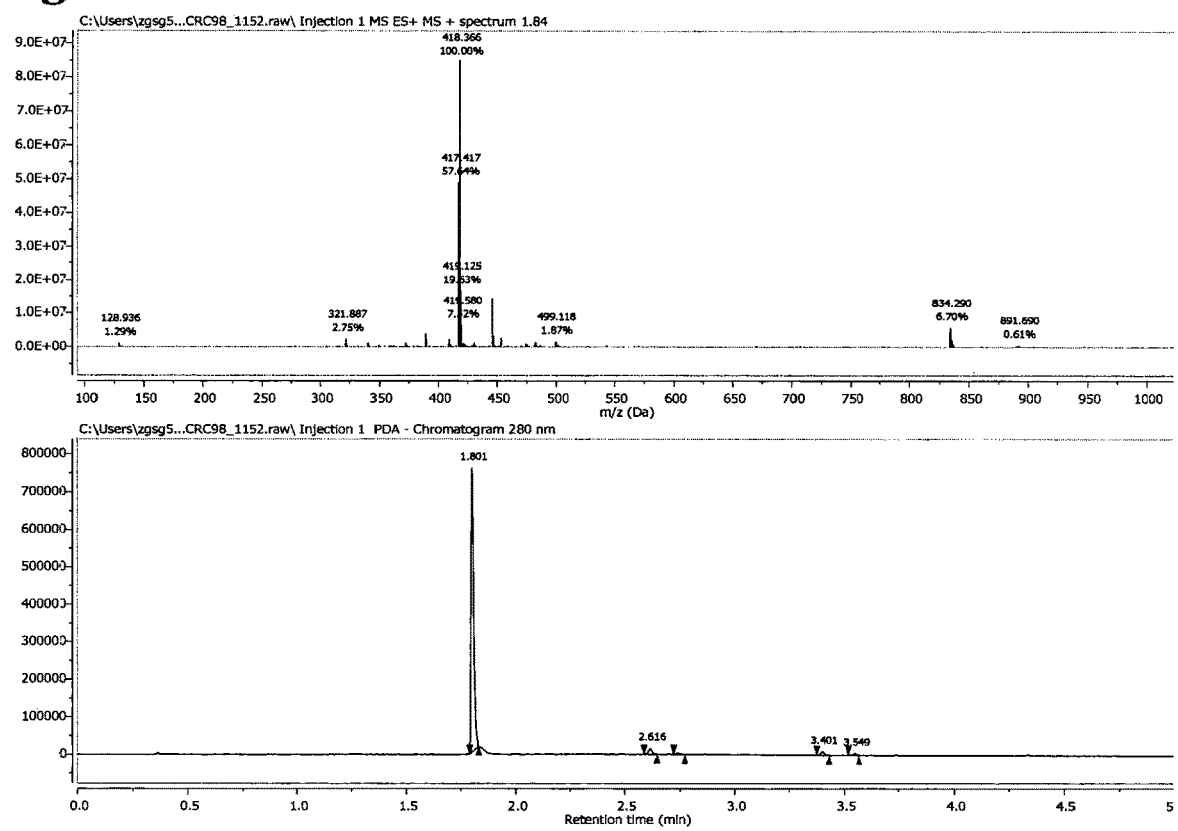
FIG. 10 is an LCMS spectrum and chromatogram at 280 nm for peptide 3, which has the structure AcNH—Y—K-G-G-G-K-A-L-CONH$_2$.

Mass spectroscopy data was collected for peptides 1 to 3 and is shown in FIGS. 8 to 10. FIG. 8, for peptide 1, shows an [M+H]$^+$ peak at 783.747 m/z, FIG. 9, for peptide 2, shows an [M+H]$^+$ peak at 751.946 m/z and FIG. 10, for peptide 3, shows an [M+H]$^+$ peak at 834.290 m/z and an [M+H]$^{2+}$ peak at 418.366 m/z.

The peptides or peptoids were reacted according to procedures A, B, D, E, F, G, H or I as described below:

Procedure A

Solid peptide (approx. 2 mg, 2.5 µmol) was dissolved in DMF (0.5 mL) in a 1.5 mL plastic Eppendorf tube, to which DIPEA (50 mM in DMF, 0.5 mL) was added. The required fluoroheteroaromatic or fluoro-aromatic was added in 25 equivalents and the tube was shaken at room temperature for 4.5 h. After removal of volatiles under vacuum, each reaction mixture was redissolved in a 1:1 mixture of $H_2O$ and MeCN (1 mL) and analysed by LCMS (ESI+) and $^{19}F$ NMR (100 µL $D_2O$ added).

Procedure B

Solid peptide (approx. 2 mg, 2.5 µmol) was dissolved in DMF (0.5 mL) in a 1.5 mL plastic Eppendorf tube, to which DIPEA (50 mM in DMF, 0.5 mL) was added. The required fluoro-heteroaromatic or fluoro-aromatic was added in 5 equivalents and the tube was shaken at room temperature for 4.5 h. After removal of volatiles under vacuum, each reaction mixture was redissolved in a 1:1 mixture of $H_2O$ and MeCN (1 mL) and analysed by LCMS (ESI+) and $^{19}F$ NMR (100 µL $D_2O$ added).

Procedure C

Solid peptide (approx. 2 mg, 2.5 µmol) was dissolved in DMF (0.5 mL) in a 1.5 mL plastic Eppendorf tube, to which DIPEA (50 mM in DMF, 0.5 mL) was added. The required fluoro-heteroaromatic or fluoro-aromatic was added in 25 equivalents and the tube was shaken at 50° C. for 4.5 h. After removal of volatiles under vacuum, the solid was washed with DCM (2×1 mL) and the residual solid was redissolved in a 1:1 mixture of $H_2O$ and MeCN (1 mL) and analysed by LCMS (ESI+) and $^{19}F$ NMR (100 µL $D_2O$ added).

Procedure D

Solid peptide (approx. 2 mg, 2.5 µmol) was dissolved in TFE (0.5 mL) in a 1.5 mL plastic Eppendorf tube, to which DIPEA (so mM in TFE, 0.5 mL) was added. The required fluoro-heteroaromatic (or fluoro-aromatic) was added in 25 equivalents and the tube was shaken at room temperature for 4.5 h. After removal of volatiles under vacuum, each reaction mixture was redissolved in a 1:1 mixture of $H_2O$ and MeCN (1 mL) and analysed by LCMS (ESI+) and $^{19}F$ NMR (100 µL $D_2O$ added).

Procedure E

A stock solution of peptide was prepared by dissolving in the appropriate solvent (approx. 2 mg/mL). In a 2.0 mL glass vial peptide stock solution was added (1.0 mL), to which DIPEA (20 µL) was added. An aliquot of stock pentafluoropyridine solution (200 µL, 9.0 mM in the respective solvent) was added and the volume adjusted to a final volume of 2.0 mL by addition of appropriate solvent. The resulting mixture was shaken at room temperature for 4.5 h. After removal of volatiles under vacuum, each reaction mixture was redissolved in DMF/$D_2O$ (9:1, 1 mL) and analysed by LCMS (ESI+) and $^{19}F$ NMR.

Procedure F

A stock solution of peptide was prepared by dissolving in the appropriate solvent (approx. 2 mg/mL). In a 2.0 mL glass vial peptide stock solution was added (1.0 mL), to which DIPEA (20 µL) was added. An aliquot of stock pentafluoropyridine solution (70 µL, 9.0 mM in the respective solvent) was added and the volume adjusted to a final volume of 2.0 mL by addition of appropriate solvent. The resulting mixture was shaken at room temperature for 4.5 h. After removal of volatiles under vacuum, each reaction mixture was redissolved in DMF/$D_2O$ (9:1, 1 mL) and analysed by LCMS (ESI+) and $^{19}F$ NMR.

Procedure G

Solid peptide (approx. 2 mg, 2.5 µmol) was dissolved in DMF (4.5 mL) in a sealed glass vial, to which DIPEA (50 mM in DMF, 0.5 mL) was added. The required perfluoroheteroaromatic was added in 25 equivalents and the tube was shaken at room temperature for 4.5 h. After removal of volatiles under vacuum, each reaction mixture was redissolved in a 1:1 mixture of $H_2O$ and MeCN (1 mL) and analysed by LCMS (ESI+) and $^{19}F$ NMR (100 µL $D_2O$ added).

Procedure H

Solid peptide (approx. 2 mg, 2.5 µmol) was dissolved in the appropriate solvent (0.5 mL) in a 1.5 mL plastic Eppendorf tube, to which $Cs_2CO_3$ or DIPEA stock solutions (50 mM DMF, 0.5 mL) was added. The fluoro-aromatic or fluoro-heteroaromatic was then added (25 equivalents with respect to the peptide) and the tube was shaken at room temperature for 4.5 h. After removal of volatiles under vacuum, each reaction mixture was redissolved in a 8:1:1 mixture of DMF/$H_2O$/ACN-d3 (1 mL) and analysed by LCMS (ESI+) and 19F NMR. Large scale reactions for product isolation and purification were run under the same parameters in Ar flushed syringes, in order to avoid air bubbles where volatile aromatic compounds may concentrate.

Procedure I

Solid peptoid (approx. 2 mg, 2.5 µmol) was dissolved in DMF (0.5 mL) in a 1.5 mL plastic Eppendorf tube, to which DIPEA (50 mM in DMF, 0.5 mL) was added. The required fluoro-aromatic or fluoro-heteroaromatic was then added (25 equivalents with respect to the peptoid) and the tube was shaken at room temperature for 4.5 h. After removal of volatiles under vacuum, each reaction mixture was redissolved in a 1:1 mixture of $H_2O$ and MeCN (1 mL) and analysed by LC-MS (ESI+) and $^{19}F$ NMR. Due to the observation of N-terminal (Nae) mass loose in ESI+ mode, samples were also analysed by Maldi-ToF in order to confirm that fragmentation was induced by ionization and not by peptoid degradation. When LC-MS (ESI+) analysis was not possible due to poor solubility of the reaction products in $H_2O$/MeCN mixtures and/or molar mass of the expected products was beyond LC-MS (ESI+) range, analitycal HPLC with detection at 220 nm was used in order to obtain the reaction profile of products in DMF (95% $H_2O$ to 95% MeCN in 40 min, 1 mL/min) and Maldi-ToF analysis was employed to verify the mass of the final products present in the sample.

LC-MS Conditions:

Peptides and peptoids were characterised by LC-MS, ESI-LC MeCN (TQD mass spectrometer and an Acquity UPLC from Waters) using an Acquity UPLC BEH C8 1.7 µM (2.1 mm×50 mm) column and (C18 as of Jun. 2, 2015 3 pm) with a flow rate of 0.6 ml min$^{-1}$, a linear gradient of 5-95% of solvent B over 3.8 min (A=0.1% formic acid in $H_2O$, B=0.1% formic acid in MeCN) and injection volume of 1 µl.

QToF (mass spectrometer and an Acquity UPLC from Waters) using an Acquity UPLC BEH C8 1.7 µm (2.1 mm×50 mm) column with a flow rate of 0.6 ml min$^{-1}$, a linear gradient of 0-99% of solvent B over 5 min (A=0.1% formic acid in $H_2O$, B=0.1% formic acid in MeCN) and injection volume of 3 µl.

Peptides and peptoids identities were also confirmed by MALDI-TOF mass spectra analysis (Autoflex II ToF/ToF mass spectrometer Bruker Daltonik GmBH) operating in positive ion mode using an α-cyano-4-hydroxycinnamic acid (CHCA or CHHA) matrix. Data processing was done with MestReNova Version 10.0.

TQD

ESI-LC MeCN (TQD): Acquity UPLC BEH C8 1.7 µm (2.1 mm×50 mm) (C18 as of Jun. 2, 2915 3 pm)

Mobile phase: water containing formic acid (0.1% v/v): Acetonitrile

Flow rate: 0.6 ml min$^{-1}$

Injection volume: 1 µl

Gradient:

| Time (min) | % A | % B |
|---|---|---|
| 0 | 95 | 5 |
| 0.2 | 95 | 5 |
| 4 | 5 | 95 |
| 4.5 | 5 | 95 |
| 5 | 95 | 5 |

Data processing: MestReNova 10.0
QToF
Accurate mass: Acquity UPLC BEH C18 1.7 µm (2.1 mm×100 mm)
Mobile phase: water containing formic acid (0.1% v/v): Acetonitrile
Flow rate: 0.6 ml min$^{-1}$
Injection volume: 3 µl
Gradient:

| Time (min) | % A | % B |
|---|---|---|
| 0 | 100 | 0 |
| 5 | 1 | 99 |
| 6 | 1 | 99 |
| 6.1 | 100 | 0 |
| 7 | 100 | 0 |

Figure 11:
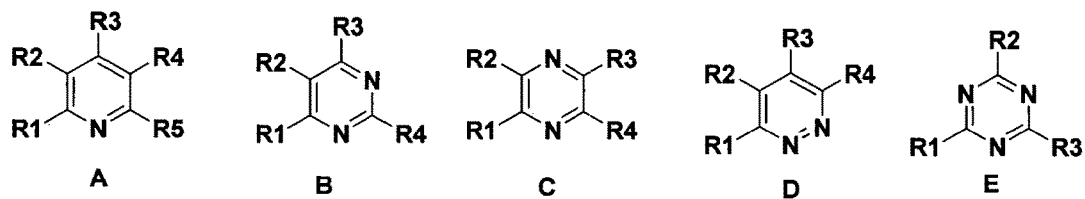
FIG. 11 shows the possible positions of nitrogen atoms in the fluoro-hereroaromatics which may be used in accordance with the present invention.

Data processing: MestReNova 10.0
MALDI
Autoflex II ToF/ToF mass spectrometer Bruker Daltonik GmBH 337 nm nitrogen laser
Sample preparation 1 mg/ml, 1 µl spotted on matrix
Operating in positive ion mode using an α-cyano-4-hydroxycinnamic acid (CHCA or HCCA) matrix
Data acquisition: reflecton mode of analysis
Data processing: MestReNova 10.0
The fluoro-heteroaromatic used in the reactions had to contain at least one nitrogen atom in the aromatic ring. However, it could contain two or three nitrogens in the aromatic ring. FIG. 11 shows five different heterocyclic ring systems which illustrate the possible positions of nitrogen atoms in the fluoro-heteroaromatic reagents. The fluorine atoms are not shown. However, it will be readily understood that for use in cyclisation reactions each ring must contain at least two halogen atoms, and at least one of the halogen atoms must be a fluorine atom.

Ring system A could therefore contain 2, 3, 4 or 5 halogen atoms, and 1, 2, 3, 4 or 5 fluorine atoms. Accordingly, it could be bifluoropyridine, trifluoropyridine, tetrafluoropyridine or pentafluoropyridine.

Similarly, ring systems B, C and D could contain 2, 3 or 4 halogen atoms, and 1, 2, 3, or 4 fluorine atoms, and ring system E could contain 2 or 3 halogen atoms, and 1, 2 or 3 flourine atoms.

Example 1

Tagging of Cysteine-Containing Peptides with Fluoro-Heteroaromatics

Peptide 1, was reacted according to procedures A and B. The reaction is shown below and the products for each reaction are shown in table 1.

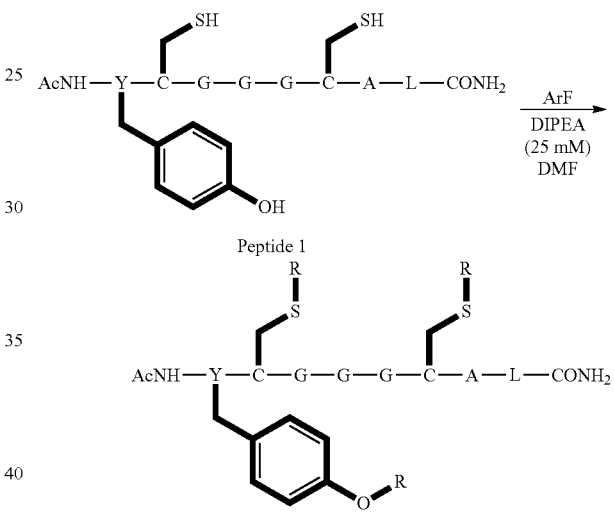

TABLE 1

Reaction of peptide 1 with pentafluoropyridine using procedures A and B

| Procedure | ArF | Products formed |
|---|---|---|
| A | | |

TABLE 1-continued

Reaction of peptide 1 with pentafluoropyridine using procedures A and B

| Procedure | ArF | Products formed |
|---|---|---|
| B | (pentafluoropyridine structure) | (peptide with two pyridyl-S substituents) AcNH—Y—C—G—G—G—C—A—L—CONH$_2$ with R group: a R = H, b R = (tetrafluoropyridyl) |

In the prior art hexafluorobenzene has been shown to react with peptide 1 to generate a cyclic peptide.[vi,vii] The introduction of nitrogen atom into the aromatic ring increases the reactivity of the perfluoroaromatic systems considerably as pentafluorpyridine and its derivatives are significantly more reactive than hexafluorobenzene. Therefore, pentafluorpyridine reacted with peptide 1 to give a multiply tagged peptide rather than a cyclic product, as explained below. Interestingly reports of sulphur nucleophiles reacting with pentafluoropyridine are not well documented in the literature.

Figure 12:
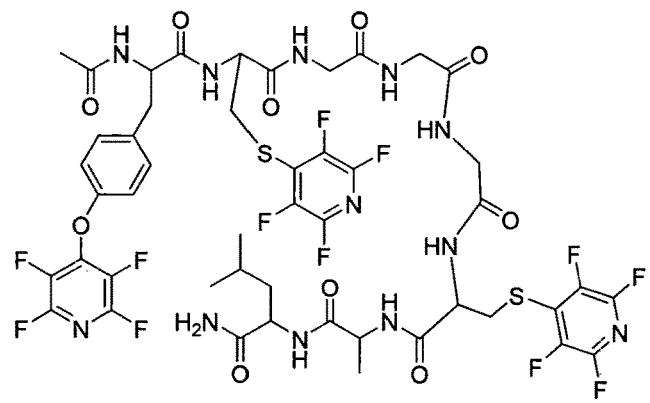
FIG. 12 shows the structure, chemical formula and molecular weight of a product formed by reacting peptide 1 with pentafluoropyridine according to procedure A or B.
Figure 13:
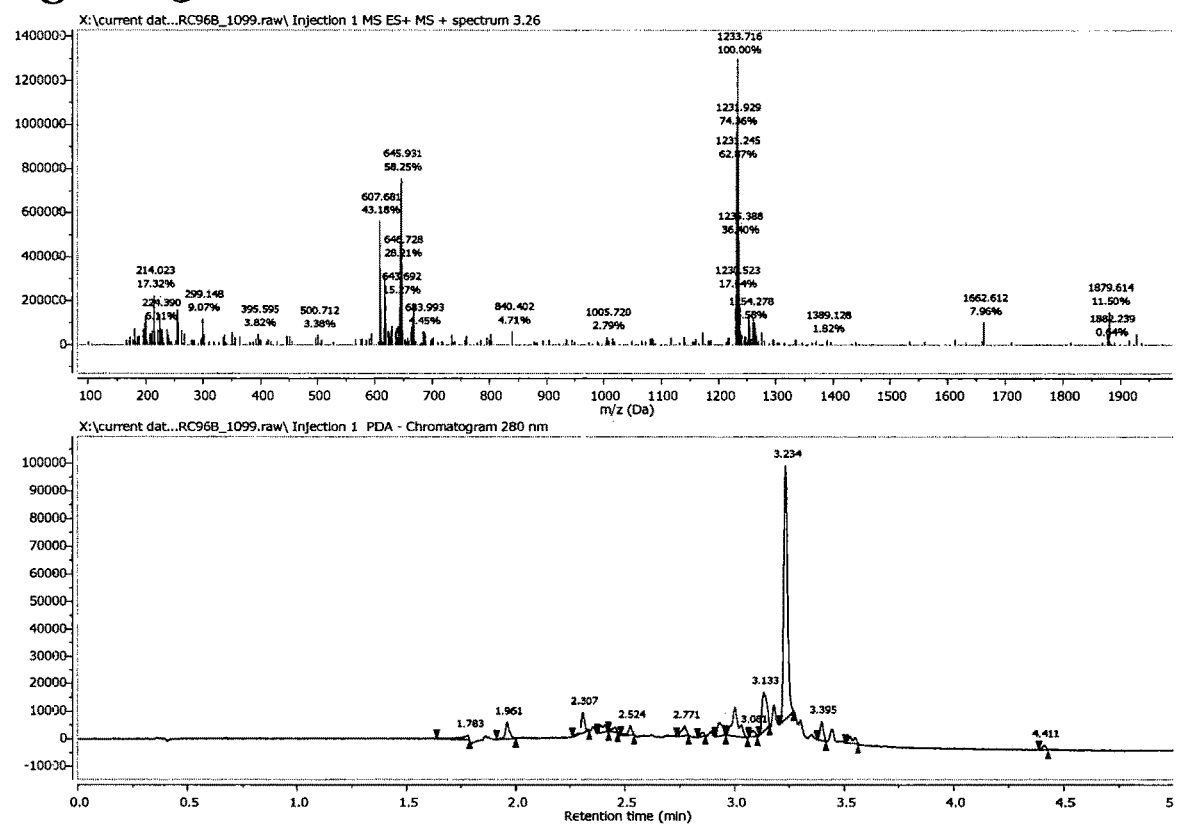
FIG. 13 is an LCMS spectrum and chromatogram at 280 nm for the products formed by reacting peptide 1 with pentafluoropyridine according to procedure A.

The crude reaction products were analysed used LCMS. The LCMS spectrum and chromatogram of the reaction of peptide 1 according to procedure A is shown in FIG. 13. This shows one major peak in the LCMS chromatogram with a retention time of 3.234 minutes. The spectrum for this peak shows an [M+H]$^+$ peak at 1231.929 m/z, which indicates a tri-substituted product was formed. The structure of this product is shown in FIG. 12.

Figure 16:
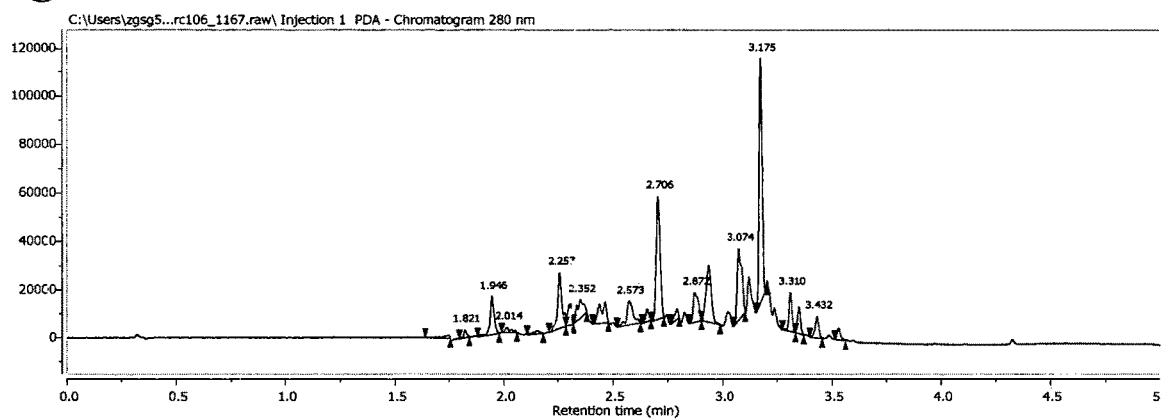
FIG. 16 is an LCMS chromatogram at 280 nm of the products formed by reacting peptide 1 according to procedure B.

The LCMS chromatogram of the reaction of peptide 1 according to procedure B is shown in FIG. 16. This shows three major peaks in the LCMS chromatogram with retention times of 1.946, 2.706, 3.074 and 3.175 minutes. Analysis of these peaks was carried out and the results are summarised in table 2.

TABLE 2

Products of the reaction of peptide 1 according to procedure B identified using LCMS spectroscopy

| Peak | Retention time | m/z | Identity |
|---|---|---|---|
| 1 | 1.946 | 820 | Starting peptide MeCN adduct |
| 2 | 2.706 | 1082 | Double ArF addition |

TABLE 2-continued

Products of the reaction of peptide 1 according to procedure B identified using LCMS spectroscopy

| Peak | Retention time | m/z | Identity |
|---|---|---|---|
| 3 | 3.074 | 1138 | ? |
| 4 | 3.175 | 1231 | Triple ArF addition |

This shows that both bi-substituted and tri-substituted products were formed.

Owing to the presence of fluorine atoms in the reagents, it was possible to monitor in situ the outcome of these reactions rapidly using $^{19}$F NMR spectra. Moreover, fluorine is very sensitive to changes in local environment, which made it possible to gain structural details which include the substitution pattern around the ring and number of fluoro-heteroaryl groups that have been added.

Figure 14:
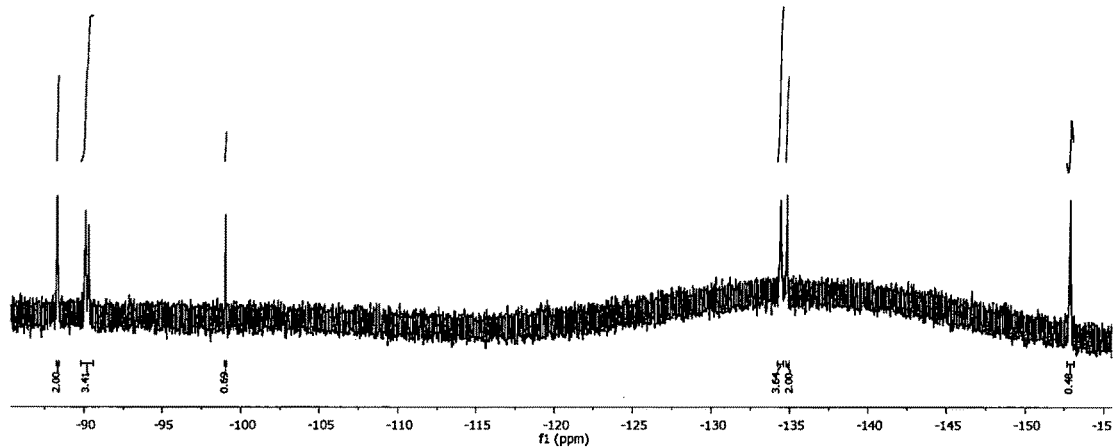
FIG. 14 is a $^{19}$F NMR spectrum for the products formed by reacting peptide 1 according to procedure A, with the solvent used for the NMR being H$_2$O/MeCN/D$_2$O in a ratio of 1:1:0.2.
Figure 15:
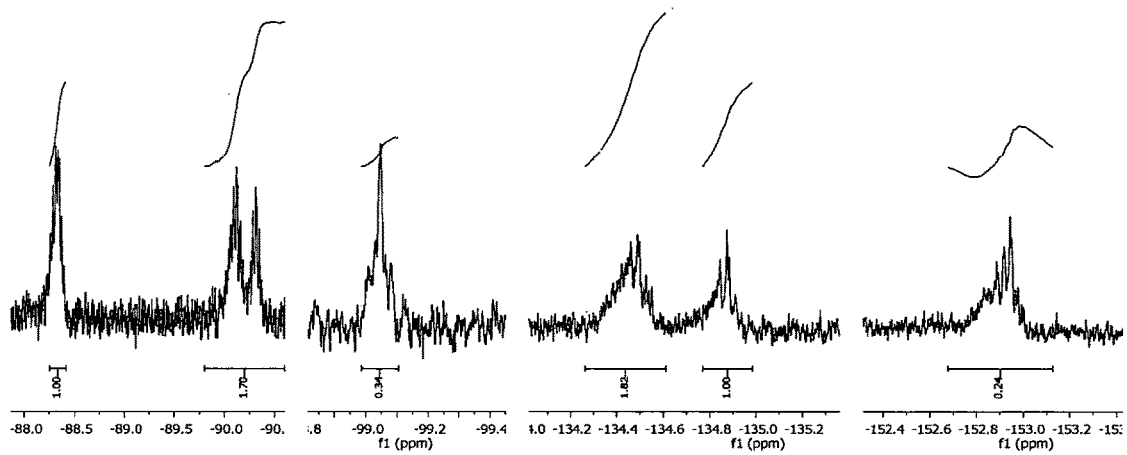
FIG. 15 shows the expansions of the peaks of the spectrum of FIG. 14.

FIG. 14 shows the $^{19}$F NMR spectrum of the products of reaction of peptide 1 according to procedure A and FIG. 15 shows expansions of the peaks. The spectrum shows six different peaks which is consistent with the six different fluorine environments you would expect for a tri-substituted product.

Peptide 1, was reacted according to procedure A with either a fluoro-heteroaromatic (I-VII) or a fluoro-aromatic (VIII). The chemical structures for each of the various fluoro-heteroaromatics (I-VII) or fluoro-aromatic (VIII) are shown in table 3. The crude reaction products for the reactions were analysed using LCMS, and the results are also shown in table 3.

TABLE 3

Reaction of peptide 1 with various fluoro-heteroaromatics (I-VII) or fluoro-aromatic (VIII) reagents using procedure A

Figure 17:
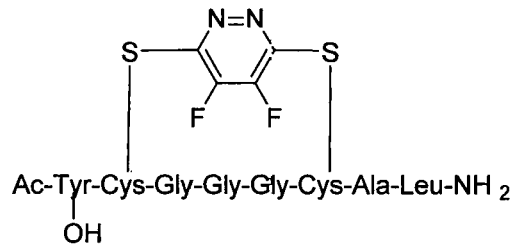
FIG. 17 shows the structure for the product formed by reacting peptide 1 with fluoro-heteroaromatic (I) according to procedure A.
Figure 18:
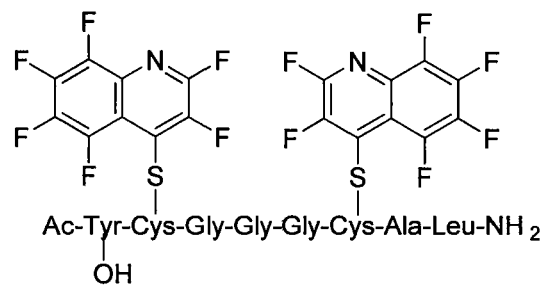
FIG. 18 shows the structure for the product formed by reacting peptide 1 with fluoro-hereroaromatic (III) according to procedure A.
Figure 19:
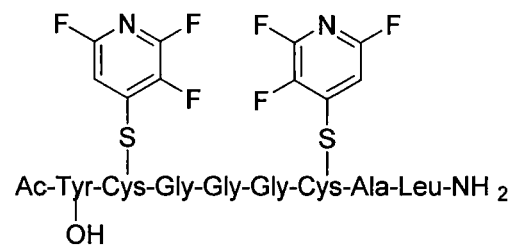
FIG. 19 shows the structure for the product formed by reacting peptide 1 with fluoro-heteroaromatic (IV) according to procedure A.
Figure 20:
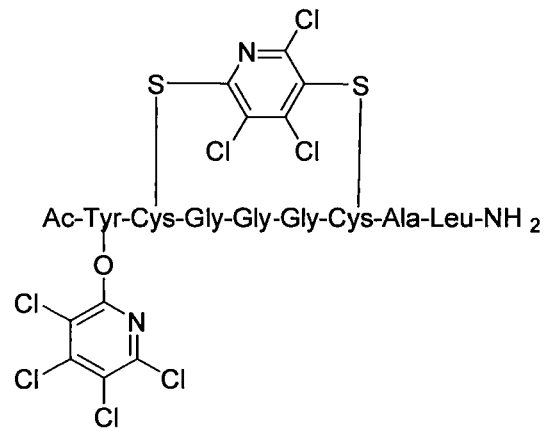
FIG. 20 shows the structure for the products formed by reacting peptide 1 with fluoro-heteroaromatic (V) according to procedure A.
Figure 21:
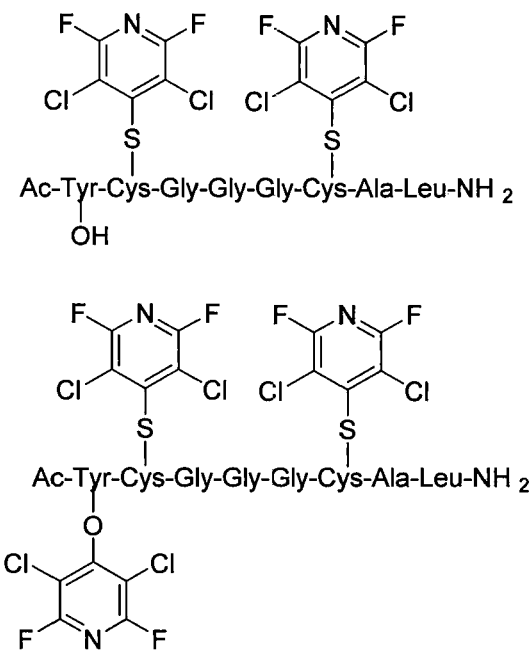
FIG. 21 shows the structure for the products formed by reacting peptide 1 with fluoro-heteroaromatic (VI) according to procedure A.

| Entry | ArF | LCMS spectrum and chromatogram | Products |
|---|---|---|---|
| 1 | 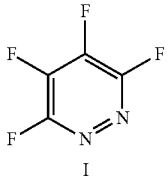<br>I | One major peak in the LCMS chromatogram with a retention time of 2.472 minutes, the spectrum for this peak shows an $[M + H]^+$ peak at 1027.676 m/z. | Cyclic product, see FIG. 17. |
| 2 | 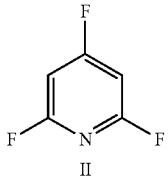<br>II | One major peak in the LCMS chromatogram with a retention time of 1.942 minutes, the spectrum for this peak shows an $[M + H]^+$ peak which corresponds to starting peptide 1. | No detectable new products. |
| 3 | 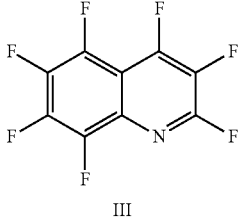<br>III | One major peak in the LCMS chromatogram with a retention time of 3.104 minutes, the spectrum for this peak shows an $[M + H]^+$ peak at 1255.52 m/z. | Di-substituted product, see FIG. 18. |
| 4 | 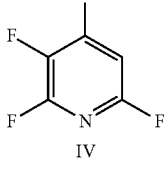<br>IV | One major peak in the LCMS chromatogram with a retention time of 2.665 minutes, the spectrum for this peak shows an $[M + H]^+$ peak at 1045.674 m/z. | Di-substituted product, see FIG. 19. |
| 5 | 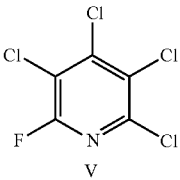<br>V | A major peak in the LCMS chromatogram with a retention time of 3.071 minutes, the spectrum for this peak shows an $[M + H]^+$ peak at 1231.929 m/z. | Cyclic mono-substituted product, see FIG. 20. |
| 6 | 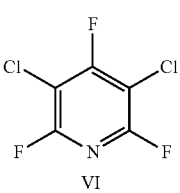<br>VI | Two major peaks in the LCMS chromatogram with retention times of 2.950 minutes and 3.394 minutes. The spectrum for these peaks show an $[M + H]^+$ peak at 1203.590 m/z and $[M + H]^+$ peak at 1328.009 m/z respectively. | Di-substituted and the tri-substituted products were formed, see FIG. 21. |

TABLE 3-continued

Reaction of peptide 1 with various fluoro-heteroaromatics (I-VII) or fluoro-aromatic (VIII) reagents using procedure A

Figure 22:
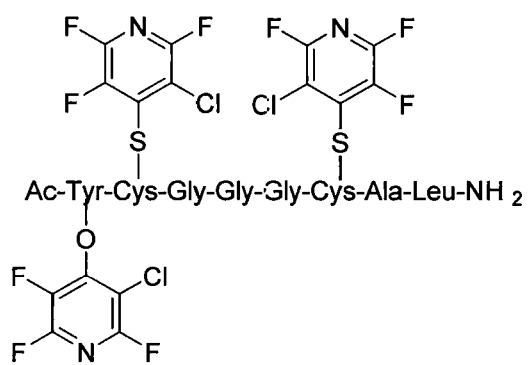
FIG. 22 shows the structure for the products formed by reacting peptide 1 with fluoro-heteroaromatic (VII) according to procedure A.
Figure 23:
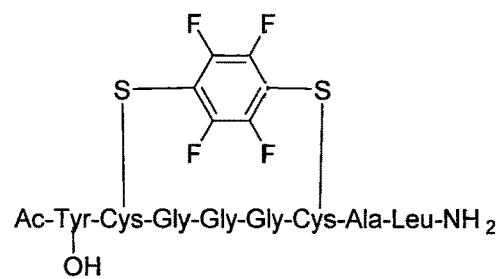
FIG. 23 shows the structure for the products formed by reacting peptide 1 with fluoro-aromatic (VIII) according to procedure A.

| Entry | ArF | LCMS spectrum and chromatogram | Products |
|---|---|---|---|
| 7 | 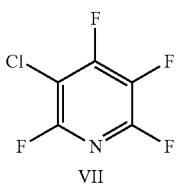<br>VII | A major peak in the LCMS chromatogram with a retention times 3.180 minutes, the spectrum for this peaks shows an [M + H]$^+$ peak at 1280.062 m/z. | Tri-substituted product, see FIG. 22. |
| 8 | 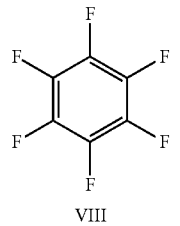<br>VIII | One major peak in the LCMS chromatogram with a retention time of 2.265 minutes, the spectrum for this peak shows an [M + H]$^+$ peak at 929.874 m/z. | Cyclic product see FIG. 23. |

As mentioned previously, in the prior art hexafluorobenzene was found to readily react with peptides containing two cysteine residues to generate a cyclic peptide. Accordingly, the result obtained for entry 8 of table 3 is consistent with the teachings of the prior aft.

Example 2

Reaction of Glutathione with Pentafluoropyridine

Peptide 5, was reacted according to procedure E. The reaction is shown below. This shows a single mono-substituted product was formed.

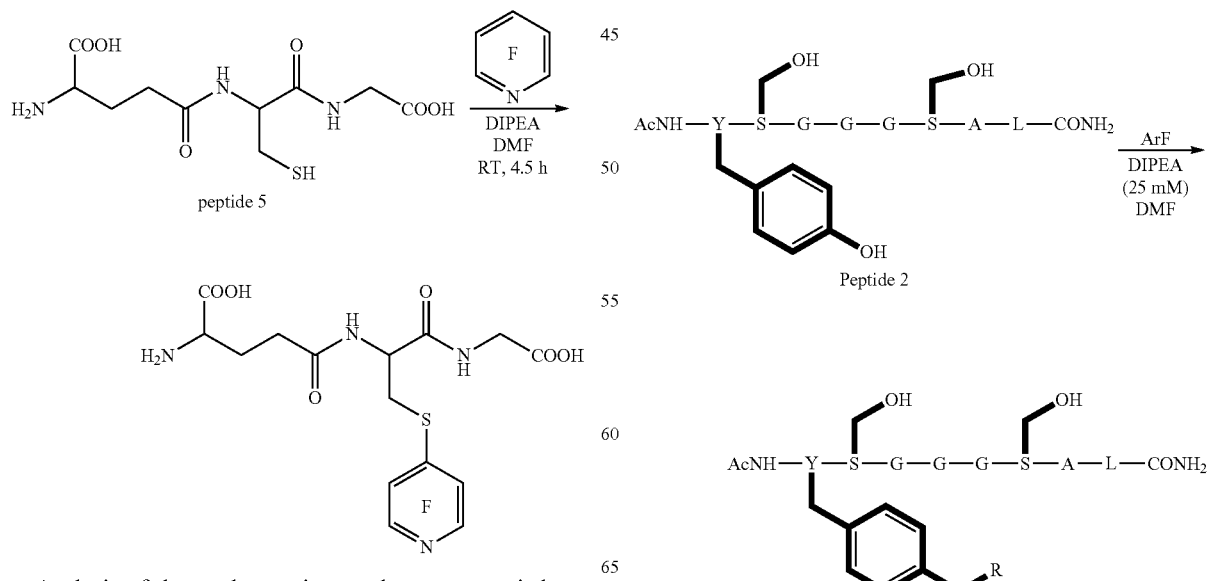

Figure 24:
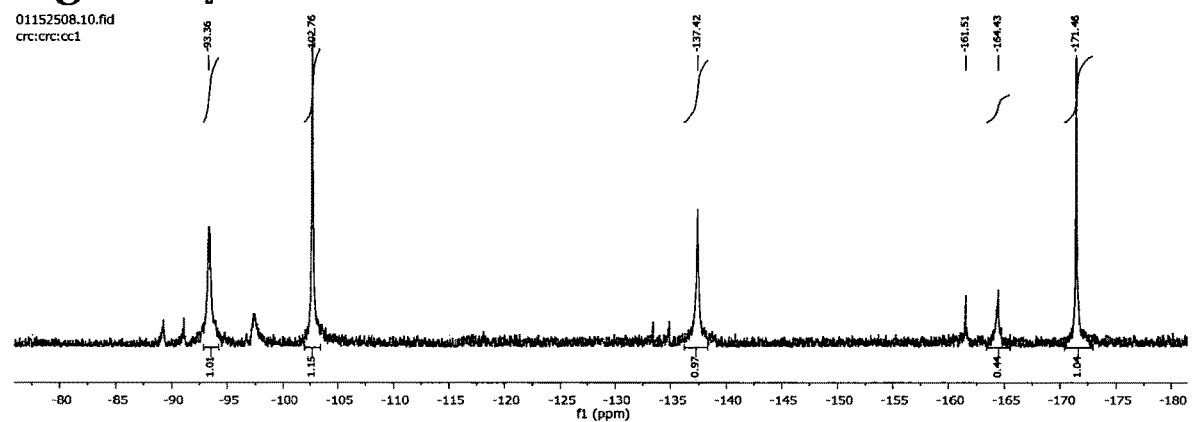
FIG. 24 is a crude $^{19}$F NMR spectrum for the products formed by reacting peptide 5 according to procedure F.

Analysis of the crude reaction products was carried out using $^{19}$F NMR spectroscopy, and the spectrum is shown in FIG. 24. Residual pentafluoropyridine is seen at −93.36, −137.42 and −164.43 ppm. However, the peaks at −102.76 and −171.46 ppm relate to the tagged peptide and are consistent with a single, mono-substituted product.

Example 3

Tagging of Tyrosine-Containing Peptides with Fluoro-Heteroaromatics

Peptide 2, was reacted according to procedures A and C. The reaction is shown below and the products for each reaction are shown in table 4.

TABLE 4

Reaction of peptide 2 with perfluoro-heteroaromtics using procedures A and C

| Procedure | ArF | Products formed |
|---|---|---|
| A | pentafluoropyridine | AcNH—Y—S(—CH₂OH)—G—G—G—S(—CH₂OH)—A—L—CONH₂, with tyrosine O-linked to tetrafluoropyridyl group |
| C | pentafluoropyridine | AcNH—Y—S(—CH₂OH)—G—G—G—S(—CH₂OH)—A—L—CONH₂, with tyrosine O-linked to tetrafluoropyridyl group |

At room temperature pentafluoropyridine was found to only react with the phenolic OH on the tyrosine (Y) residue.

Figure 25:
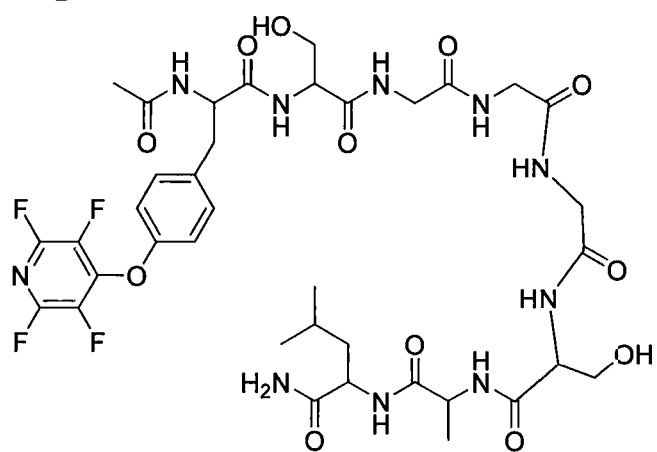
FIG. 25 shows the structure, chemical formula and molecular weight of a product formed by reacting peptide 2 according to procedure A or C.

The crude reaction products were analysed used LCMS. The LCMS spectrum and chromatogram of the reaction of peptide 2 according to procedure A shows one major peak in the LCMS chromatogram with a retention time of 2.455 minutes. The spectrum for this peak shows an [M+H]⁺ peak at 900.688 m/z, which indicates a mono-substituted product was formed. The structure of this product is shown in FIG. 25.

Similarly, the LCMS spectrum and chromatogram of the reaction of peptide 2 according to procedure C shows one major peak in the LCMS chromatogram with a retention time of 2.261 minutes. The spectrum for this peak shows an [M+H]⁺ peak at 900.358 m/z, which also indicates a mono-substituted product was formed.

Figure 26:
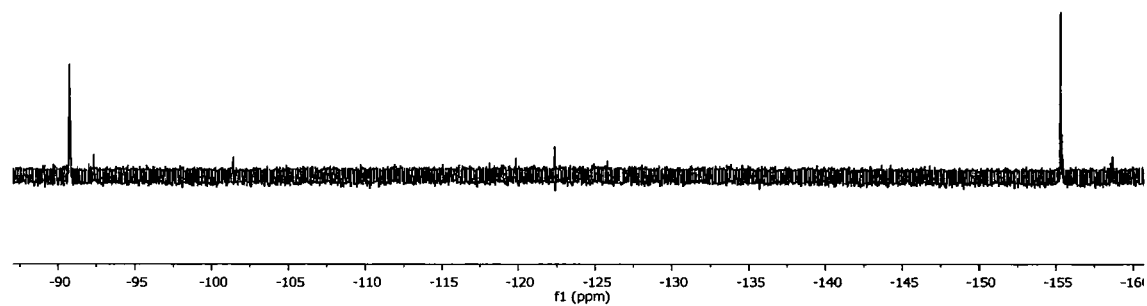
FIG. 26 is a $^{19}$F NMR spectrum for the products formed by reacting peptide 2 according to procedure A, with the solvent used for the NMR being H$_2$O/MeCN/D$_2$O in a ratio of 1:1:0.2.
Figure 27:
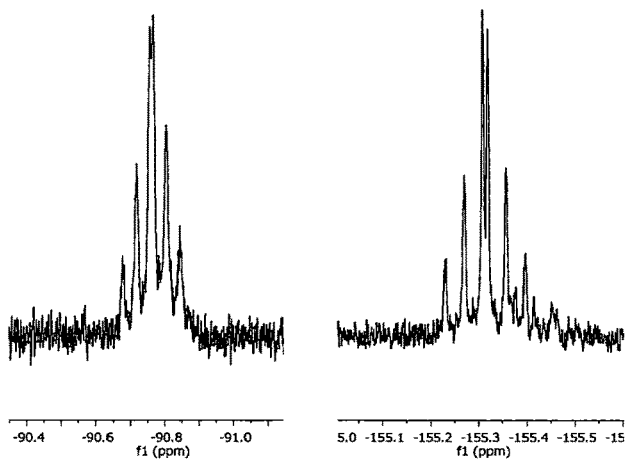
FIG. 27 shows the expansions of the peaks of the spectrum of FIG. 26.

Again $^{19}F$ NMR spectroscopy was used to analysis the results. FIG. 26 shows the $^{19}F$ NMR spectrum of the products of reaction of peptide 2 according to procedure A and FIG. 27 shows expansions of the peaks. The spectrum shows two different peaks which is consistent with the two different fluorine environments you would expect for a mono-substituted product.

Example 4

Tagging of Serine-Containing Peptides with Fluoro-Heteroaromatics

Peptide 2, was reacted according to procedure A with either a fluoro-heteroaromatic (I-VII) or a fluoro-aromatic (VIII). The chemical structures for each of the various fluoro-heteroaromatics (I-VII) or fluoro-aromatic (VIII) are shown in table 5. The crude reaction products for the reactions were analysed using LCMS, and the results are also shown in table 3.

TABLE 5

Reaction of peptide 2 with various fluoro-heteroaromatics (I-VII) or fluoro-aromatic (VIII) reagents using procedure A.

Figure 28:
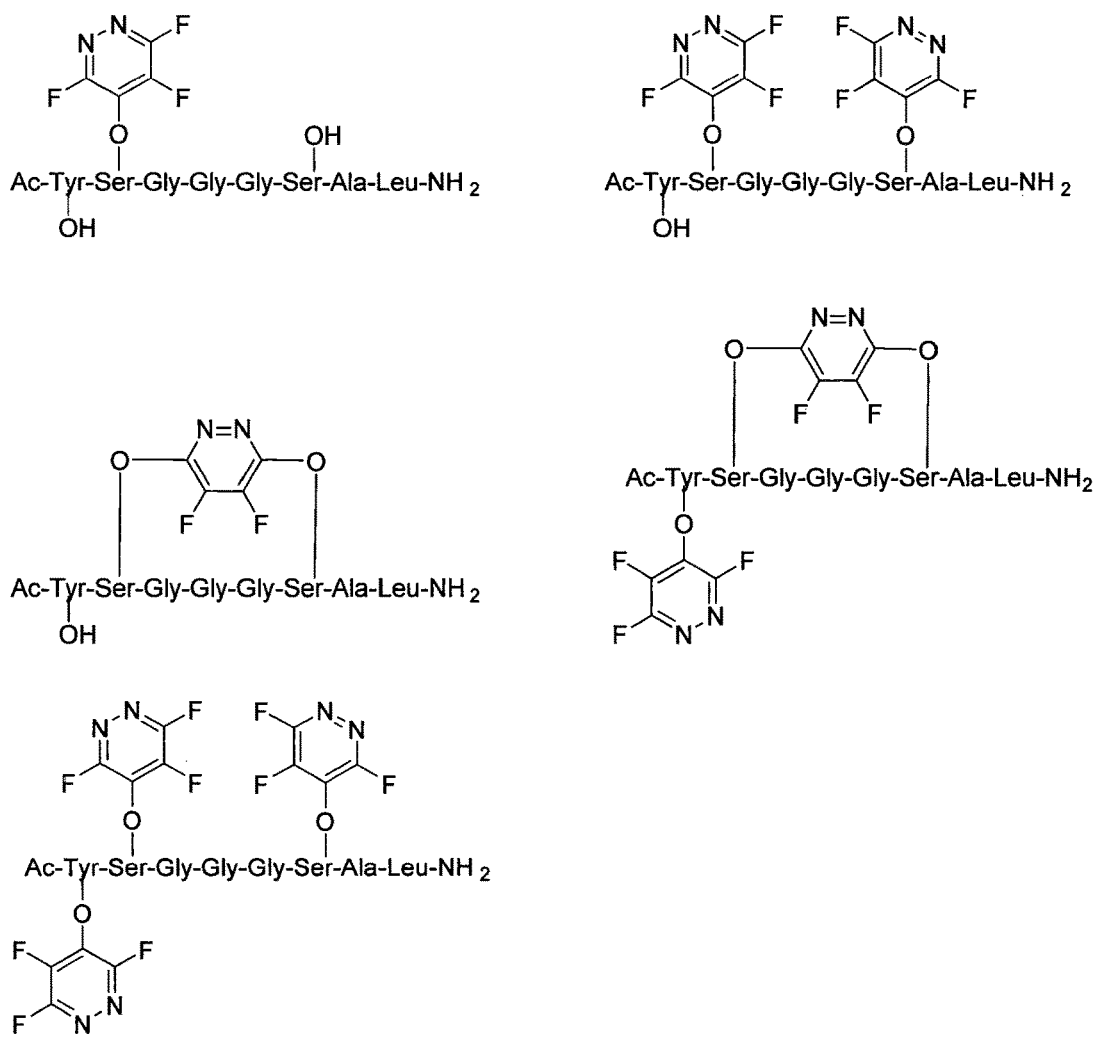
FIG. 28 shows the structure for the products formed by reacting peptide 2 with fluoro-heteroaromatic (I) according to procedure A.

| Entry | ArF | LCMS spectrum and chromatogram | Products |
|---|---|---|---|
| 1 | tetrafluoropyridazine (I) | Four major peak in the LCMS chromatogram with retention times of 2.625 minutes, 2.763 minutes, 2.818 minutes and 2.946 minutes. The spectrum for the peak at 2.625 minutes shows an [M + H]⁺ peak at 883.918 m/z. The spectrum for | Mono-substituted, di-substituted, tri-substituted and cyclic products, see FIG. 28. |

TABLE 5-continued

Reaction of peptide 2 with various fluoro-heteroaromatics (I-VII) or fluoro-aromatic (VIII) reagents using procedure A.

Figure 29:
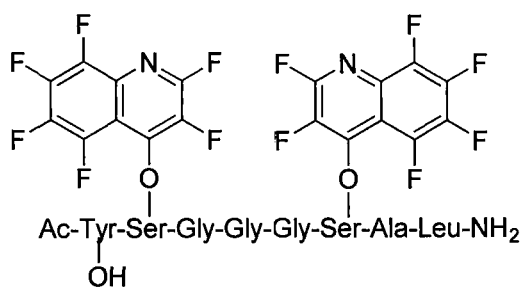
FIG. 29 shows the structure for the products formed by reacting peptide 2 with fluoro-heteroaromatic (III) according to procedure A.
Figure 30:
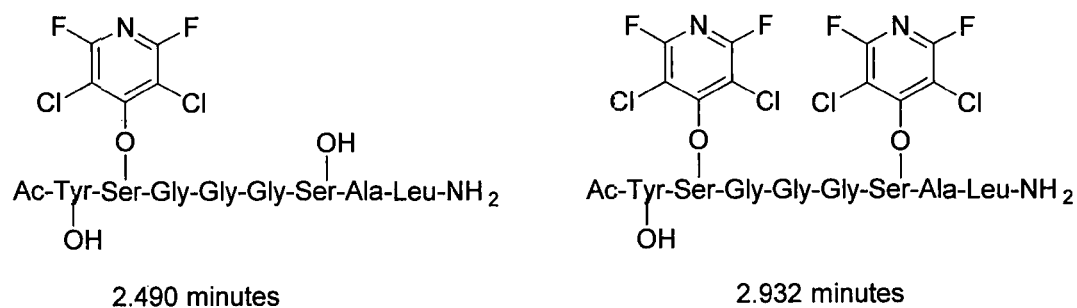
FIG. 30 shows the structure for the products formed by reacting peptide 2 with fluoro-heteroaromatic (VI) according to procedure A.
Figure 31:
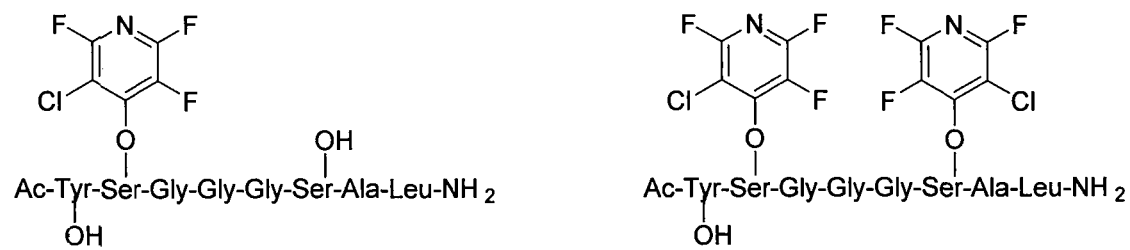
FIG. 31 shows the structure for the products formed by reacting peptide 2 with fluoro-hereroaromatic (VII) according to procedure A.

| Entry | ArF | LCMS spectrum and chromatogram | Products |
|---|---|---|---|
|  |  | the peak at 2.763 minutes shows an [M + H]+ peak at 995.921 m/z. The spectrum for the peak at 2.818 minutes shows an [M + H]+ peak at 1015.805 m/z. The spectrum for the peak at 2.946 minutes shows an [M + H]+ peak at 1148.058 m/z. |  |
| 2 | II (2,4,6-trifluoropyridine) | One major peak in the LCMS chromatogram with a retention time of 1.828 minutes, the spectrum for this peak shows an [M + H]+ peak at 753.132 m/z. | Unreacted peptide 2 detected. |
| 3 | III (pentafluoroquinoline) | One major peak in the LCMS chromatogram with a retention time of 3.007 minutes, the spectrum for this peak shows an [M + H]+ peak at 1221.554 m/z. | Di-substituted product, see FIG. 29. |
| 4 | IV (pentafluoropyridine) | One major peak in the LCMS chromatogram with a retention time of 1.842 minutes, the spectrum for this peak shows an [M + H]+ peak at 752.061 m/z. | Unreacted peptide 2 detected. |
| 5 | V (pentachloropyridine with F) | One major peak in the LCMS chromatogram with a retention time of 3.1 minutes. | Structure of this product could not be assigned. |
| 6 | VI | Two major peaks in the LCMS chromatogram with retention times of 2.490 minutes and 2.931 minutes. The spectrum for these peaks show an [M + H]+ peak at 932.907 m/z, and an [M + H]+ peak 1115.768 m/z. | Mono-substituted and the di-substituted products were formed, see FIG. 30. |
| 7 | VII | Two major peaks in the LCMS chromatogram with a retention times of 2.426 minutes and 2.758 minutes. The spectrum for these peaks show an [M + H]+ peak at 916.777 m/z, and an [M + H]+ peak at 1081.649 m/z. | Mono-substituted and the di-substituted products were formed, see FIG. 31. |

TABLE 5-continued

Reaction of peptide 2 with various fluoro-heteroaromatics (I-VII) or fluoro-aromatic (VIII) reagents using procedure A.

| Entry | ArF | LCMS spectrum and chromatogram | Products |
|---|---|---|---|
| 8 | 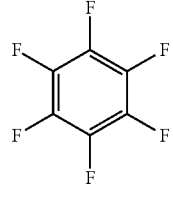 VIII | One major peak in the LCMS chromatogram with a retention time of 1.810 minutes, the spectrum for this peak shows an [M + H]+ peak at 752.026 m/z. | Unreacted peptide 2 detected. |

While hexafluorobenzene (VIII) was found to readily react with peptides containing two cysteine residues to generate a cyclic peptide, it was found to be completely unreactive towards nucleophilic attack by serine or tyrosine.

Example 5

Tagging of Lysine-Containing Peptides with Fluoro-Heteroaromatics

Peptide 3, was reacted according to procedures A and C. The reaction is shown below and the products for each reaction are shown in table 6.

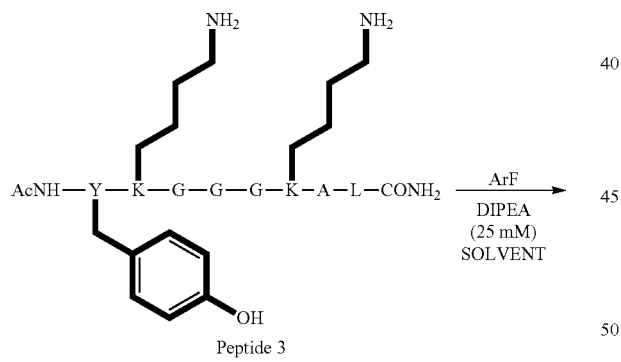
Peptide 3

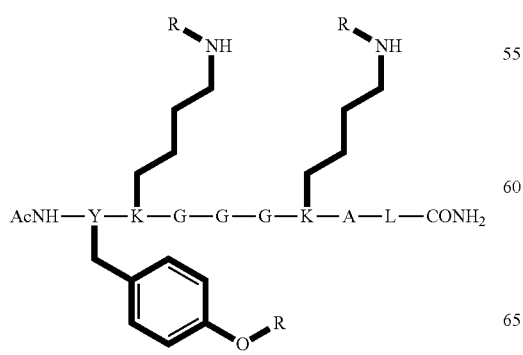

TABLE 6

Reaction of peptide 3 with perfluoro-heteroaromatics using procedures A and C

| Procedure | ArF | Products formed |
|---|---|---|
| A | 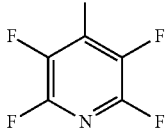 | 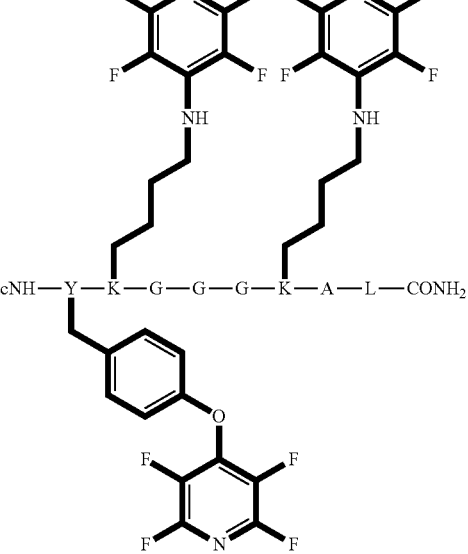 |
| C | 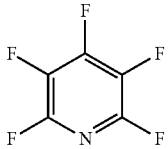 | 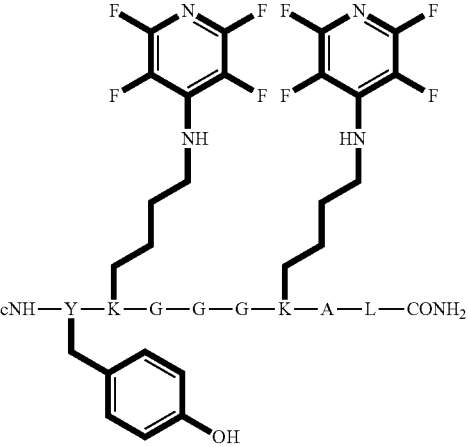 |

Figure 32:
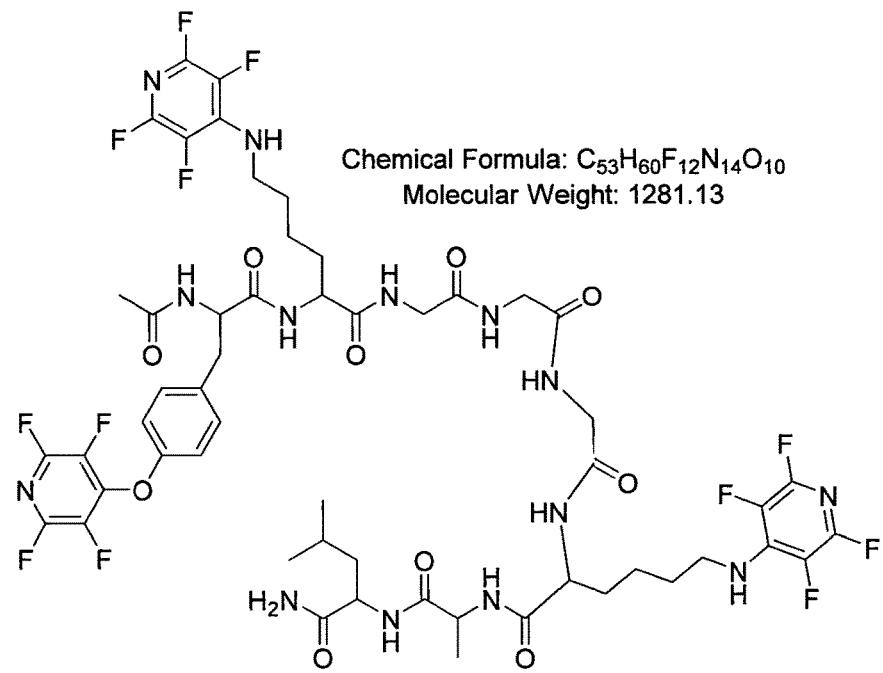
FIG. 32 shows the structure, chemical formula and molecular weight of a product formed by reacting peptide 3 according to procedure A.

The crude reaction products were analysed used LCMS. The LCMS spectrum and chromatogram of the reaction of peptide 3 according to procedure A shows one major peak in the LCMS chromatogram with a retention time of 3.209 minutes. The spectrum for this peak shows an [M+H]$^+$ peak at 1281.571 m/z, which indicates a tri-substituted product was formed. The structure of this product is shown in FIG. 32.

Figure 33:
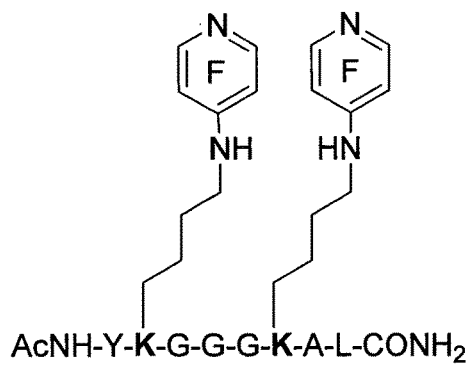
FIG. 33 shows the structure of a product formed by reacting peptide 3 according to procedure C.

However, the LCMS spectrum and chromatogram of the reaction of peptide 3 according to procedure C is shows one major peak in the LCMS chromatogram with a retention time of 3.086 minutes. The spectrum for this peak shows an [M+H]$^+$ peak at 1131.913 m/z, which indicates a bi-substituted product was formed. The structure of this product is shown in FIG. 33.

Peptide 3, was reacted according to procedure A with either a fluoro-heteroaromatic (I-VII) or a fluoro-aromatic (VIII). The chemical structures for each of the various fluoro-heteroaromatics (I-VII) or fluoro-aromatic (VIII) are shown in table 7.

TABLE 7

Reaction of peptide 3 with various fluoro-heteroaromatics (I-VII) or fluoro-aromatic (VIII) reagents using procedure A.

Figure 34:
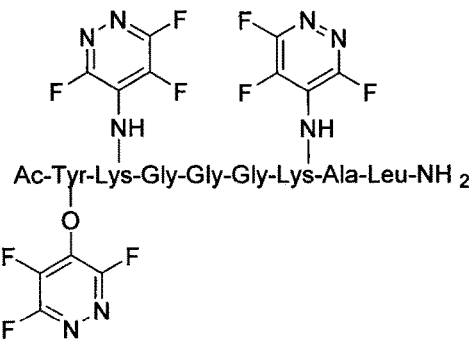
FIG. 34 shows the structure for the products formed by reacting peptide 3 with fluoro-heteroaromatic (I) according to procedure A.
Figure 35:
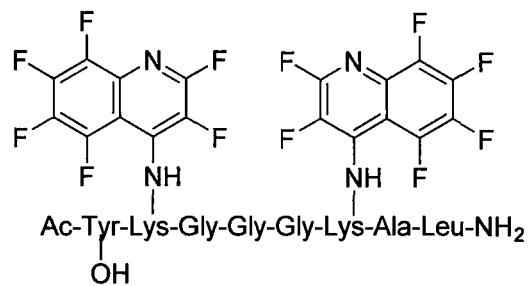
FIG. 35 shows the structure for the products formed by reacting peptide 3 with fluoro-heteroaromatic (III) according to procedure A.
Figure 36:
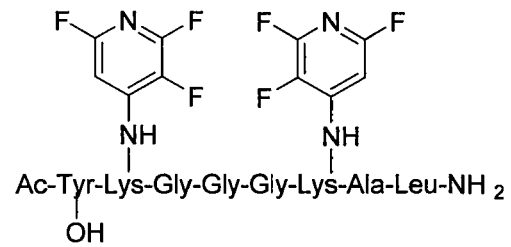
FIG. 36 shows the structure for the products formed by reacting peptide 3 with fluoro-heteroaromatic (IV) according to procedure A.
Figure 37:
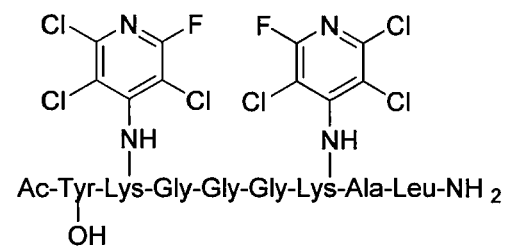
FIG. 37 shows the structure for the products formed by reacting peptide 3 with fluoro-heteroaromatic (V) according to procedure A.
Figure 38:
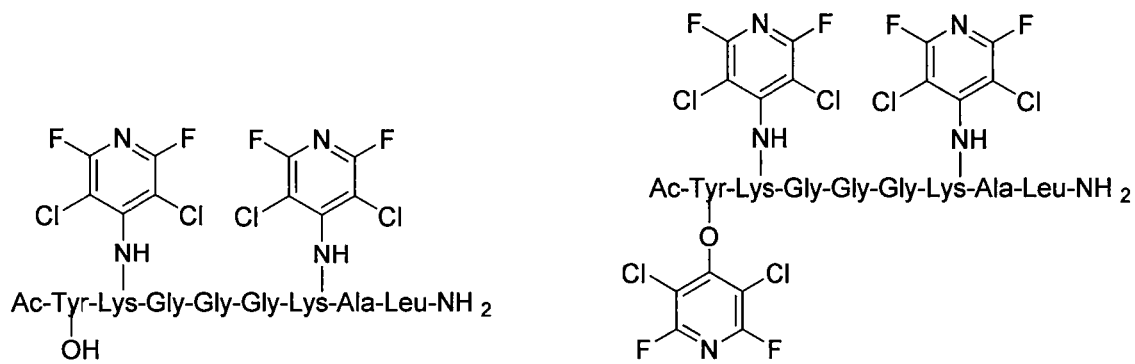
FIG. 38 shows the structure for the products formed by reacting peptide 3 with fluoro-heteroaromatic (VI) according to procedure A.
Figure 39:
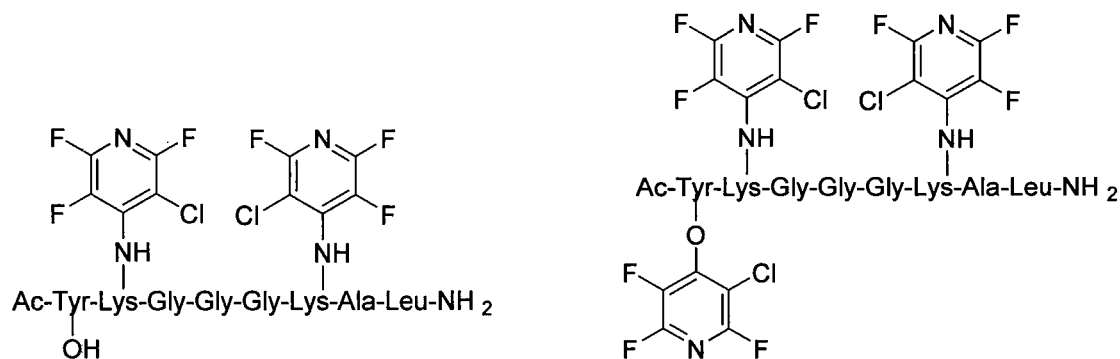
FIG. 39 shows the structure for the products formed by reacting peptide 3 with fluoro-heteroaromatic (VII) according to procedure A.

| Entry | ArF | LCMS spectrum and chromatogram | Products |
|---|---|---|---|
| 1 | 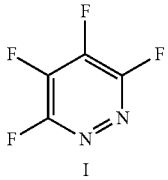<br>I | One major peak in the LCMS chromatogram with a retention time of 2.608 minutes, the spectrum for this peak shows an [M + H]$^+$ peak at 1229.630 m/z. | Tri-substituted product, see FIG. 34. |
| 2 | 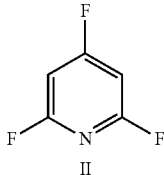<br>II | Three major peaks in the LCMS chromatogram. | Structure of these products could not be assigned. |
| 3 | 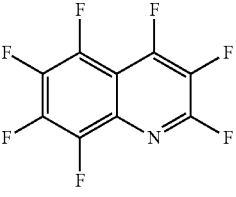<br>III | One major peak in the LCMS chromatogram with a retention time of 3.115 minutes, the spectrum for this peak shows an [M + H]$^+$ peak at 1303.728 m/z. | Di-substituted product, see FIG. 35. |
| 4 | 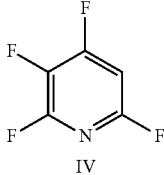<br>IV | One major peak in the LCMS chromatogram with a retention time of 2.659 minutes, the spectrum for this peak shows an [M + H]$^+$ peak at 1086.348 m/z. | Di-substituted product, see FIG. 36. |
| 5 | 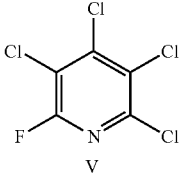<br>V | This shows one major peak in the LCMS chromatogram with a retention time of 3.261 minutes, the spectrum for this peak shows an [M + H]$^+$ peak at 1263.562 m/z. | Di-substituted product, see FIG. 37. |
| 6 | 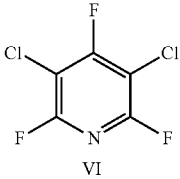<br>VI | Two major peaks in the LCMS chromatogram with retention times of 2.874 minutes and 3.343 minutes. The spectrum for these peak shows an [M + H]$^+$ peak at 1197.389 m/z and an [M + H]$^+$ peak at 1378.105 m/z. | Di-substituted and tri-substituted products, see FIG. 38. |
| 7 | 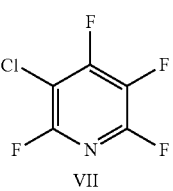<br>VII | This shows two major peaks in the LCMS chromatogram with retention times of 2.807 minutes and 3.245 minutes. The spectrum for these peak shows an [M + H]$^+$ peak at 1165.693 m/z, and an [M + H]$^+$ peak at 11328.587 m/z. | Di-substituted and tri-substituted products, see FIG. 39. |

TABLE 7-continued

Reaction of peptide 3 with various fluoro-heteroaromatics (I-VII) or fluoro-aromatic (VIII) reagents using procedure A.

| Entry | ArF | LCMS spectrum and chromatogram | Products |
|---|---|---|---|
| 8 | 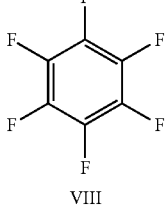 VIII | One major peak in the LCMS chromatogram with a retention time of 1.680 minutes. This peak corresponds to unreacted peptide 3. | Unreacted peptide 3 detected. |

While, hexafluorobenzene (VIII) will readily react with peptides containing two cysteine residues it was found to be completely unreactive towards nucleophilic attack by lysine.

Example 6

Effective on Cysteine, Lysine and Serine Tagging Using Fluoro-Heteroaromatics or Fluoro-Aromatics in the Presence of Organic or Inorganic Bases

Peptides 1-3, were reacted according to procedure H, where the solvent used was DMF and the base used was caesium carbonate. A reaction scheme is shown below, although the products obtained varied, as shown in table 8.

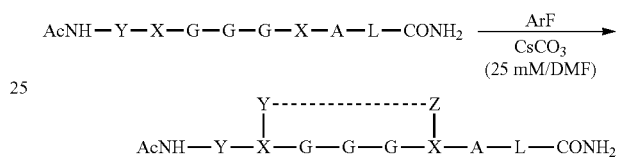

TABLE 8

Summary of the reactions of peptides 1-3 carried according to reaction procedure H where the base used was caesium carbonate.

Figure 62:
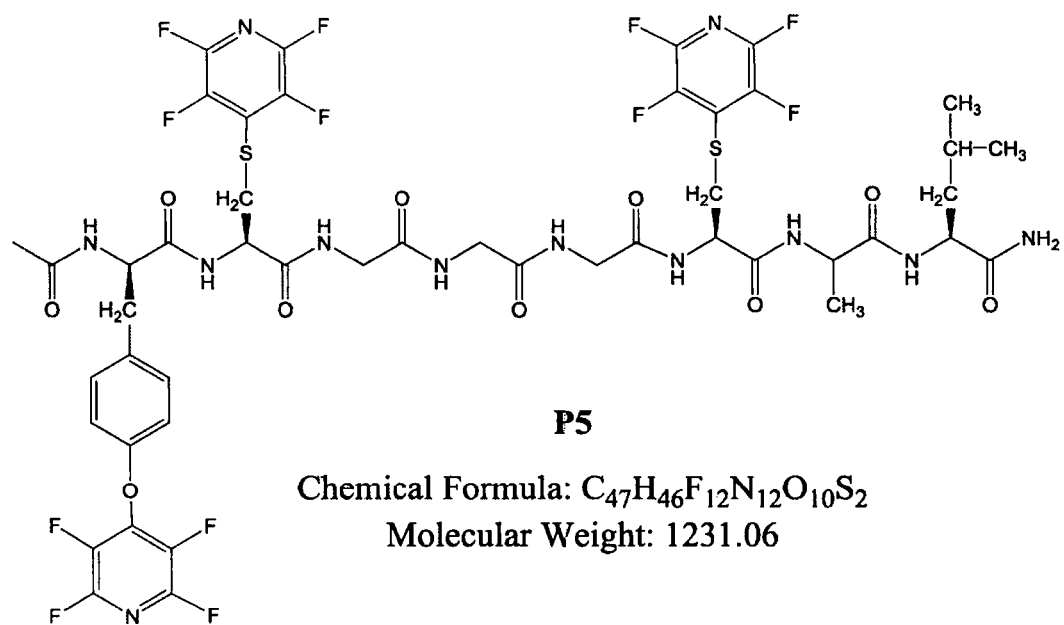
Figure 63:
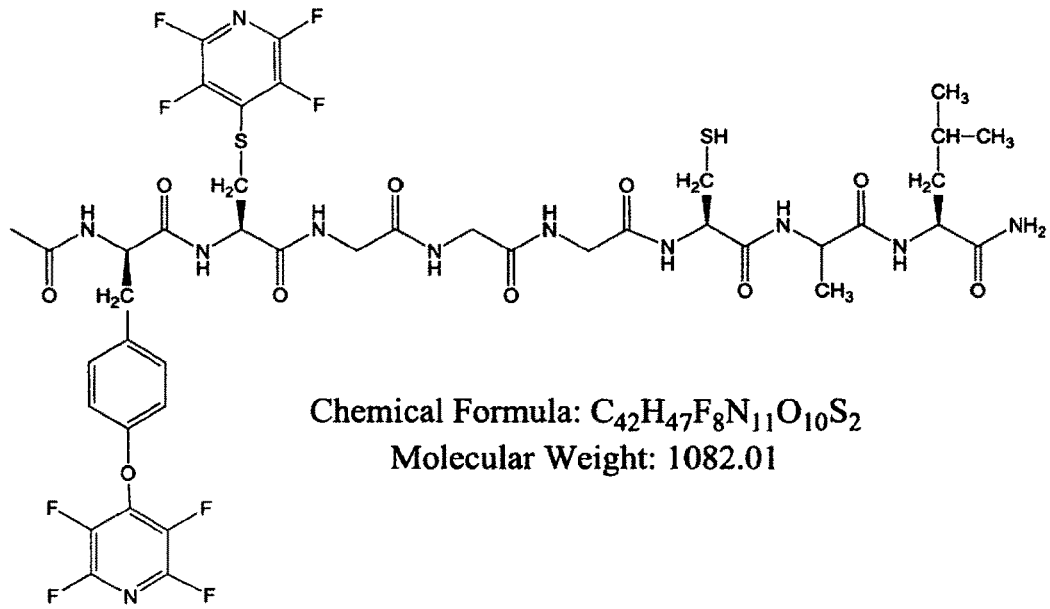
FIG. 63 shows the chemical structure for products P6a and P6b.
Figure 63:
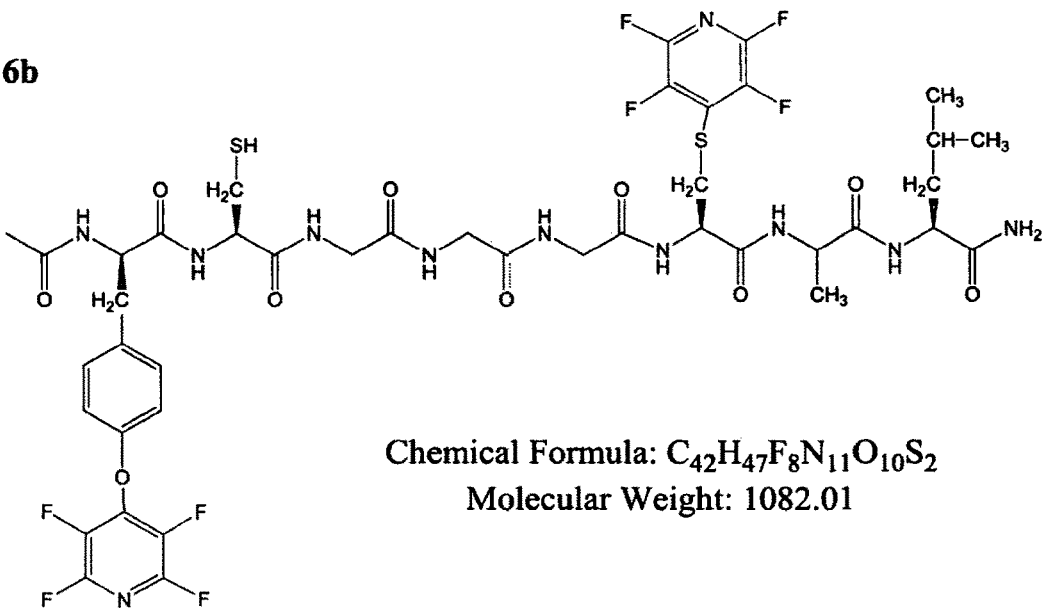
Figure 64:
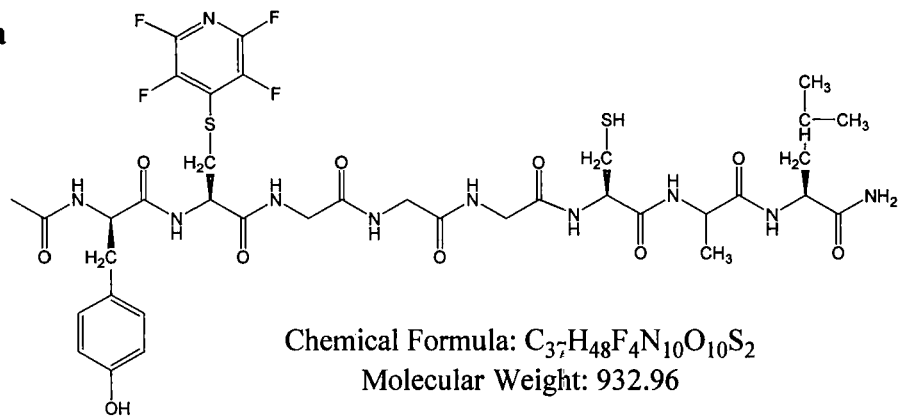
FIG. 64 shows the chemical structure for products P7a and P7b.
Figure 64:
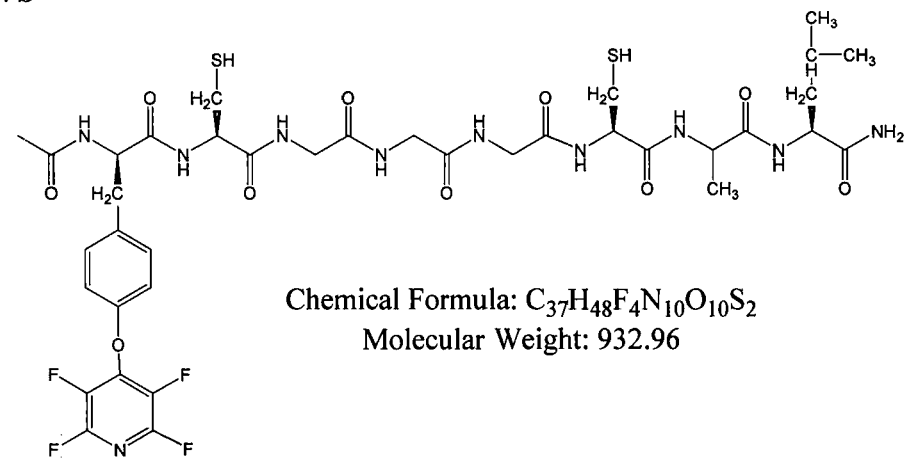
Figure 65:
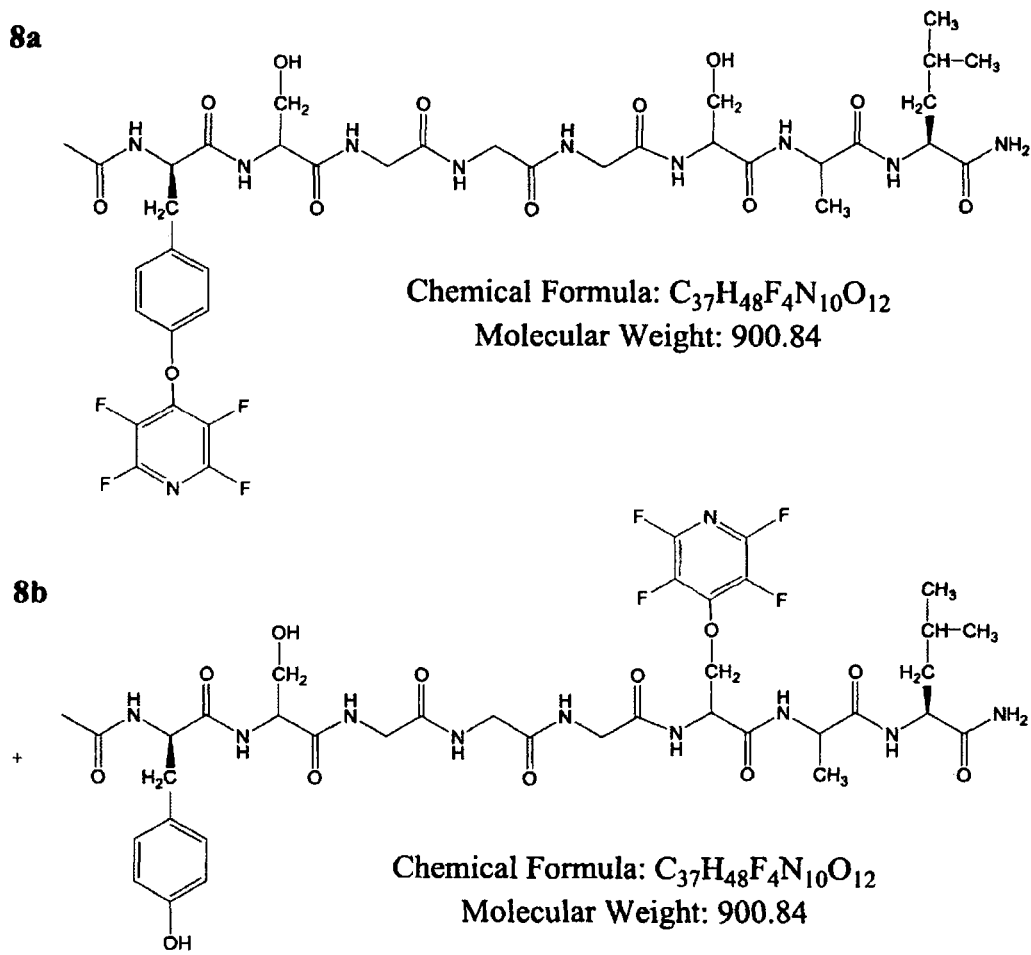
FIG. 65 shows the chemical structure for products P8a and P8b.
Figure 66:
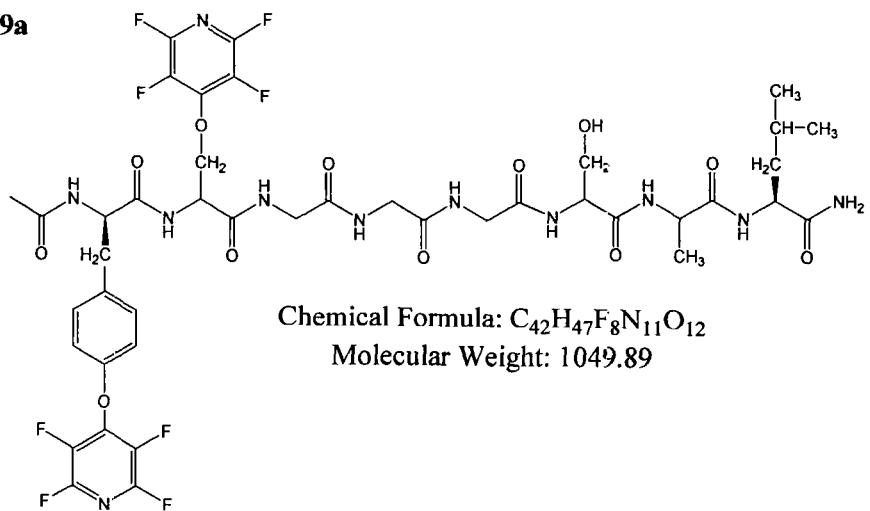
FIG. 66 shows the chemical structure for products P9a and P9b.
Figure 66:
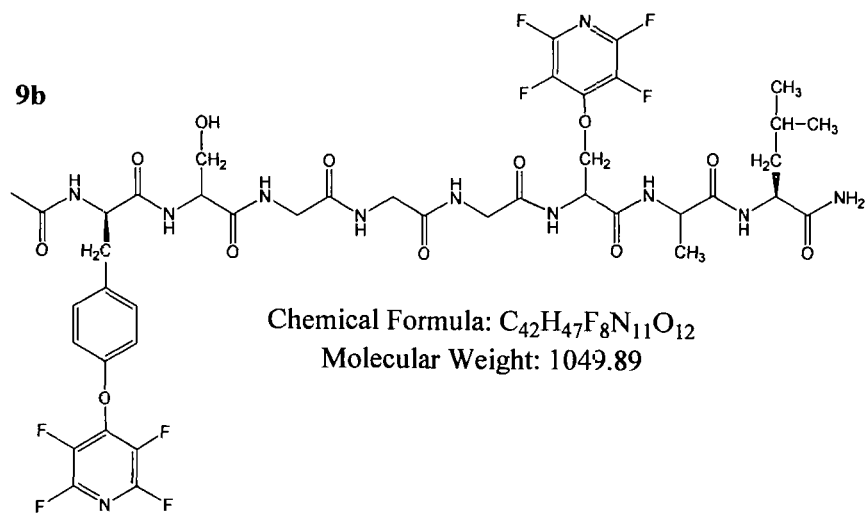
Figure 67:
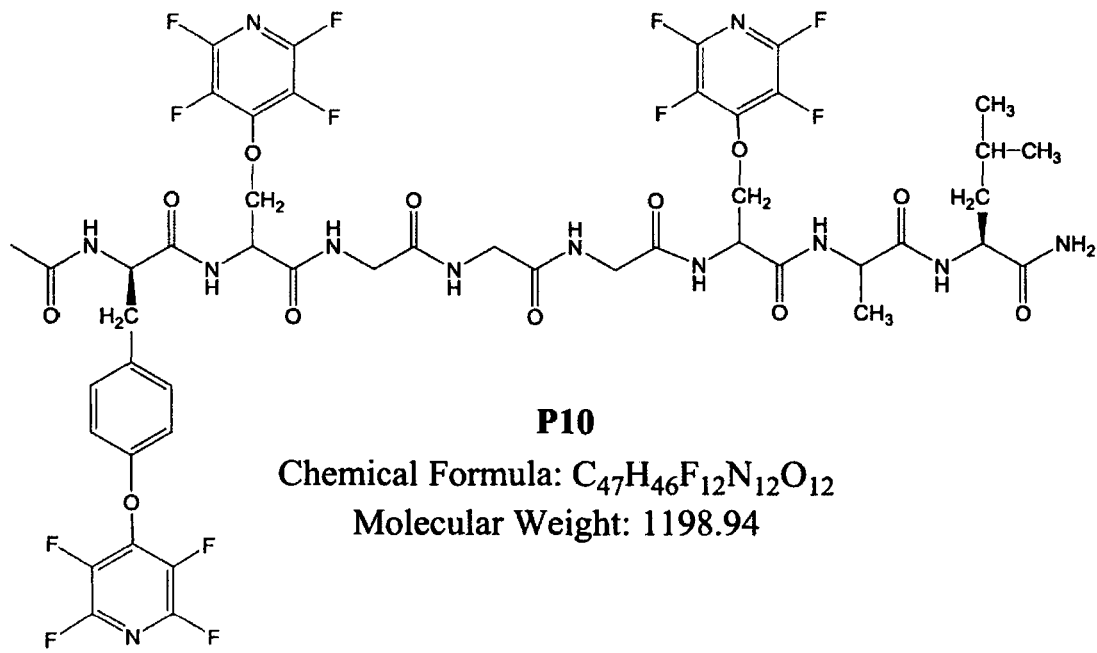
FIG. 67 shows the chemical structure for product P10.
Figure 68:
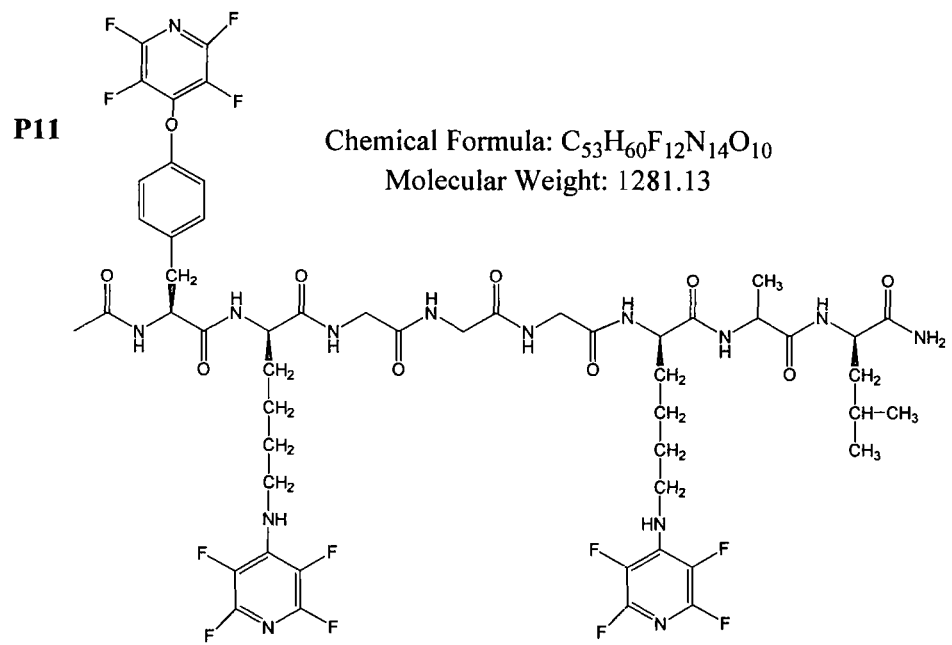
FIG. 68 shows the chemical structure for product P11.

| Entry | ArF | Peptide | Products | Position | $[m/z]_{obs}$ (Da) | Product |
|---|---|---|---|---|---|---|
| R1.4 | 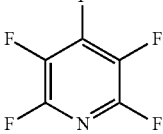 | 1, X = Cys | Tri-substituted (main) | 2Cys and Tyr | 1231.28 | P5, see FIG. 62 |
| | | | Di-substituted (minor) | Cys and Tyr | 1138.35 | P6a and P6b, see FIG. 63 |
| | | | Mono-substituted (minor) | Cys/Tyr mixture | 1048.3 | P7a and P7b, see FIG. 64 |
| R1.5 | 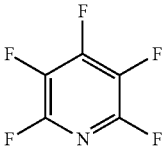 | 2, X = Ser | Mono-substituted | Tyr/Ser mixture | 901.34 | P8a and P8b, see FIG. 65 |
| | | | Di-substituted | Tyr and Ser | 1050.34 | P9a and P9b, see FIG. 66 |
| | | | Tri-substituted | 2 Ser and Tyr | 1199.33 | P10, see FIG. 67 |
| R1.6 | 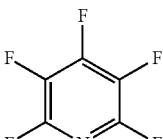 | 3, X = Lys | Tri-substituted | 2Lys and Tyr | 1281.45 | P11, see FIG. 68 |

Peptides 1-3, were reacted according to procedure H, where the solvent used was DMF and the base used was N,N-diisopropylethylamine (DIPEA). A reaction scheme is shown below, although the products obtained varied, as shown in table 9.

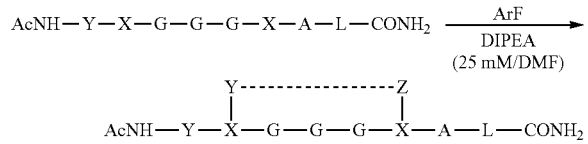

TABLE 9

Summary of tagging reactions of peptides 1-3 carried out according to reaction procedure H where the base used was DIPEA.

Figure 69:
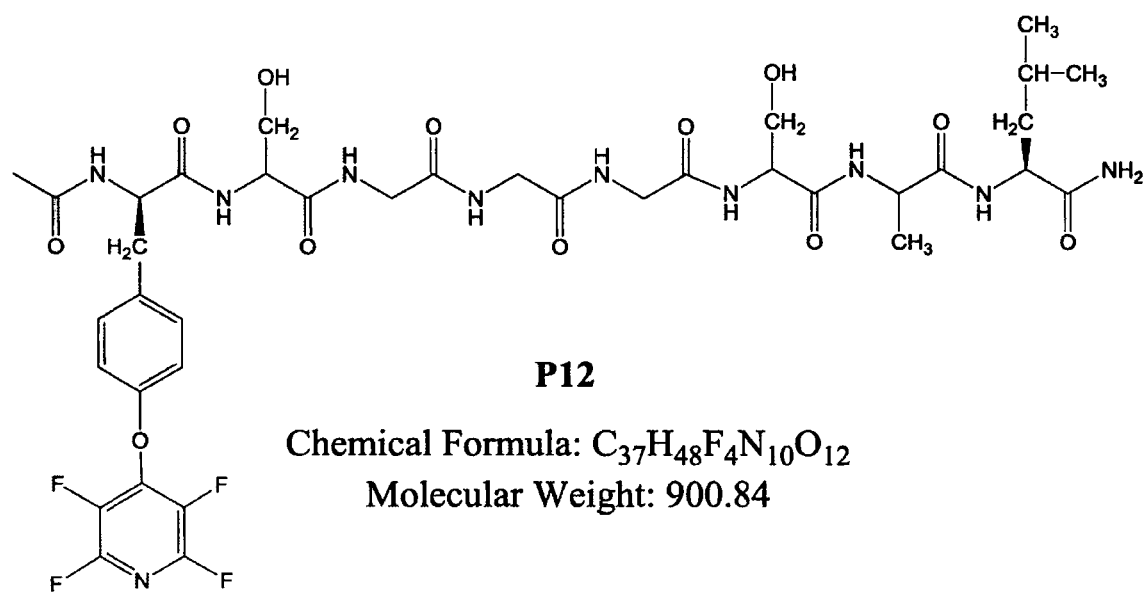
FIG. 69 shows the chemical structure for product P12.

| Entry | ArF | Peptide | Products | Position | $[m/z]_{obs}$ (Da) | Product |
|---|---|---|---|---|---|---|
| R2.4 |  | 1, X = Cys | Tri-substituted | 2Cys and Tyr | 1233.7 | P5, see FIG. 62 |
| R2.5 | 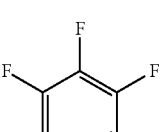 | 2, X = Ser | Mono-substituted | Tyr | 901.35 | P12, see FIG. 69 |
| R2.6 | 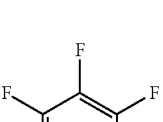 | 3, X = Lys | Tri-substituted | 2Lys and Tyr | 1281.45 | P11, see FIG. 68 |

It will be noted that there are clear differences in the products obtained depending on the base used.

For example;

DIPEA provides less of a mixture of products. This is evident when comparing entries R1.4 (table 8) and R2.4 (table 9). Here it can be seen that when the reaction of peptide 1 and pentafluoropyridine is carried out using DIPEA as the base (R2.4, table 9) only one main product is formed. When the analogous reaction is carried out with caesium carbonate as the base (R1.4, table 8) three products were observed and isolated.

Example 7

Selective Cysteine Tagging Using Fluoroheteroaromatics in the Presence of Tyrosine Employing 2,2,2-trifluoroethanol (TFE) as Solvent Peptide 1, was reacted according to procedure D. The reaction is shown below and the product for the reaction is shown in table 10.

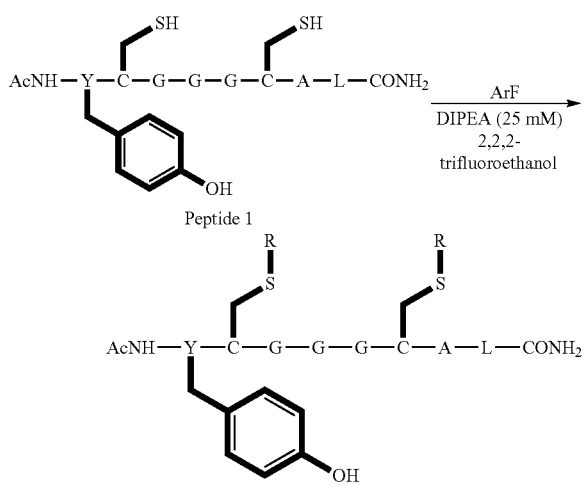

TABLE 10

Reaction of peptide 1 with fluoro-heteroaromatics using Procedure D

| Procedure | Stapling reagent | Comments/Products formed |
|---|---|---|
| D | 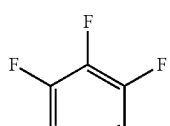 | 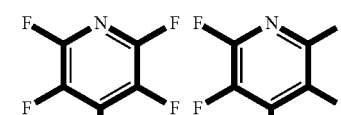 |

Figure 40:
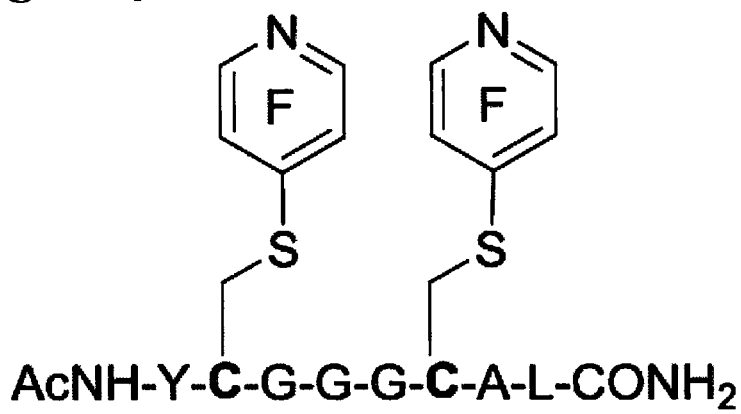
FIG. 40 shows the structure of a product formed by reacting peptide 1 according to procedure D.

The crude reaction products were analysed used LCMS. The LCMS spectrum and chromatogram of the reaction of peptide 1 according to procedure D shows one major peak in the LCMS chromatogram with a retention time of 2.617 minutes. The spectrum for this peak shows an [M+H]$^+$ peak at 1081.629 m/z, which indicates a bi-substituted product was formed. The structure of this product is shown in FIG. 40.

Peptides 1-3 were reacted with both hexafluorobenzene and pentafluoropyridine according to procedure D. A reaction scheme is shown below, although the products obtained varied, as shown in table 11.

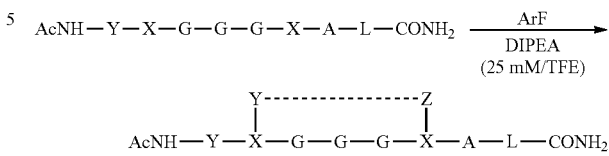

TABLE 11

Reaction of peptides 1-3 with hexafluorobenzene and pentafluoropyridine according to procedure D.

| Entry | ArF | Peptide | Products | Position | [m/z]$_{obs}$ (Da) | Product |
|---|---|---|---|---|---|---|
| 1 | hexafluorobenzene | 1, X = Cys | No reaction | — | — | — |
| 2 | hexafluorobenzene | 2, X = Ser | No reaction | — | — | — |
| 3 | hexafluorobenzene | 3, X = Lys | No reaction | — | — | — |
| 4 | pentafluoropyridine | 1, X = Cys | Mono-substituted | Cys | 989.36 | P7a |
|   |   |   | Di-substituted | 2Cys | 1038.29 | P14 |
| 5 | pentafluoropyridine | 2, X = Ser | No reaction | — | — | — |
| 6 | pentafluoropyridine | 3, X = Lys | No reaction | — | — | — |

The crude reaction products were analysed used LCMS.

The reaction of peptides 1-3 with hexafluorobenezne according to procedure D did not yield any products (table 11, entries 1-3). Similarly, the reaction of peptides 2 and 3 with pentafluoropyridine according to procedure D also did not yield any products (table 11, entries 5 and 6).

Figure 41:
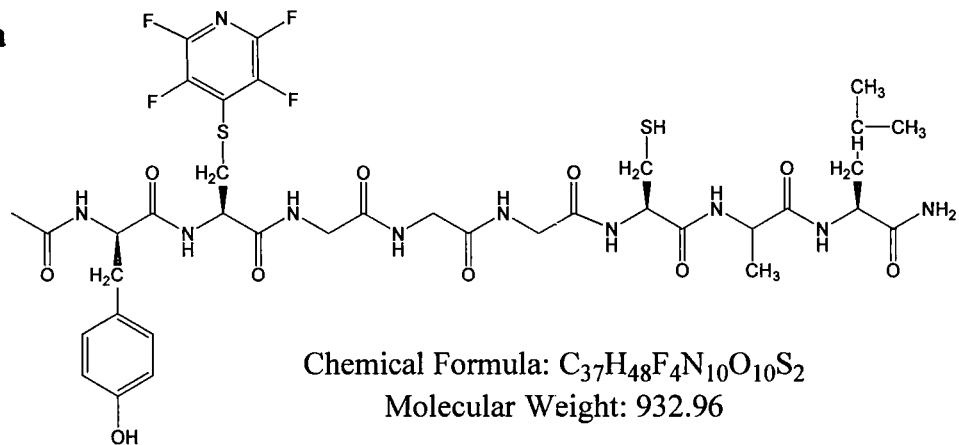
Figure 42:
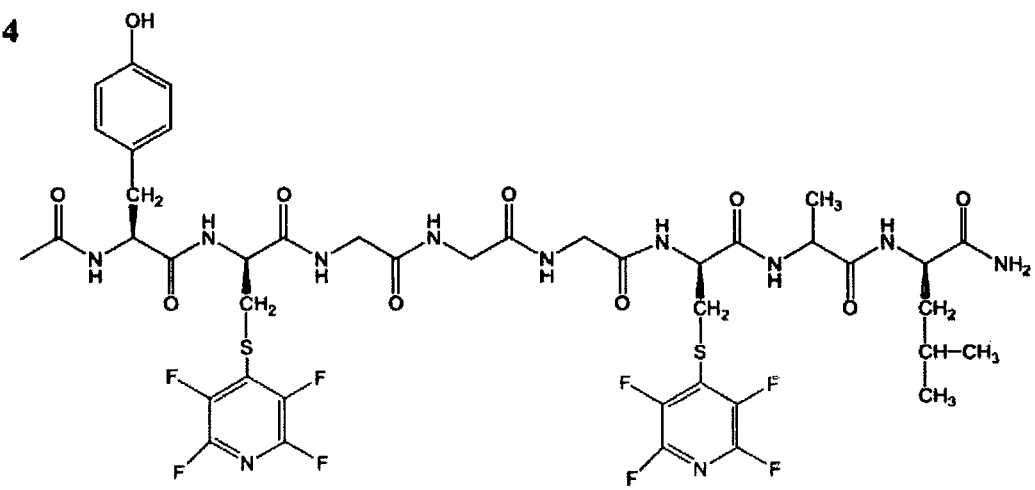
FIG. 42 shows the chemical structure for product P14.

However, the reaction of peptide 1 with pentafluoropyridine according to procedure D produced two products that were isolated, purified and characterised. The first of the products was P7a, the chemical structure of which is shown in FIG. 41. The second product, was characterised to be the di-cysteine substituted product P14. The chemical structure for P14 are shown in FIG. 42. Both P7a and P14 have no substitution on the tyrosine residue of peptide 1. This shows that by using TFE as the solvent, it is possible to selectively introduce fluoro-heteroaromatic groups at the sulphur (cysteine) positions of peptide 1 over the oxygen-containing tyrosine position.

Perfluorinated solvents have been shown to accelerate organic chemistry reactions,[viii] including $S_NAr$ reactions of fluoropurines.[ix] 2,2,2-Trifluoroethanol (TFE) has also been the subject of several studies involving peptides and proteins and has been shown to stabilise α-helical secondary structures.[x,xi,xii,xiii] Using the procedures developed previously[viii] we have demonstrated that, rather than enhancing reactivity, employing 2,2,2-trifluoroethanol (TFE) as the solvent in our system broadly attenuated the reactivity of the electrophiles under investigation. Under these conditions hexafluorobenzene did not react with any peptide side chain (see table 11 entries 1-3). Previously, regiocontrol using pentafluoropyridine was challenging and multiple substitution products were observed, including substitution on the competing tyrosine. Replacement of DMF with TFE afforded a mild method for controlled introduction of fluoro-heteroaromatics at cysteine.

Also as table 11, entries 5 and 6 show in the presence of the solvent TFE peptide 2 (di-serine peptide) and peptide 3 (di-lysine peptide) do not react with pentafluoropyridine.

Accordingly, TFE can be used to allow selective tagging of cysteine (or sulphur nucleophiles) in the presence of serine and lysine residues.

Example 8

Selective Cysteine Tagging Using with Fluoro-Heteroaromatics in the Presence of Lysine Employing TFE as Solvent Based on the results from Example 7, the inventors subsequently wanted to apply the application of TFE induced selectivity to peptide systems containing mixed cysteine and lysine side chain functionalities, such as peptide 4, to provide further evidence that they could obtain selective functionalization between sulphur (cysteine) and nitrogen (lysine).

Peptide 4, was reacted according to procedures E and F. The general reaction is shown below. The differences between the various reactions and the relative ratio of the products obtained is outlined below and is summarised in table 14.

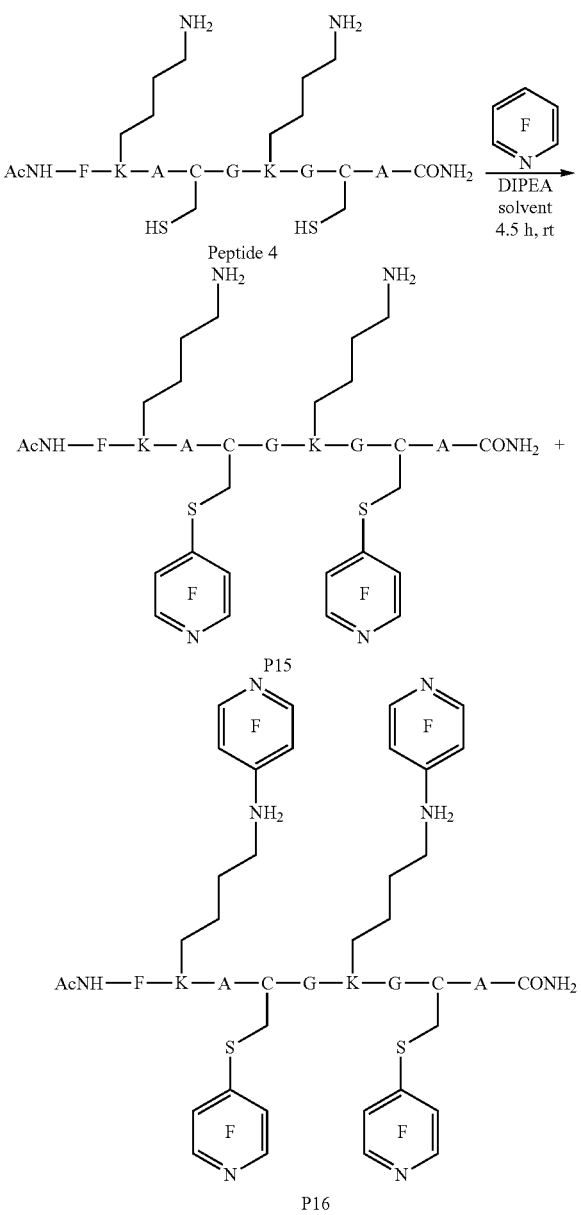

As can be seen above, two products were obtained. The main peak in the mass spectrum for product P15 was at 1265.84 m/z, which corresponds to product P15 with an MeCN adduct. Similarly, the main peak in the mass spectrum for product P16 is at 1565.99 m/z, which corresponds to product P16 with an MeCN adduct.

Figure 43:
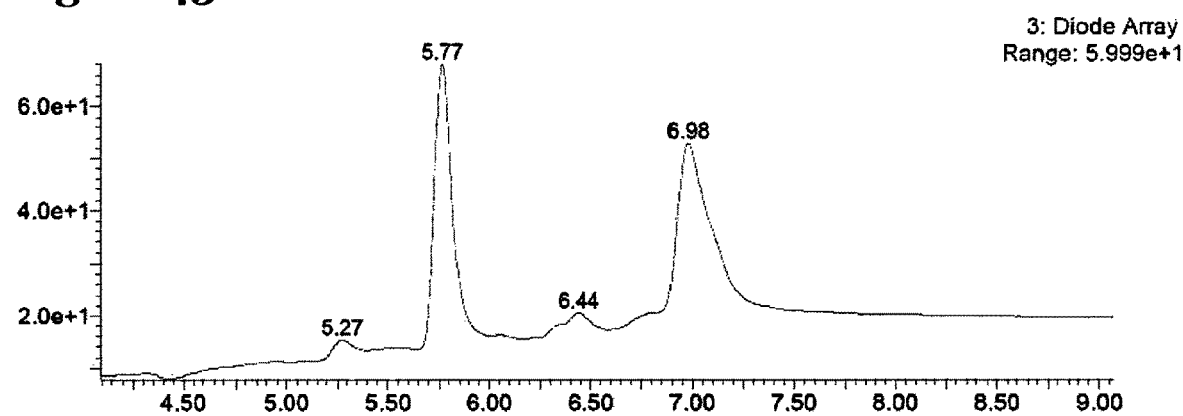
FIG. 43 is an LCMS chromatogram for the crude products formed by reacting peptide 4 according to procedure E, where the solvent for the reaction was DMF.

The LCMS chromatogram of the reaction of peptide 4 according to procedure E, using DMF as the solvent for the reaction is shown in FIG. 43. This shows two major peaks in the LCMS chromatogram, with retention times of 5.77 minutes and 6.98 minutes, and a smaller peak with a retention time of 6.44 minutes. It was found that the peak at 5.77 minutes corresponded to unreacted peptide 4, the peak at 6.44 minutes corresponded to product P15 and the peak at 6.98 minutes corresponded to product P16.

Figure 44:
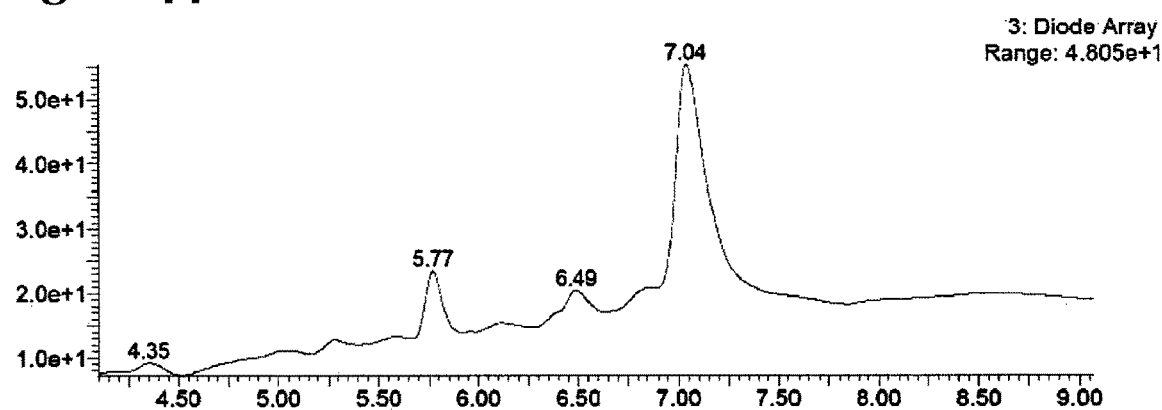
FIG. 44 is an LCMS chromatogram for the crude products formed by reacting peptide 4 according to procedure F, where the solvent for the reaction was DMF.

The LCMS chromatogram of the reaction of peptide 4 according to procedure F, using DMF as the solvent for the reaction is shown in FIG. 44. As before, this shows two major peaks in the LCMS chromatogram, with retention times of 5.77 minutes (corresponding to unreacted peptide) and 7.04 minutes (corresponding to product P16), and a smaller peak with a retention time of 6.49 minutes (corresponding to product P15).

Both these show that while product P15 was present, the predominant product formed when the solvent was DMF was product P16.

Figure 45:
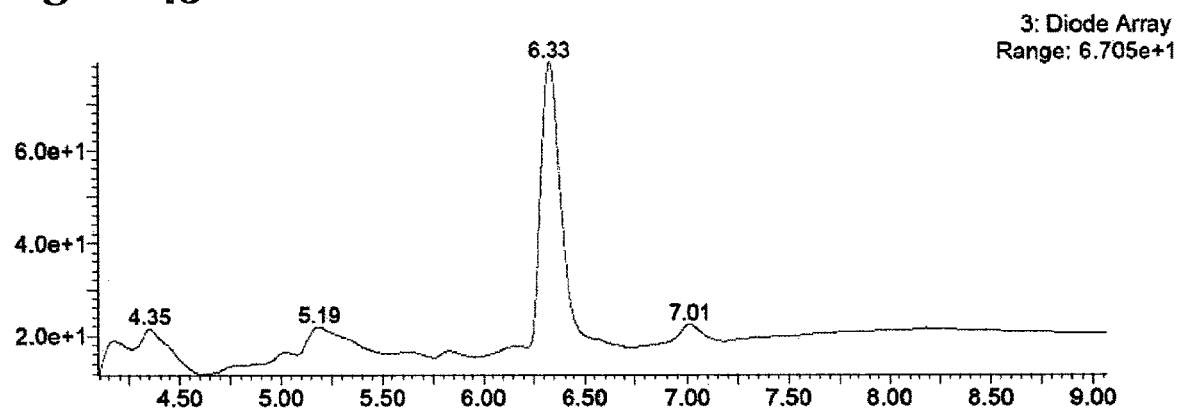
FIG. 45 is an LCMS chromatogram for the crude products formed by reacting peptide 4 according to procedure E, where the solvent for the reaction was TFE.

The LCMS chromatogram of the reaction of peptide 4 according to procedure E, using TFE as the solvent for the reaction is shown in FIG. 45. This shows a major peak in the LCMS chromatogram, with a retention time of 6.33 minutes (corresponding to product P15), and a smaller peak with a retention time of 7.01 minutes (corresponding to product P16). There was no peak present corresponding to unreacted peptide.

Figure 46:
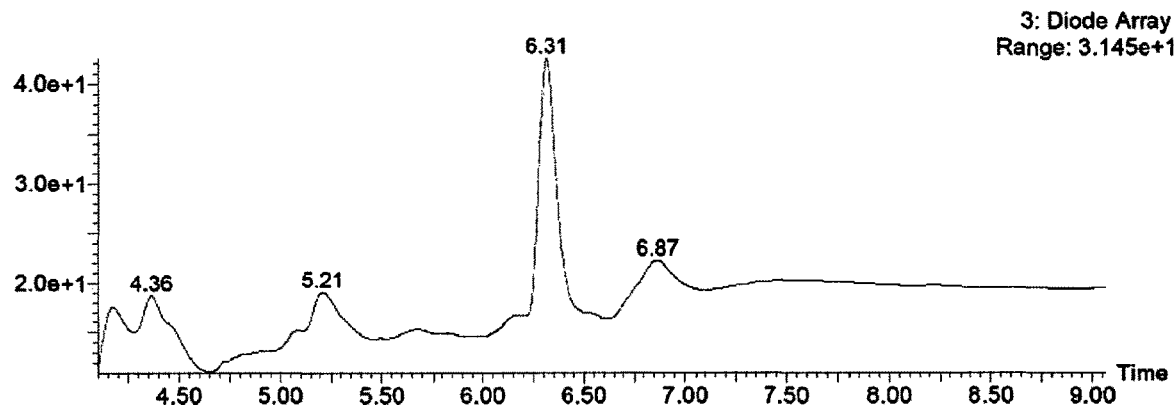
FIG. 46 is an LCMS chromatogram for the crude products formed by reacting peptide 4 according to procedure F, where the solvent for the reaction was TFE.

The LCMS chromatogram of the reaction of peptide 4 according to procedure F, using TFE as the solvent for the reaction is shown in FIG. 46. This shows a major peak in the LCMS chromatogram, with a retention time of 6.31 minutes (corresponding to product P15), and a smaller peak with a retention time of 6.87 minutes (corresponding to product P16). There was no peak present corresponding to unreacted peptide.

Both these show that while product P16 was present, the predominant product formed when the solvent was TFE was product P15. Thus, when TFE was used as the solvent the cystenine was tagged selectively in the presence of lysine.

The relative ratios of products P15 and P16 for the various reactions are set out in table 12 below.

TABLE 12

Differences between the reaction procedures used and the ratio of the products obtained when peptide was reacted according to procedures E and F

| Solvent | Procedure used | Molar equivalents of pentafluoropyridine | Relative ratio of products | |
|---|---|---|---|---|
| | | | P15 | P16 |
| DMF | E | 3 | 1 | 10.7 |
| DMF | F | 1 | 1 | 9.6 |
| TFE | E | 3 | 13.3 | 1 |
| TFE | F | 1 | 2.8 | 1 |

As explained above, treatment of the mixed functionality peptide with pentafluopyridine in DMF led to almost complete reaction at both cysteine and both lysine side chains, whereas, the reaction carried out in TFE afforded reaction almost exclusively at both cysteine, leaving the lysines free.

Example 9

Preparing Cyclic Peptides Using Perfluoroheteroaromatics

Peptide 1, was reacted according to procedure G. The reaction is shown below and the product for the reaction is shown in table 12.

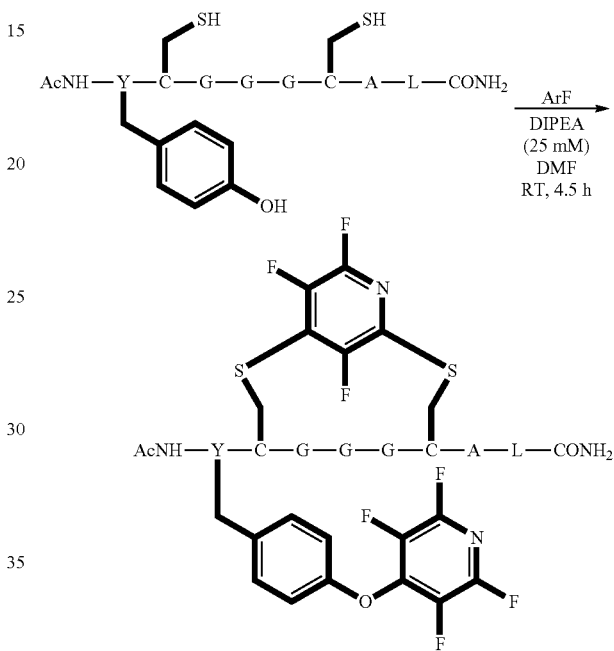

TABLE 13

Reaction of peptide 1 with perfluoroheteroaromatics using procedure G

| Procedure | ArF | Products formed |
|---|---|---|
| G | | |

The crude reaction products were analysed used LCMS. The LCMS chromatogram had a peak with a retention time of 2.90 minutes, which was analysed and showed an [M+H]+ peak at 1063.544 m/z, which indicated a cyclic product was formed, as shown above.

This shows that when the concentration of the reagents is lower the reaction favours the formation of a cyclic peptide in a one step synthesis as opposed to a multiply substituted product, as described in many of the previous examples.

Example 10

Preparation of Multi-Cyclic Peptides Using Fluoro-Heteroaromatics

It is also possible to prepare multi cyclic peptide constructs from linear peptide and peptide mimetic sequences containing 3 or more nucleophilic side chains using the methods outlined previously.

These multicyclic peptides (or peptide mimetics may be prepared in a 'one-pot' fashion by nucleophilic aromatic substitution reaction of an appropriate perfluoro heteroaromatic with a peptide (or peptide mimic) containing 3 or more nucleophilic side chains according to the general reaction set out below. Examples of mutli-cyclic peptoid constructs prepared using this approach are detailed in Example 11.

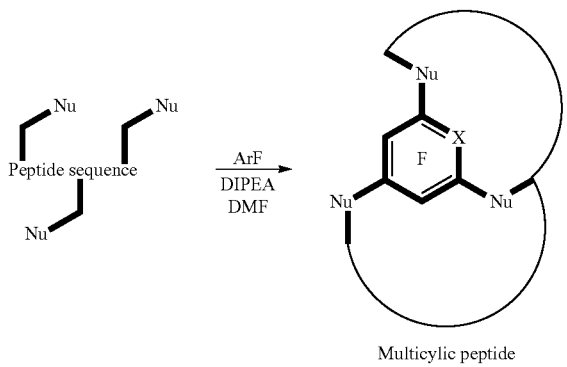

Multicylic peptide

It is also conceivable that multicyclic peptides (or peptide mimetics) can be accessed in a regioselective 'step-wise' fashion by sequential reaction of judiciously positioned thiol (e.g. cysteine) residues with a chosen perfluoroheteroaromatic using TFE as the solvent to selectively form a first macrocycle, followed by reaction in DMF with a second perfluoro heteroaromatic to furnish a second attached macrocycle through reaction at amine (e.g. lysine) side chains as shown below.

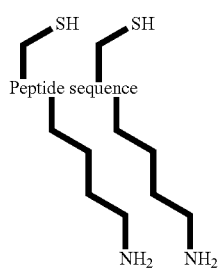

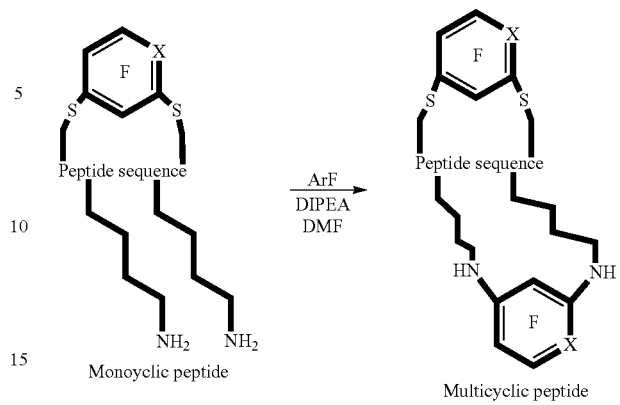

Alternatively, a peptide (or peptide mimetics) can initially form a monocyclic peptide as in Method 2, however, rather than reacting with a second perfluoro heteroaromatic, the available amine (e.g. lysine) functionality can react further at available positions on the attached perfluoro heteroaromatic to form a multicyclic system as shown below.

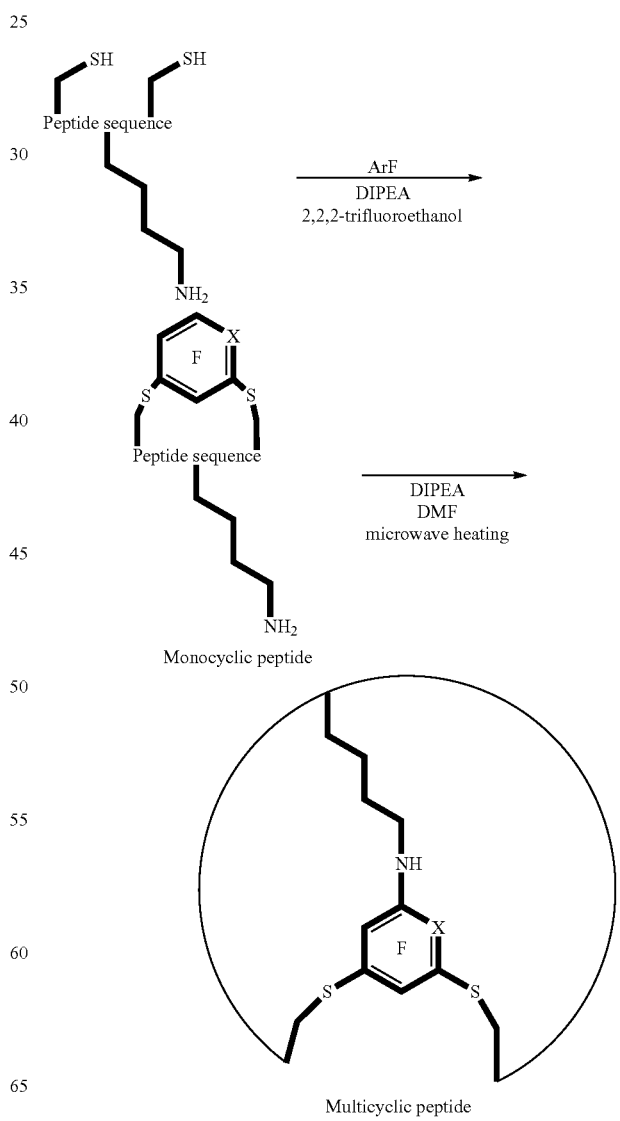

Alternatively, a peptide (or peptide mimetic) can initially be prepared where only one reactive site is revealed and the remaining nucleophilic side chains are protected. An example of this peptide is peptide 6. Peptide 6 can then be reacted selectively with a fluoro-heteroaromatic as shown in the two examples below.

The LCMS chromatogram (280 nm) for purified P17 has a peak with a retention time of 2.622 minutes and the mass spectrum for that peak has an [M+H]$^+$ peak at 1235.84 m/z. The LCMS chromatogram (280 nm) for purified P18 has a peak with a retention time of 2.571 minutes and the mass spectrum for that peak has an [M+H]$^+$ peak at 1219.037 m/z.

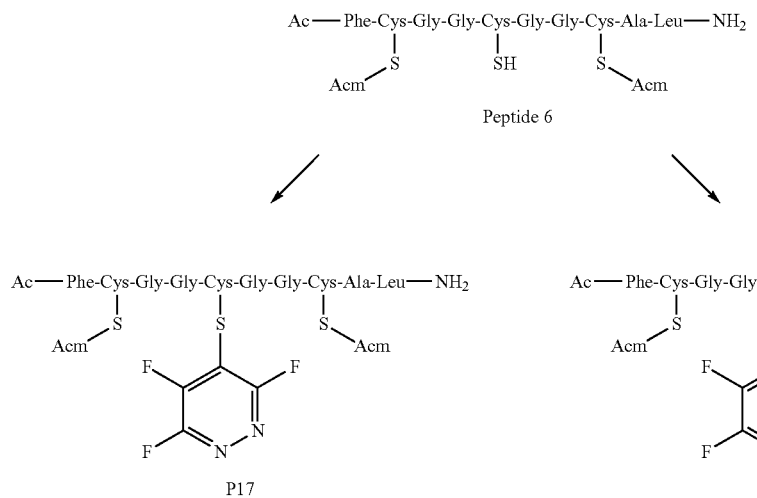

Removal of the Acm protecting group and subsequent cyclisation onto the fluoro-heteroaromatic rings would give rise to multi-cyclic peptide systems. An overview of this stepwise approach to prepare multi-cyclic peptide constructs is shown below.

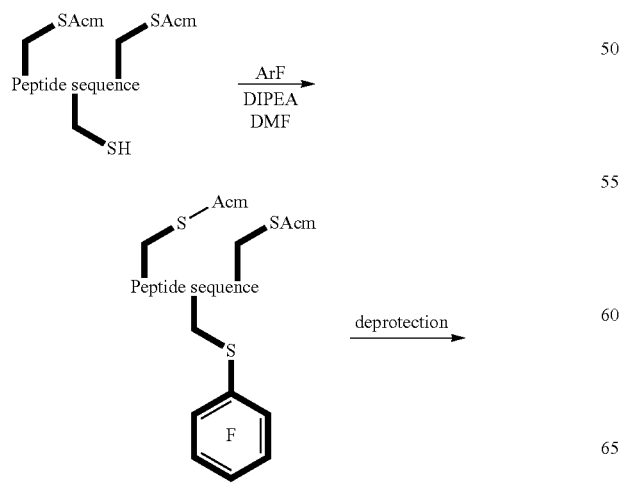

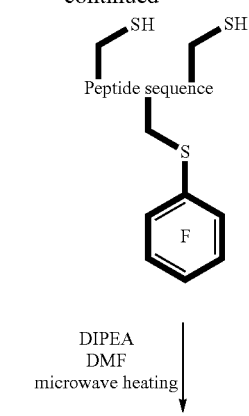

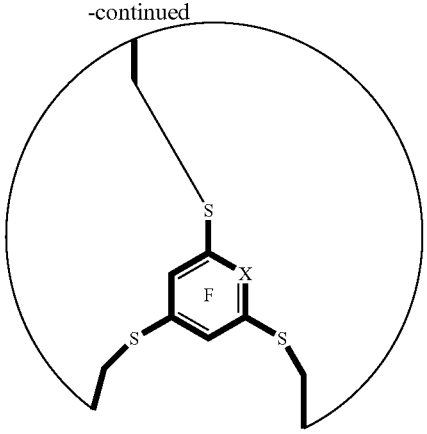

Multicyclic peptide

Example 11

Reaction of Cysteine-Containing Peptoids with Fluoro-Heteroaromatics

Figure 47:
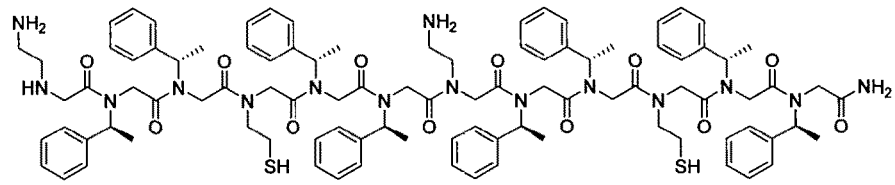
FIG. 47 shows the structure for peptoid 1.
Figure 48:
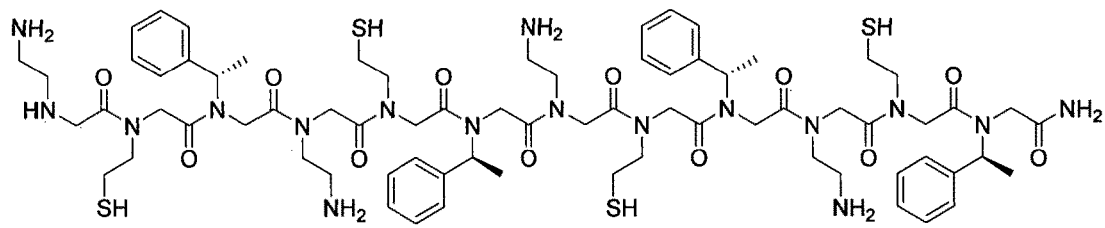
FIG. 48 shows the structure for peptoid 2.

The chemical structures for peptoid 1 and 2 is given in FIGS. 47 and 48 respectively.

Peptoids 1 and 2 were reacted according to procedure I, and the results are shown in table 14.

TABLE 14

Reaction of peptoids 1 and 2 with pentafluoropyridine and fluoro-heteroaromatic (I) using procedure I.

Figure 49:
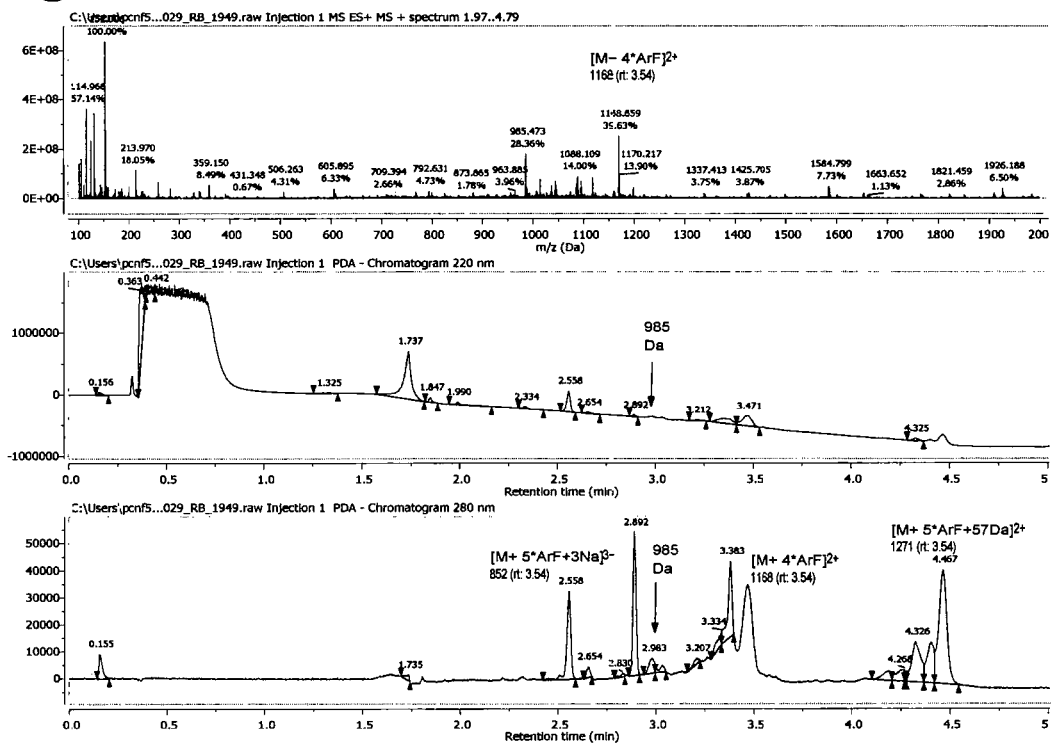
FIG. 49 is the LCMS spectrum and chromatogram at 220 nm and 280 nm for the products formed by reacting peptoid 1 with pentafluoropyridine according to procedure I.
Figure 51:
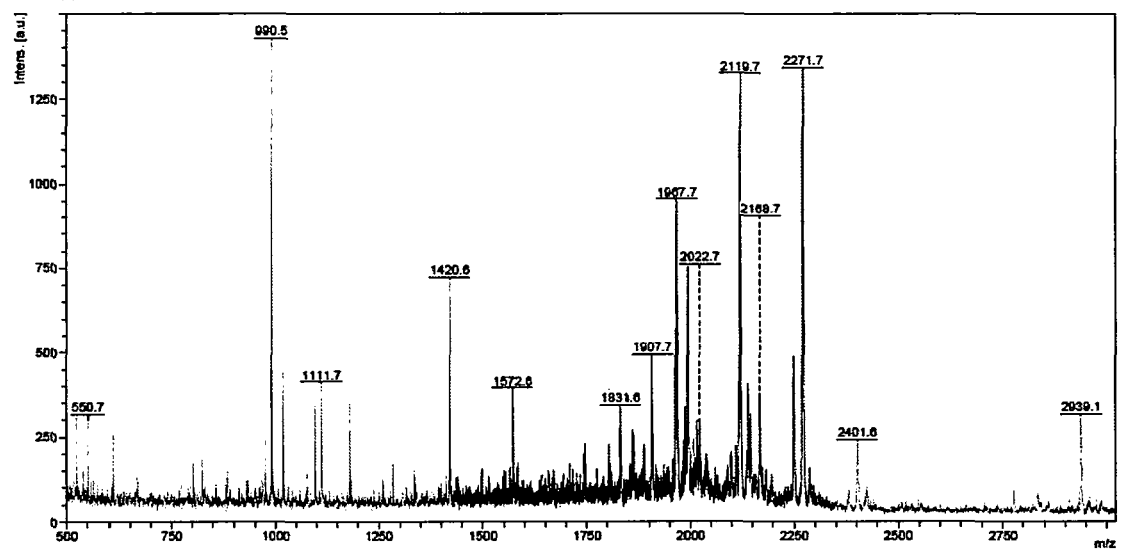
FIG. 51 is the MALDI-Tof spectra for the products formed by reacting peptoid 1 with fluoro-heteroaromatic (I) according to procedure I.
Figure 52:
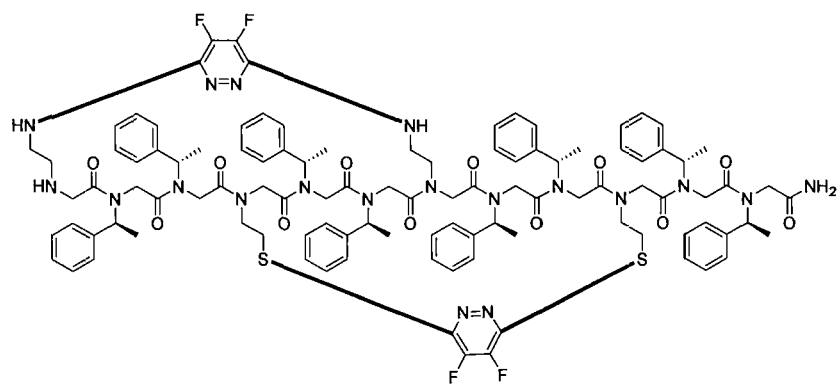
FIG. 52 shows the structure of a product formed by reacting peptoid 1 with fluoro-heteroaromatic (I) according to procedure I.
Figure 53:
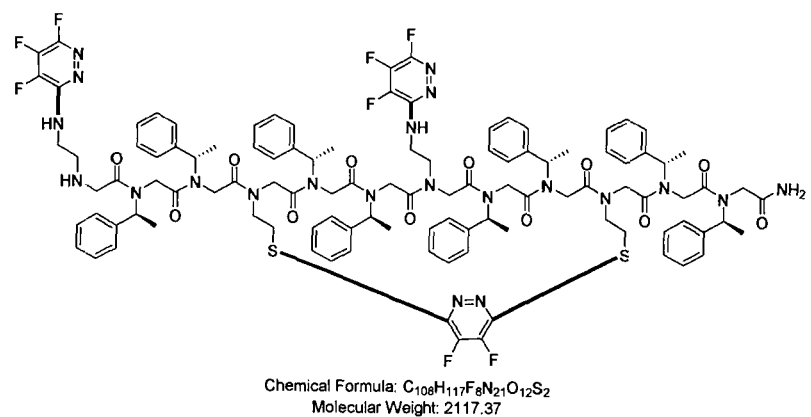
FIG. 53 shows the structure of a product formed by reacting peptoid 1 with fluoro-heteroaromatic (I) according to procedure I.
Figure 54:
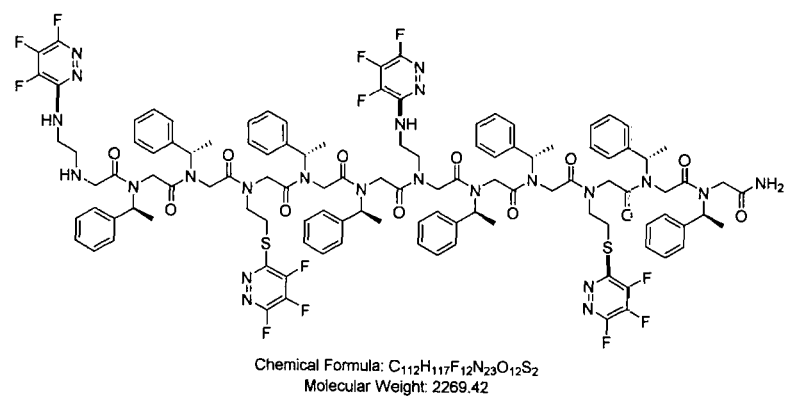
FIG. 54 shows the structure of a product formed by reacting peptoid 1 with fluoro-heteroaromatic (I) according to procedure I.
Figure 55:
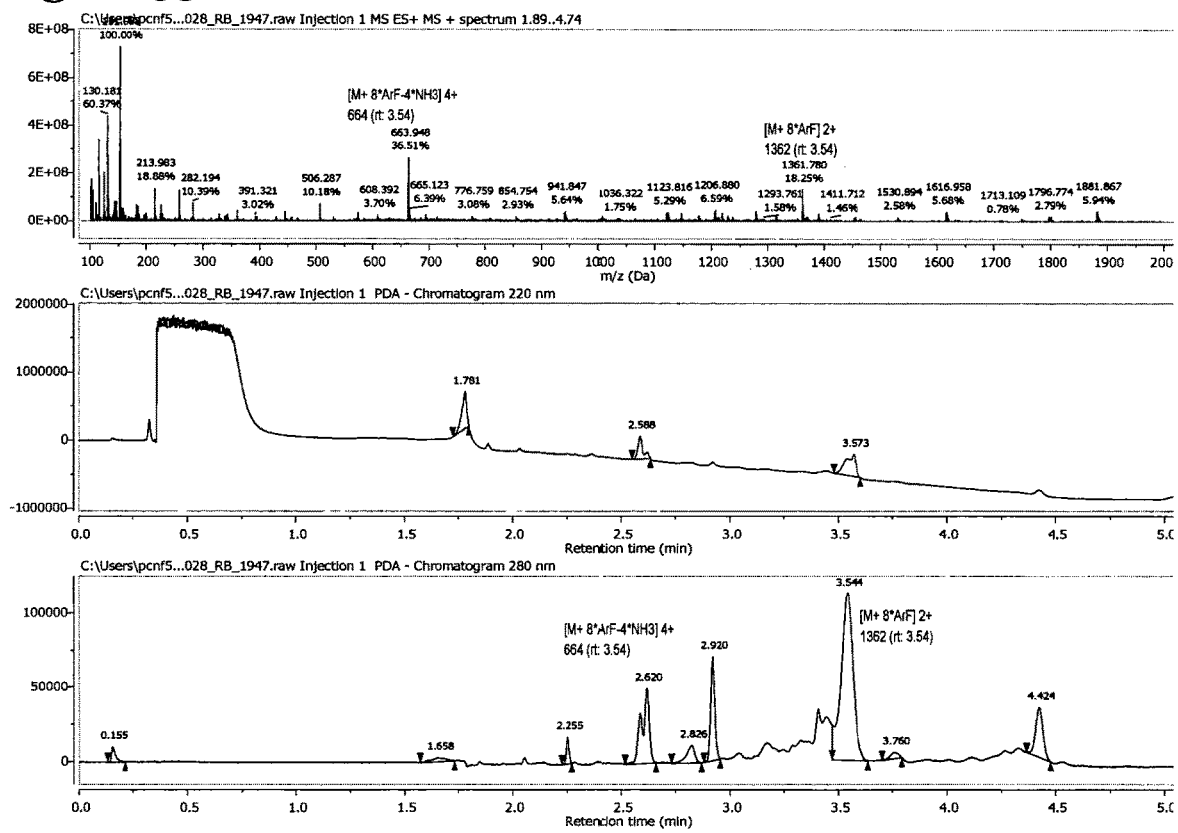
FIG. 55 is the LCMS spectrum and chromatogram at 220 nm and 280 nm for the products formed by reacting peptoid 2 with pentafluoropyridine according to procedure I.
Figure 57:
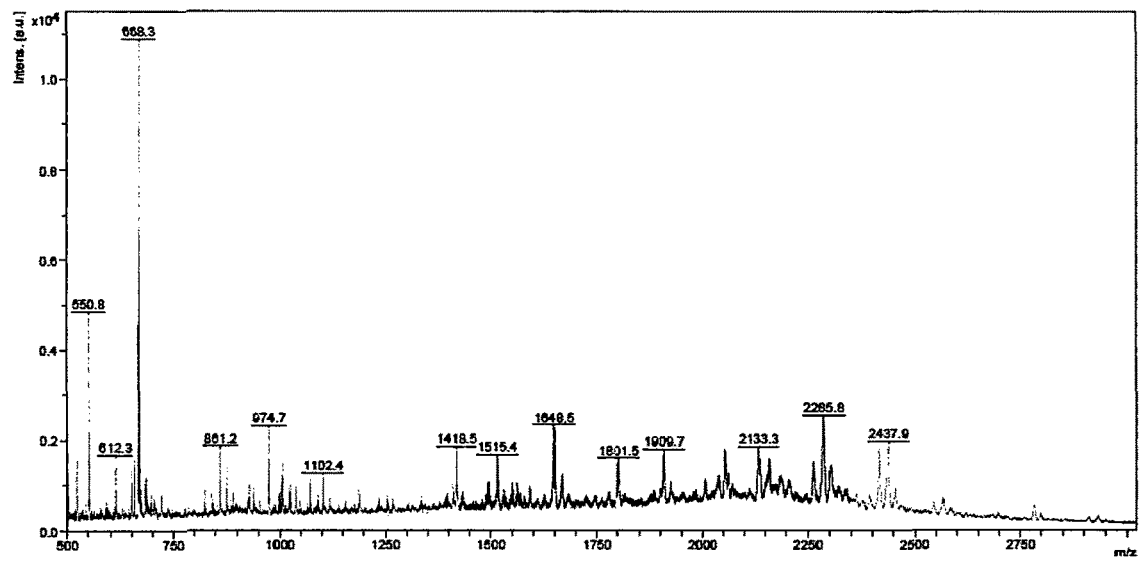
FIG. 57 is the MALDI-Tof spectra for the products formed by reacting peptoid 1 with fluoro-heteroaromatic (I) according to procedure I.
Figure 58:
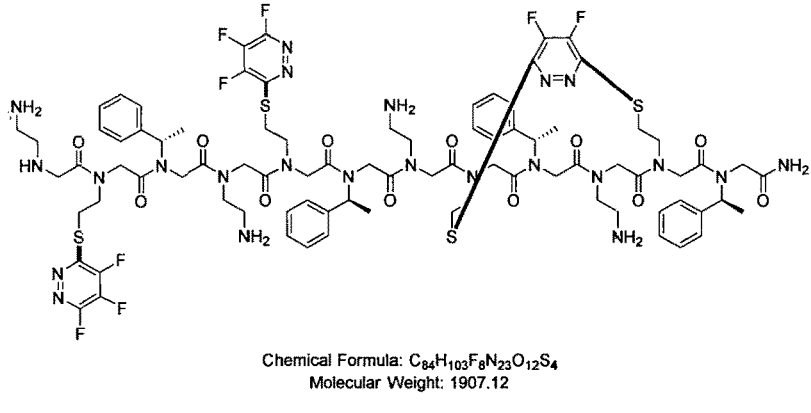
FIG. 58 shows the structure of a product formed by reacting peptoid 2 with fluoro-heteroaromatic (I) according to procedure I.
Figure 59:
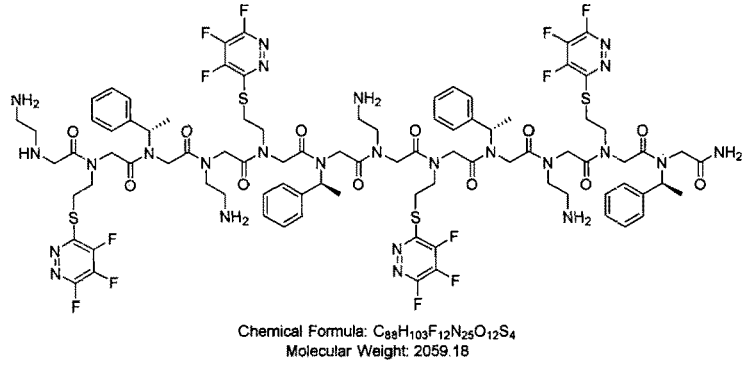
FIG. 59 shows the structure of a product formed by reacting peptoid 2 with fluoro-heteroaromatic (I) according to procedure I.
Figure 60:
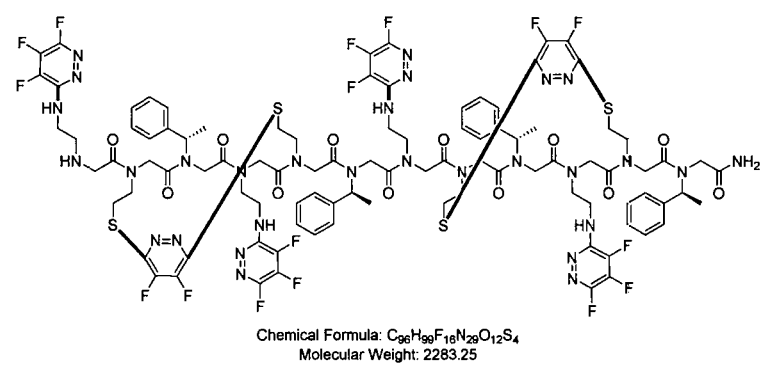
FIG. 60 shows the structure of a product formed by reacting peptoid 2 with fluoro-heteroaromatic (I) according to procedure I.
Figure 61:
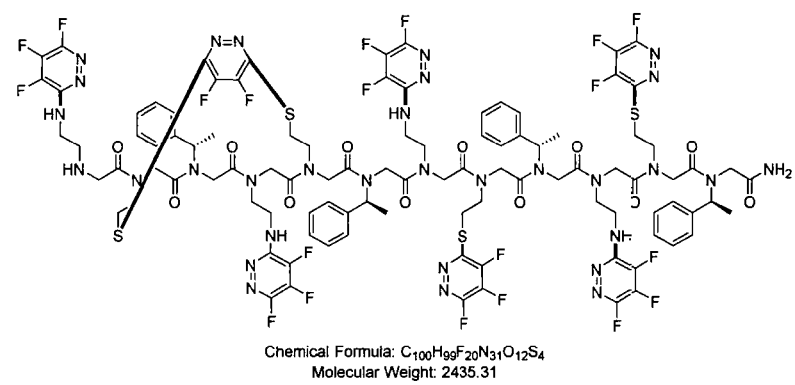
FIG. 61 shows the structure of a product formed by reacting peptoid 2 with fluoro-heteroaromatic (I) according to procedure I and FIG. 62 shows the chemical structure for product P5.

| Entry | Peptoid | ArF | Analysis | Products |
|---|---|---|---|---|
| 1 | 1 | 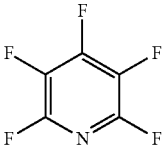 | LCMS shown in FIG. 49. | A mixture of products were obtained. The main product observed was a tetra-substituted, see FIG. 50 |
| 2 | 1 | 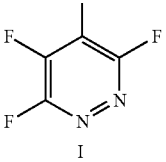 I | MALDI-Tof analysis shown in FIG. 51. | A bi-cyclic product, see FIG. 52, a mono-cyclic, di-substituted product, see FIG. 53, and a tetra-substituted product, see FIG. 54, were obtained. |
| 3 | 2 | 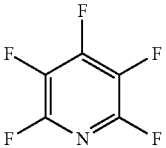 | LCMS shown in FIG. 55. | A mixture of products were obtained. The main product observed was an octa-substituted, see FIG. 56. |
| 4 | 2 |  I | MALDI-Tof analysis shown in FIG. 57. | A mono-cyclic, di-substituted product, see FIG. 58, a tetra-substituted product, see FIG. 59, a di-cyclic, tetra-substituted product, see FIG. 60, and a mono-cyclic, hexa-substituted product, see FIG. 61, were obtained. |

Figure 50:
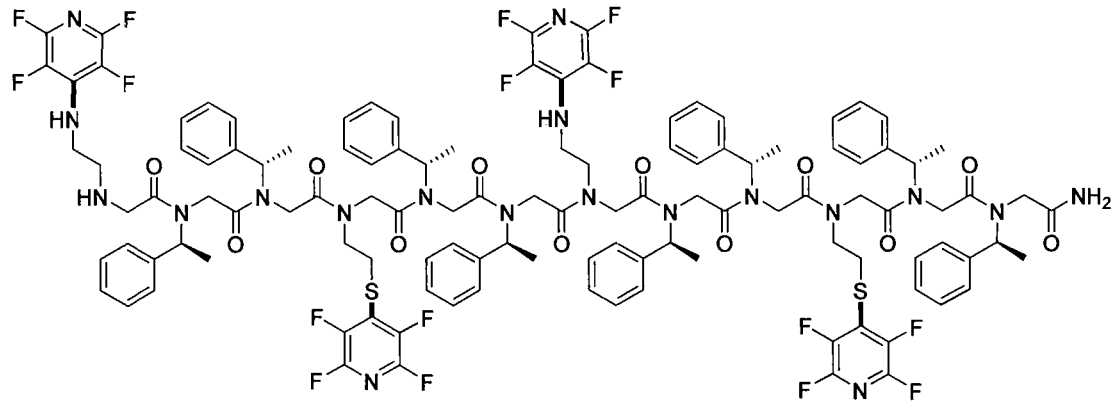
FIG. 50 shows the structure, of a product formed by reacting peptoid 1 with pentafluoropyridine according to procedure I.
Figure 56:
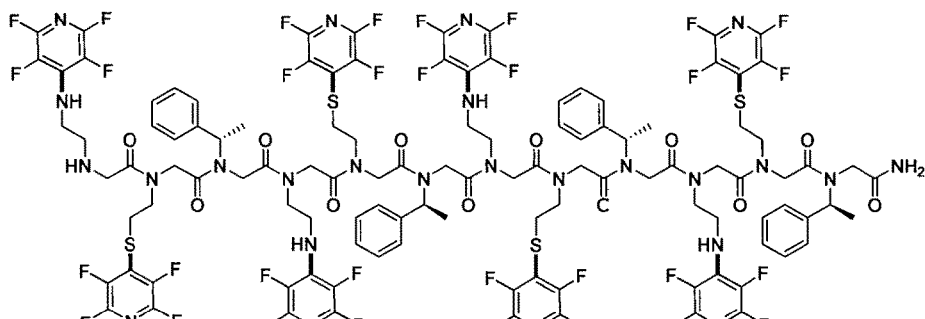
FIG. 56 shows the structure of a product formed by reacting peptoid 2 with pentafluoropyridine according to procedure I.

The reaction of peptoids 1 and 2 with pentafluoropyridine according to procedure I results predominately in the formation of linear multiply substituted products (FIGS. 50 and 56).

However, the reaction peptoids 1 and 2 with fluoro-heteroaromatic (I) according to procedure I results predominately in the formation of cyclic (FIGS. 53, 58, 61) and multi-cyclic (FIGS. 52 and 60) products.

Example 12

Cyclisation with Further Heteroaromatics

To show that further fluoro-heteroaromatic compounds could be used to cyclise peptides further reactions were carried out on peptides 7 to 10 using procedure D, and the results are shown below in table 15.

TABLE 15

Reaction of peptides 7 to 10 according to procedure D

| Peptide | Fluoro-heteroaromatic | LCMS spectrum and chromatogram | Product |
|---|---|---|---|
| 7 | 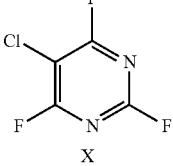 X | Peak in LCMS chromatogram with retention time of 3.183 minutes/ The spectrum for this peak shows an [M + H]+ peak at 1254.47 m/z. | 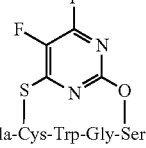 Ac-Ala-Cys-Trp-Gly-Ser-Ile-Leu-Ala-Arg-Thr-NH$_2$ |
| 8 | 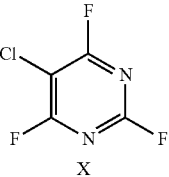 X | Two major peaks in the LCMS chromatogram with retention times of 2.750 minutes and 3.833 minutes. The spectrum for these peaks show an [M + 2 MeCN + H]+ peak at 1288 m/z and an [M + H]+ peak at 1686 m/z. |  Ac-Ala-Cys-Tyr-Gly-Ser-Ile-Leu-Ala-Arg-Thr-NH$_2$ |

TABLE 15-continued

Reaction of peptides 7 to 10 according to procedure D

| Peptide | Fluoro-heteroaromatic | LCMS spectrum and chromatogram | Product |
|---|---|---|---|
| | | | 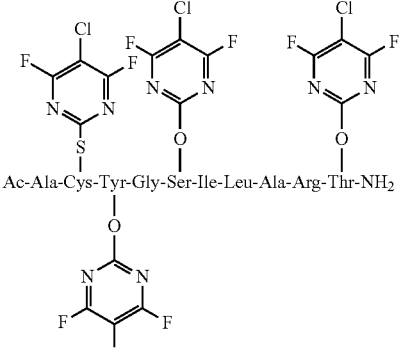
Ac-Ala-Cys-Tyr-Gly-Ser-Ile-Leu-Ala-Arg-Thr-NH$_2$ |
| 9 | 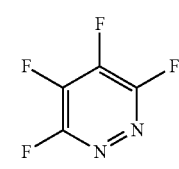
I | One major peak in the LCMS chromatogram with a retention time of 2.292 minutes, the spectrum for this peak shows an [M + H]$^+$ peak at 880 m/z. | 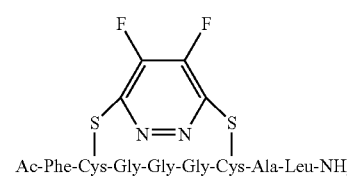
Ac-Phe-Cys-Gly-Gly-Gly-Cys-Ala-Leu-NH$_2$ |
| 9 | 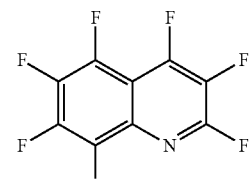
III | Two peaks in the LCMS chromatogram with retention times of 3.650 minutes and 3.125 minutes. The spectrum for these peaks show an [M + H]$^+$ peak at 1238 m/z and an [M + H]$^+$ peak at 982 m/z. | 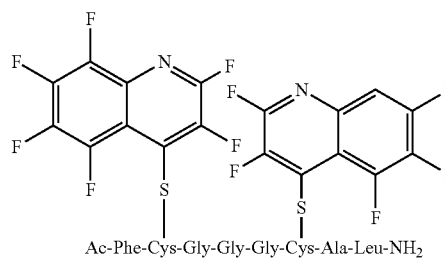
Ac-Phe-Cys-Gly-Gly-Gly-Cys-Ala-Leu-NH$_2$

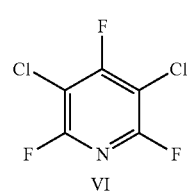
Ac-Phe-Cys-Gly-Gly-Gly-Cys-Ala-Leu-NH$_2$ |
| 9 | 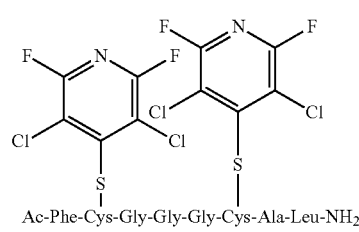
VI | Two major peaks in the LCMS chromatogram with retention times of 3.558 minutes and 2.583 minutes. The spectrum for these peaks showed an [M + H]$^+$ peak at 1132 m/z, and [M + H]$^+$ peak at and 929 m/z | 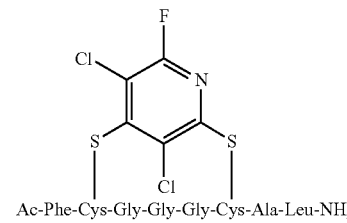
Ac-Phe-Cys-Gly-Gly-Gly-Cys-Ala-Leu-NH$_2$ |

TABLE 15-continued

Reaction of peptides 7 to 10 according to procedure D

| Peptide | Fluoro-heteroaromatic | LCMS spectrum and chromatogram | Product |
|---|---|---|---|
| 9 | 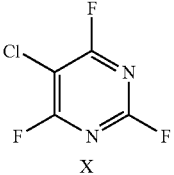  X | Two major peaks in the LCMS chromatogram with retention times of 3.208 minutes and 2.417 minutes. The spectrum for these peaks show an [M + H]⁺ peak at 1064 m/z, and [M + H]⁺ peaks at 896 m/z and 879 m/z. | 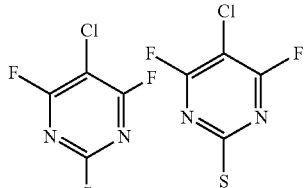 |
| 10 | 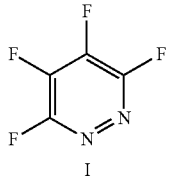  I | Two peaks in the LCMS chromatogram with retention times of 2.125 minutes and 2.197 minutes. The spectrum for these peaks show [M + H]⁺ peaks at 868 m/z, , 1000 m/z and 848 m/z. | 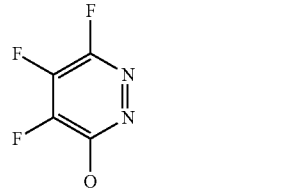 |

TABLE 15-continued

Reaction of peptides 7 to 10 according to procedure D

| Peptide | Fluoro-heteroaromatic | LCMS spectrum and chromatogram | Product |
|---------|----------------------|-------------------------------|---------|
| 10 | 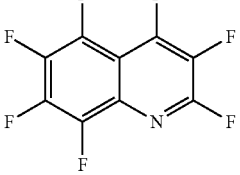 III | Two peaks in the LCMS chromatogram with retention times of 3.650 minutes and 2.708 minutes. The spectrum for these peaks show [M + H]+ peaks at 1206 m/z and 951 m/z. | 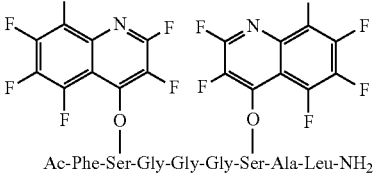 |

Accordingly, it will be apparent that a range of fluoroheteroaromatic compounds can be used to produce cyclic peptide scaffolds. It should also be noted that peptide cyclisation is also possible via two serine residues which is not possible using current published work.

Summary

Advantages of the invention include the possibility of stapling a range of amino acid residues not only on cysteine as with other published methodologies. Use of fluorinated reagents allows monitoring and analysis to be carried out using $^{19}$F NMR, which is not available in other heteroaromatic tag methods and selectivity for specific amino acids can be tuned by varying the solvent e.g. using TFE no tagging is observed at tyrosine or lysine.

REFERENCES

[i] Blackwell, H. E. and Grubbs, R. H. Highly Efficient Synthesis of Covalently Cross-Linked Peptide Helices by Ring-Closing Metathesis. *Angew. Chem. Int. Ed.* 1998, 37, 3281-3284.

[ii] Schafmeister, C. E. et al. An All-Hydrocarbon Cross-Linking System for Enhancing the Helicity and Metabolic Stability of Peptides. *J. Am. Chem. Soc.* 2000, 122, 5891-5892. [iii] Verdine, G. L. and Hilinski, G. J. Stapled Peptides for Intracellular Drug Targets. *Methods in Enzymology*, Elsevier Inc, 2012, Vol. 503. [iv] Craik, D. J. et al. The Future of Peptide-based Drugs. *Chem. Biol. Drug. Des.* 2013, 81,136-147.

[v] Christopher J. White and Andrei K. Yudin. Contemporary strategies for peptide macrocyclization. *Nature Chemistry*, 2011, 3, 509-524

[vi] Hudson, A. S. et al. Synthesis of a novel tetrafluoropyridine-containing amino acid and tripeptide. *Tet. Lett*, 2013, 54, 4865-4867.

[vii] Alexandra M. Webster et al. A Mild Method for the Synthesis of a Dehydrobutyrine Containing Amino Acid. *Tetrahedron*, 2014, article accepted

[viii] Coxon, C. R. et al. Investigating the potential application of pentafluoropyridine based reagents in the preparation of novel peptide systems. *Org. Biomol. Chem.*

Manuscript in Preparation

[ix] Alexander M. Spokoyny et al. A Perfluoroaryl-Cysteine $S_N$Ar Chemistry Approach to Unprotected Peptide Stapling. *J. Am. Chem. Soc.* 2013, 135, 5946-5949.

[x] Yekui Zou et al. Convergent diversity-oriented side-chain macrocyclization scan for unprotected peptides. *Org. Biomol. Chem.* 2014, 135, 5946-5949

[xi] A. Berkessel et al. Dramatic Acceleration of Olefin Epoxidation in Fluorinated Alcohols: Activation of Hydrogen Peroxide by Multiple H-Bond Networks. *J. Am. Chem. Soc.*, 2006, 128, 8421-8426.

[xii] Trifluoroacetic Acid in 2,2,2-Trifluoroethanol Facilitates $S_N$Ar Reactions of Heterocycles with Arylamines. Benoit Carbain et al. *Chem. Eur. J.* 2014, 20, 2311-2317

[xiii] Kentaro Shiraki et al. Trifluoroethanol-induced Stabilization of the α-Helical Structure of β-Lactoglobulin: Implication for Non-hierarchical Protein Folding. *J. Mol. Biol.* 1995, 245, 180-194.

[xiv] F. D. Sonnichsen et al. Effect of trifluoroethanol on protein secondary structure: an NMR and CD study using a synthetic actin peptide. *Biochemistry*, 1992, 31, 8790-8798.

[xv] Peizhi Luo and Robert L. Baldwin. Mechanism of Helix Induction by Trifluoroethanol: A Framework for Extrapolating the Helix-Forming Properties of Peptides from Trifluoroethanol/Water Mixtures Back to Water. *Biochemistry*, 1997, 36, 8413.

[xvi] K. Gast et al. Trifluoroethanol-induced conformational transitions of proteins: insights gained from the differences between alpha-lactalbumin and ribonuclease A. Protein Sci. 1999, 8, 625-634.

The invention claimed is:

1. A method for preparing a bridged peptide, derivative or analogue thereof, the method comprising contacting a reactant comprising a peptide, derivative or analogue thereof with a fluoro-heteroaromatic compound to form a bridged structure with the peptide, derivative or analogue thereof, wherein the fluoro-heteroaromatic compound comprises at least two halogen atoms, wherein all of the at least two halogen atoms are fluorine atoms or the at least two halogen atoms comprise at least one fluorine atom and at least one chlorine atom, the reactant comprises at least two nucleophilic side chains at least one of which comprises a thiol group, and the method is carried out with the reactant in solution using a solvent and the solvent is 2,2,2-trifluoroethanol (TFE), and the reactant is:
a) a peptide;
b) a peptide where one or more of the amino acids residues of the peptide are replaced by residues with similar side chains or peptide backbone properties;
c) a peptide where terminal groups thereof are protected by N- and C- terminal protecting groups with similar properties to acetyl or amide groups;
d) a peptoid;
e) a retropeptoid;
f) a peptide-peptoid hybrid; or
g) a peptide where at least one of the amino acids residues of the peptide is a D-amino acid.

2. The method according to claim 1, wherein the bridged peptide comprises at least two, three, four or five amino acid residues.

3. The method according to claim 1, wherein the fluoro-heteroaromatic compound contains one, two or three nitrogen atoms in the aromatic ring.

4. The method according to claim 1, wherein the fluoro-heteroaromatic compound comprises at least one hydrogen atom.

5. The method according to claim 1, wherein a first nucleophilic side chain reacts in an $S_NAr$ type reaction with the fluoro-heteroaromatic compound to displace a fluorine atom and create a covalent bond between the first nucleophilic side chain and the fluoro-heteroaromatic compound, and subsequently a second nucleophilic side chain reacts in an $S_NAr$ type reaction with the fluoro-heteroaromatic compound, which is covalently bonded to the first nucleophilic side chain, to displace a further fluorine atom and create a covalent bond between the second nucleophilic side chain and the fluoro-heteroaromatic compound, thereby creating a linker between the first and second nucleophilic side chains, and thereby forming the bridged peptide, derivative or analogue thereof.

6. The method according to claim 1, wherein at least one of the nucleophilic side chains comprises an amine group, and/or an alcohol group.

7. The method according to claim 6, wherein the or each thiol is provided on a cysteine residue or modified cysteine residue in the reactant, or the or each amine group is provided on a lysine residue in the reactant, and/or the or each alcohol group is provided on a tyrosine, serine or threonine residue within the reactant.

8. The method according to claim 1, wherein the bridged peptide, derivative or analogue thereof that is prepared comprises one bridging structure.

9. The method according to claim 1, wherein the bridged peptide, derivative or analogue thereof that is prepared comprises multiple bridging structures.

10. The method according to claim 1, wherein the at least two nucleophilic side chains comprise at least one thiol group and at least one phenol group and the fluoro-heteroaromatic compound reacts selectively with the at least one thiol group.

11. The method according to claim 1, wherein the at least two nucleophilic side chains comprise at least one amine group and at least one phenol group and the fluoro-heteroaromatic compound reacts selectively with the at least one amine group.

12. The method according to claim 1, wherein the at least two nucleophilic side chains comprise at least one thiol group and at least one amine group and the fluoro-heteroaromatic compound reacts selectively with the at least one thiol group.

13. The method according to claim 1, wherein the method comprises dissolving a peptide, derivative or analogue thereof in a solvent, and adding a base thereto before the fluoro-heteroaromatic compound is added to the dissolved peptide to create a reaction solution.

14. The method according to claim 13, wherein the method further comprises subjecting the solution to a vacuum to remove a volatile liquid, and/or wherein the step of mixing the solution is undertaken at at least 30° C.

15. The method according to claim 1, wherein the molar ratio of the peptide, derivative or analogue thereof to the fluoro-heteroaromatic compound is between 1:1 and 1:100.

16. A method for producing a bridged peptide, derivative or analogue thereof in a "step-wise" fashion, the method comprising at least two steps sequentially, wherein the first step comprises contacting a reactant comprising a peptide, derivative or analogue thereof with a fluoro-heteroaromatic compound to create a chemically modified peptide, derivative or analogue thereof, and the second step comprises contacting the chemically modified peptide, derivative or analogue thereof with a fluoro-heteroaromatic compound to cyclise the chemically modified peptide, derivative or analogue thereof, wherein the fluoro-heteroaromatic compound comprises at least two halogen atoms, wherein all of the at least two halogen atoms are fluorine atoms or the at least two halogen atoms comprise at least one fluorine atom and at least one chlorine atom, the reactant comprises at least two nucleophilic side chains at least one of which comprises a thiol group, the solvent for the first step is 2,2,2-trifluoroethanol (TFE) and the solvent for the second step is dimethylformamide (DMF), and the reactant is:
a) a peptide;
b) a peptide where one or more of the amino acids residues of the peptide are replaced by residues with similar side chains or peptide backbone properties;
c) a peptide where terminal groups thereof are protected by N- and C- terminal protecting groups with similar properties to acetyl or amide groups;
d) a peptoid;
e) a retropeptoid;
f) a peptide-peptoid hybrid; or
g) a peptide where at least one of the amino acids residues of the peptide is a D-amino acid.

17. The method according to claim 16, wherein the second step comprises contacting the chemically modified peptide, derivative or analogue thereof with a fluoro-heteroaromatic compound which is added to the reaction during the second step, or further contacting the chemically modified peptide, derivative or analogue thereof with a fluoro-heteroaromatic compound which is already attached to the chemically modified peptide, derivative or analogue thereof by at least one chemical bond.

18. The method according to claim 1, wherein the fluoro-heteroaromatic compound comprises a perfluoroheteroaromatic compound.

* * * * *

SEQUENCE LISTING

<160> NUMBER OF SEQ ID NOS: 79

<210> SEQ ID NO 1
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: Misc_Feat
<222> LOCATION: (1)..(1)
<223> OTHER INFORMATION: AcNH is bound to Y (Tyrosine)
<220> FEATURE:
<221> NAME/KEY: Misc_Feat
<222> LOCATION: (8)..(8)
<223> OTHER INFORMATION: CONH2 is bound to L (Leucine)

<400> SEQUENCE: 1

Tyr Cys Gly Gly Gly Cys Ala Leu
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: AcNH is bound to Y (Tyrosine)
<220> FEATURE:
<221> NAME/KEY: misc_feature
<222> LOCATION: (8)..(8)
<223> OTHER INFORMATION: CONH2 is bound to L (Leucine)

<400> SEQUENCE: 2

Tyr Ser Gly Gly Gly Ser Ala Leu
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: AcNH is bound to Y (Tyrosine)
<220> FEATURE:
<221> NAME/KEY: misc_feature
<222> LOCATION: (8)..(8)
<223> OTHER INFORMATION: CONH2 is bound to L (Leucine)

<400> SEQUENCE: 3

Tyr Lys Gly Gly Gly Lys Ala Leu
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: AcNH is bound to F (Phenylalanine)
<220> FEATURE:
<221> NAME/KEY: misc_feature
<222> LOCATION: (9)..(9)

```
<223> OTHER INFORMATION: CONH2 is bound to A (Alanine)

<400> SEQUENCE: 4

Phe Lys Ala Cys Gly Lys Gly Cys Ala
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: CONH2 is bound to Y (Tyrosine)
<220> FEATURE:
<221> NAME/KEY: misc_feature
<222> LOCATION: (7)..(7)
<223> OTHER INFORMATION: AcNH is bound to A (Alanine)

<400> SEQUENCE: 5

Tyr Lys Gly Gly Gly Lys Ala Leu
1               5

<210> SEQ ID NO 6
<211> LENGTH: 10
<212> TYPE: PRT
<213> ORGANISM: Artificial Sequence
<220> FEATURE:
<223> OTHER INFORMATION: Synthetic sequence
<220> FEATURE:
<221> NAME/KEY: Misc_Feat
<222> LOCATION: (1)..(1)
<223> OTHER INFORMATION: AcNH is bound to F (Phenylalanine)
<220> FEATURE:
<221> NAME/KEY: MOD_RES
<222> LOCATION: (2)..(2)
<223> OTHER INFORMATION: The Cys residue is substituted with
      acetamidomethyl (Acm).
<220> FEATURE:
<221> NAME/KEY: MOD_RES
<222> LOCATION: (8)..(8)
<223> OTHER INFORMATION: The Cys residue is substituted with
      acetamidomethyl (Acm).
<220> FEATURE:
<221> NAME/KEY: Misc_Feat
<222> LOCATION: (10)..(10)
<223> OTHER INFORMATION: CONH2 is bound to L (Leucine)

<400> SEQUENCE: 6

Phe Cys Gly Gly Cys Gly Gly Cys Ala Leu
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: AcNH is bound to A (Alanine)
<220> FEATURE:
<221> NAME/KEY: misc_feature
<222> LOCATION: (10)..(10)
<223> OTHER INFORMATION: CONH2 is bound to T (Threonine)

<400> SEQUENCE: 7

Ala Cys Trp Gly Ser Ile Leu Ala Arg Thr
1               5                   10
```

<210> SEQ ID NO 8
<211> LENGTH: 10
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: AcNH is bound to A (Alanine)
<220> FEATURE:
<221> NAME/KEY: misc_feature
<222> LOCATION: (10)..(10)
<223> OTHER INFORMATION: CONH2 is bound to T (Threonine)

<400> SEQUENCE: 8

Ala Cys Tyr Gly Ser Ile Leu Ala Arg Thr
1               5                   10

<210> SEQ ID NO 9
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: AcNH is bound to F (Phenylalanine)
<220> FEATURE:
<221> NAME/KEY: misc_feature
<222> LOCATION: (8)..(8)
<223> OTHER INFORMATION: CONH2 is bound to L (Leucine)

<400> SEQUENCE: 9

Phe Cys Gly Gly Gly Cys Ala Leu
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: AcNH is bound to F (Phenylalanine)
<220> FEATURE:
<221> NAME/KEY: misc_feature
<222> LOCATION: (8)..(8)
<223> OTHER INFORMATION: CONH2 is bound to L (Leucine)

<400> SEQUENCE: 10

Phe Ser Gly Gly Gly Ser Ala Leu
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: CONH2 is bound to Y (Tyrosine)
<220> FEATURE:
<221> NAME/KEY: MOD_RES
<222> LOCATION: (2)..(2)
<223> OTHER INFORMATION: The Cys residue is substituted with a

```
        fluorinated heteroaromatic group.
<220> FEATURE:
<221> NAME/KEY: MISC_FEATURE
<222> LOCATION: (7)..(7)
<223> OTHER INFORMATION: AcNH is bound to A (Alanine)
<220> FEATURE:
<221> NAME/KEY: MOD_RES
<222> LOCATION: (8)..(8)
<223> OTHER INFORMATION: The Cys residue is substituted with a
        fluorinated heteroaromatic group.

<400> SEQUENCE: 11

Tyr Cys Gly Gly Gly Cys Ala Leu
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: CONH2 is bound to Y (TYROSINE)
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: AcNH is bound to A (Alanine)

<400> SEQUENCE: 12

Tyr Xaa Gly Gly Gly Xaa Ala Leu
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: MOD_RES
<222> LOCATION: (1)..(1)
<223> OTHER INFORMATION: The Tyr residue is substituted with a generic R
        group.
<220> FEATURE:
<221> NAME/KEY: misc_feature
<222> LOCATION: (1)..(1)
<223> OTHER INFORMATION: AcNH is bound to Y (Tyrosine)
<220> FEATURE:
<221> NAME/KEY: MOD_RES
<222> LOCATION: (2)..(2)
<223> OTHER INFORMATION: The Cys residue is substituted with a generic R
        group.
<220> FEATURE:
<221> NAME/KEY: MOD_RES
<222> LOCATION: (6)..(6)
<223> OTHER INFORMATION: The Cys residue is substituted with a generic R
        group.
<220> FEATURE:
<221> NAME/KEY: misc_feature
<222> LOCATION: (8)..(8)
<223> OTHER INFORMATION: CONH2 is bound to L (Leucine),

<400> SEQUENCE: 13

Tyr Cys Gly Gly Gly Cys Ala Leu
```

<210> SEQ ID NO 14
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: MOD_RES
<222> LOCATION: (1)..(1)
<223> OTHER INFORMATION: The Tyr residue is substituted with a
      fluorinated heteroaromatic group.
<220> FEATURE:
<221> NAME/KEY: misc_feature
<222> LOCATION: (1)..(1)
<223> OTHER INFORMATION: AcNH is bound to Y (Tyrosine)
<220> FEATURE:
<221> NAME/KEY: MOD_RES
<222> LOCATION: (2)..(2)
<223> OTHER INFORMATION: The Cys residue is substituted with a
      fluorinated heteroaromatic group.
<220> FEATURE:
<221> NAME/KEY: MOD_RES
<222> LOCATION: (6)..(6)
<223> OTHER INFORMATION: The Cys residue is substituted with a
      fluorinated heteroaromatic group.
<220> FEATURE:
<221> NAME/KEY: misc_feature
<222> LOCATION: (8)..(8)
<223> OTHER INFORMATION: CONH2 is bound to L (Leucine)

<400> SEQUENCE: 14

Tyr Cys Gly Gly Gly Cys Ala Leu
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: AcNH is bound to Y (Tyrosine)
<220> FEATURE:
<221> NAME/KEY: MOD_RES
<222> LOCATION: (2)..(2)
<223> OTHER INFORMATION: The Cys residue is substituted with a
      fluorinated heteroaromatic group.
<220> FEATURE:
<221> NAME/KEY: MOD_RES
<222> LOCATION: (6)..(6)
<223> OTHER INFORMATION: The Cys residue is substituted with a
      fluorinated heteroaromatic group.
<220> FEATURE:
<221> NAME/KEY: MISC_FEATURE
<222> LOCATION: (8)..(8)
<223> OTHER INFORMATION: CONH2 is bound to L (Leucine)

<400> SEQUENCE: 15

Tyr Cys Gly Gly Gly Cys Ala Leu
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(1)

```
<223> OTHER INFORMATION: AcNH is bound to Y (Tyrosine)
<220> FEATURE:
<221> NAME/KEY: MOD_RES
<222> LOCATION: (2)..(2)
<223> OTHER INFORMATION: The Cys residue is substituted with a
      fluorinated heteroaromatic group which is also bonded to the
      further Cys residue (6), thereby cyclising the peptide.
<220> FEATURE:
<221> NAME/KEY: MOD_RES
<222> LOCATION: (6)..(6)
<223> OTHER INFORMATION: The Cys residue is substituted with a
      fluorinated heteroaromatic group which is also bonded to the
      further Cys residue (2), thereby cyclising the peptide.
<220> FEATURE:
<221> NAME/KEY: MISC_FEATURE
<222> LOCATION: (8)..(8)
<223> OTHER INFORMATION: CONH2 is bound to L (Leucine).

<400> SEQUENCE: 16

Tyr Cys Gly Gly Gly Cys Ala Leu
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: AcNH is bound to Y (Tyrosine)
<220> FEATURE:
<221> NAME/KEY: MOD_RES
<222> LOCATION: (2)..(2)
<223> OTHER INFORMATION: The Cys residue is substituted with a
      fluorinated heteroaromatic group.
<220> FEATURE:
<221> NAME/KEY: MOD_RES
<222> LOCATION: (6)..(6)
<223> OTHER INFORMATION: The Cys residue is substituted with a
      fluorinated heteroaromatic group.
<220> FEATURE:
<221> NAME/KEY: MISC_FEATURE
<222> LOCATION: (8)..(8)
<223> OTHER INFORMATION: CONH2 is bound to L (Leucine).

<400> SEQUENCE: 17

Tyr Cys Gly Gly Gly Cys Ala Leu
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: AcNH is bound to Y (Tyrosine)
<220> FEATURE:
<221> NAME/KEY: MOD_RES
<222> LOCATION: (2)..(2)
<223> OTHER INFORMATION: The Cys residue is substituted with a
      fluorinated heteroaromatic group.
<220> FEATURE:
<221> NAME/KEY: MOD_RES
<222> LOCATION: (6)..(6)
<223> OTHER INFORMATION: The Cys residue is substituted with a
      fluorinated heteroaromatic group.
<220> FEATURE:
<221> NAME/KEY: MISC_FEATURE
<222> LOCATION: (8)..(8)
<223> OTHER INFORMATION: CONH2 is bound to L (Leucine).
```

```
<400> SEQUENCE: 18

Tyr Cys Gly Gly Gly Cys Ala Leu
1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (1)..(1)
<223> OTHER INFORMATION: AcNH is bound to Y (Tyrosine)
<220> FEATURE:
<221> NAME/KEY: MOD_RES
<222> LOCATION: (2)..(2)
<223> OTHER INFORMATION: The Cys residue is substituted with a
      chlorinated heteroaromatic group which is also bonded to the
      further Cys residue (6), thereby cyclising the peptide.
<220> FEATURE:
<221> NAME/KEY: MOD_RES
<222> LOCATION: (6)..(6)
<223> OTHER INFORMATION: The Cys residue is substituted with a
      chlorinated heteroaromatic group which is also bonded to the
      further Cys residue (2), thereby cyclising the peptide.
<220> FEATURE:
<221> NAME/KEY: Misc_feature
<222> LOCATION: (8)..(8)
<223> OTHER INFORMATION: CONH2 is bound to L (Leucine).

<400> SEQUENCE: 19

Tyr Cys Gly Gly Gly Cys Ala Leu
1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: AcNH is bound to Y (Tyrosine)
<220> FEATURE:
<221> NAME/KEY: MOD_RES
<222> LOCATION: (2)..(2)
<223> OTHER INFORMATION: The Cys residue is substituted with a
      haloginated heteroaromatic group.
<220> FEATURE:
<221> NAME/KEY: MOD_RES
<222> LOCATION: (6)..(6)
<223> OTHER INFORMATION: The Cys residue is substituted with a
      haloginated heteroaromatic group.
<220> FEATURE:
<221> NAME/KEY: misc_feature
<222> LOCATION: (8)..(8)
<223> OTHER INFORMATION: CONH2 is bound to L (Leucine).

<400> SEQUENCE: 20

Tyr Cys Gly Gly Gly Cys Ala Leu
1               5

<210> SEQ ID NO 21
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: MOD_RES
```

```
<222> LOCATION: (1)..(1)
<223> OTHER INFORMATION: The Tyr residue is substituted with a
      haloginated heteroaromatic group.
<220> FEATURE:
<221> NAME/KEY: misc_feature
<222> LOCATION: (1)..(1)
<223> OTHER INFORMATION: AcNH is bound to Y (Tyrosine)
<220> FEATURE:
<221> NAME/KEY: MOD_RES
<222> LOCATION: (2)..(2)
<223> OTHER INFORMATION: The Cys residue is substituted with a
      haloginated heteroaromatic group.
<220> FEATURE:
<221> NAME/KEY: MOD_RES
<222> LOCATION: (6)..(6)
<223> OTHER INFORMATION: The Cys residue is substituted with a
      haloginated heteroaromatic group.
<220> FEATURE:
<221> NAME/KEY: misc_feature
<222> LOCATION: (8)..(8)
<223> OTHER INFORMATION: CONH2 is bound to L (Leucine).

<400> SEQUENCE: 21

Tyr Cys Gly Gly Gly Cys Ala Leu
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: MOD_RES
<222> LOCATION: (1)..(1)
<223> OTHER INFORMATION: The Tyr residue is substituted with a
      haloginated heteroaromatic group.
<220> FEATURE:
<221> NAME/KEY: Misc_feature
<222> LOCATION: (1)..(1)
<223> OTHER INFORMATION: AcNH is bound to Y (Tyrosine)
<220> FEATURE:
<221> NAME/KEY: MOD_RES
<222> LOCATION: (2)..(2)
<223> OTHER INFORMATION: The Cys residue is substituted with a
      haloginated heteroaromatic group.
<220> FEATURE:
<221> NAME/KEY: MOD_RES
<222> LOCATION: (6)..(6)
<223> OTHER INFORMATION: The Cys residue is substituted with a
      haloginated heteroaromatic group.
<220> FEATURE:
<221> NAME/KEY: Misc_feature
<222> LOCATION: (8)..(8)
<223> OTHER INFORMATION: CONH2 is bound to L (Leucine).

<400> SEQUENCE: 22

Tyr Cys Gly Gly Gly Cys Ala Leu
1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: MOD_RES
<222> LOCATION: (2)..(2)
<223> OTHER INFORMATION: The Cys residue is substituted with a
      fluorinated heteroaromatic group which is also bonded to the
      further Cys residue (6), thereby cyclising the peptide.
<220> FEATURE:
<221> NAME/KEY: MOD_RES
<222> LOCATION: (6)..(6)
```

<223> OTHER INFORMATION: The Cys residue is substituted with a
      fluorinated heteroaromatic group which is also bonded to the
      further Cys residue (2), thereby cyclising the peptide.

<400> SEQUENCE: 23

Tyr Cys Gly Gly Gly Cys Ala Leu
1               5

<210> SEQ ID NO 24
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (1)..(1)
<223> OTHER INFORMATION: AcNH is bound to Y (Tyrosine)
<220> FEATURE:
<221> NAME/KEY: MOD_RES
<222> LOCATION: (2)..(2)
<223> OTHER INFORMATION: The Ser residue is substituted with a
      fluorinated bicyclic heteroaromatic group.
<220> FEATURE:
<221> NAME/KEY: MOD_RES
<222> LOCATION: (6)..(6)
<223> OTHER INFORMATION: The Cys residue is substituted with a
      fluorinated bicyclic heteroaromatic group.
<220> FEATURE:
<221> NAME/KEY: Misc_feature
<222> LOCATION: (8)..(8)
<223> OTHER INFORMATION: CONH2 is bound to L (Leucine).

<400> SEQUENCE: 24

Tyr Ser Gly Gly Gly Ser Ala Leu
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: MOD_RES
<222> LOCATION: (1)..(1)
<223> OTHER INFORMATION: The Tyr residue is substituted with a generic R
      group.
<220> FEATURE:
<221> NAME/KEY: misc_feature
<222> LOCATION: (1)..(1)
<223> OTHER INFORMATION: AcNH is bound to Y (Tyrosine)
<220> FEATURE:
<221> NAME/KEY: misc_feature
<222> LOCATION: (8)..(8)
<223> OTHER INFORMATION: CONH2 is bound to L (Leucine).

<400> SEQUENCE: 25

Tyr Ser Gly Gly Gly Ser Ala Leu
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: MOD_RES
<222> LOCATION: (1)..(1)
<223> OTHER INFORMATION: The Tyr residue is substituted with a
      fluorinated heteroaromatic group.
<220> FEATURE:

```
<221> NAME/KEY: Misc_feature
<222> LOCATION: (1)..(1)
<223> OTHER INFORMATION: AcNH is bound to Y (Tyrosine)
<220> FEATURE:
<221> NAME/KEY: Misc_feature
<222> LOCATION: (8)..(8)
<223> OTHER INFORMATION: CONH2 is bound to L (Leucine).

<400> SEQUENCE: 26

Tyr Ser Gly Gly Gly Ser Ala Leu
1               5

<210> SEQ ID NO 27
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: MOD_RES
<222> LOCATION: (1)..(1)
<223> OTHER INFORMATION: The Tyr residue is substituted with a
      fluorinated heteroaromatic group.
<220> FEATURE:
<221> NAME/KEY: Misc_feature
<222> LOCATION: (1)..(1)
<223> OTHER INFORMATION: AcNH is bound to Y (Tyrosine)
<220> FEATURE:
<221> NAME/KEY: MOD_RES
<222> LOCATION: (2)..(2)
<223> OTHER INFORMATION: The Ser residue is substituted with a
      fluorinated heteroaromatic group which is also bonded to the
      further Ser residue (6), thereby cyclising the peptide.
<220> FEATURE:
<221> NAME/KEY: MOD_RES
<222> LOCATION: (6)..(6)
<223> OTHER INFORMATION: The Ser residue is substituted with a
      fluorinated heteroaromatic group which is also bonded to the
      further Ser residue (2), thereby cyclising the peptide.
<220> FEATURE:
<221> NAME/KEY: Misc_feature
<222> LOCATION: (8)..(8)
<223> OTHER INFORMATION: CONH2 is bound to L (Leucine).

<400> SEQUENCE: 27

Tyr Ser Gly Gly Gly Ser Ala Leu
1               5

<210> SEQ ID NO 28
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: AcNH is bound to Y (Tyrosine)
<220> FEATURE:
<221> NAME/KEY: MOD_RES
<222> LOCATION: (2)..(2)
<223> OTHER INFORMATION: The Ser residue is substituted with a
      fluorinated heteroaromatic group.
<220> FEATURE:
<221> NAME/KEY: misc_feature
<222> LOCATION: (8)..(8)
<223> OTHER INFORMATION: nd CONH2 is bound to L (Leucine).

<400> SEQUENCE: 28

Tyr Ser Gly Gly Gly Ser Ala Leu
1               5

<210> SEQ ID NO 29
```

```
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (1)..(1)
<223> OTHER INFORMATION: AcNH is bound to Y (Tyrosine)
<220> FEATURE:
<221> NAME/KEY: MOD_RES
<222> LOCATION: (2)..(2)
<223> OTHER INFORMATION: The Ser residue is substituted with a
      fluorinated heteroaromatic group.
<220> FEATURE:
<221> NAME/KEY: MOD_RES
<222> LOCATION: (6)..(6)
<223> OTHER INFORMATION: The Ser residue is substituted with a
      fluorinated heteroaromatic group.
<220> FEATURE:
<221> NAME/KEY: misc_feature
<222> LOCATION: (8)..(8)
<223> OTHER INFORMATION: CONH2 is bound to L (Leucine).

<400> SEQUENCE: 29

Tyr Ser Gly Gly Gly Ser Ala Leu
1               5

<210> SEQ ID NO 30
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: MOD_RES
<222> LOCATION: (1)..(1)
<223> OTHER INFORMATION: The Tyr residue is substituted with a
      fluorinated heteroaromatic group.
<220> FEATURE:
<221> NAME/KEY: Misc_feature
<222> LOCATION: (1)..(1)
<223> OTHER INFORMATION: AcNH is bound to Y (Tyrosine)
<220> FEATURE:
<221> NAME/KEY: MOD_RES
<222> LOCATION: (2)..(2)
<223> OTHER INFORMATION: The Ser residue is substituted with a
      fluorinated heteroaromatic group.
<220> FEATURE:
<221> NAME/KEY: MOD_RES
<222> LOCATION: (6)..(6)
<223> OTHER INFORMATION: The Ser residue is substituted with a
      fluorinated heteroaromatic group.
<220> FEATURE:
<221> NAME/KEY: Misc_feature
<222> LOCATION: (8)..(8)
<223> OTHER INFORMATION: CONH2 is bound to L (Leucine).

<400> SEQUENCE: 30

Tyr Ser Gly Gly Gly Ser Ala Leu
1               5

<210> SEQ ID NO 31
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (1)..(1)
<223> OTHER INFORMATION: AcNH is bound to Y (Tyrosine)
<220> FEATURE:
<221> NAME/KEY: MOD_RES
<222> LOCATION: (2)..(2)
```

<223> OTHER INFORMATION: The Ser residue is substituted with a
      fluorinated heteroaromatic group which is also bonded to the
      further Ser residue (6), thereby cyclising the peptide.
<220> FEATURE:
<221> NAME/KEY: MOD_RES
<222> LOCATION: (6)..(6)
<223> OTHER INFORMATION: The Ser residue is substituted with a
      fluorinated heteroaromatic group which is also bonded to the
      further Ser residue (2), thereby cyclising the peptide.
<220> FEATURE:
<221> NAME/KEY: Misc_feature
<222> LOCATION: (8)..(8)
<223> OTHER INFORMATION: CONH2 is bound to L (Leucine).

<400> SEQUENCE: 31

Tyr Ser Gly Gly Gly Ser Ala Leu
1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (1)..(1)
<223> OTHER INFORMATION: AcNH is bound to Y (Tyrosine)
<220> FEATURE:
<221> NAME/KEY: MOD_RES
<222> LOCATION: (2)..(2)
<223> OTHER INFORMATION: The Ser residue is substituted with a
      haloginated heteroaromatic group.
<220> FEATURE:
<221> NAME/KEY: Misc_feature
<222> LOCATION: (8)..(8)
<223> OTHER INFORMATION: CONH2 is bound to L (Leucine).

<400> SEQUENCE: 32

Tyr Ser Gly Gly Gly Ser Ala Leu
1               5

<210> SEQ ID NO 33
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (1)..(1)
<223> OTHER INFORMATION: AcNH is bound to Y (Tyrosine)
<220> FEATURE:
<221> NAME/KEY: MOD_RES
<222> LOCATION: (2)..(2)
<223> OTHER INFORMATION: The Ser residue is substituted with a
      haloginated heteroaromatic group.
<220> FEATURE:
<221> NAME/KEY: MOD_RES
<222> LOCATION: (6)..(6)
<223> OTHER INFORMATION: The Ser residue is substituted with a
      haloginated heteroaromatic group.
<220> FEATURE:
<221> NAME/KEY: Misc_feature
<222> LOCATION: (8)..(8)
<223> OTHER INFORMATION: CONH2 is bound to L (Leucine).

<400> SEQUENCE: 33

Tyr Ser Gly Gly Gly Ser Ala Leu
1               5

<210> SEQ ID NO 34
<211> LENGTH: 8

```
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: AcNH is bound to Y (Tyrosine)
<220> FEATURE:
<221> NAME/KEY: MOD_RES
<222> LOCATION: (2)..(2)
<223> OTHER INFORMATION: The Ser residue is substituted with a
      haloginated heteroaromatic group.
<220> FEATURE:
<221> NAME/KEY: MISC_FEATURE
<222> LOCATION: (8)..(8)
<223> OTHER INFORMATION: CONH2 is bound to L (Leucine).

<400> SEQUENCE: 34

Tyr Ser Gly Gly Gly Ser Ala Leu
1               5

<210> SEQ ID NO 35
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (1)..(1)
<223> OTHER INFORMATION: AcNH is bound to Y (Tyrosine)
<220> FEATURE:
<221> NAME/KEY: MOD_RES
<222> LOCATION: (2)..(2)
<223> OTHER INFORMATION: The Ser residue is substituted with a
      haloginated heteroaromatic group.
<220> FEATURE:
<221> NAME/KEY: MOD_RES
<222> LOCATION: (6)..(6)
<223> OTHER INFORMATION: The Ser residue is substituted with a
      haloginated heteroaromatic group.
<220> FEATURE:
<221> NAME/KEY: Misc_feature
<222> LOCATION: (8)..(8)
<223> OTHER INFORMATION: CONH2 is bound to L (Leucine).

<400> SEQUENCE: 35

Tyr Ser Gly Gly Gly Ser Ala Leu
1               5

<210> SEQ ID NO 36
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: MOD_RES
<222> LOCATION: (1)..(1)
<223> OTHER INFORMATION: The Tyr residue is substituted with a generic R
      group.
<220> FEATURE:
<221> NAME/KEY: Misc_feature
<222> LOCATION: (1)..(1)
<223> OTHER INFORMATION: AcNH is bound to Y (Tyrosine)
<220> FEATURE:
<221> NAME/KEY: MOD_RES
<222> LOCATION: (2)..(2)
<223> OTHER INFORMATION: The Lys residue is substituted with a generic R
      group.
<220> FEATURE:
<221> NAME/KEY: MOD_RES
<222> LOCATION: (6)..(6)
<223> OTHER INFORMATION: The Lys residue is substituted with a generic R
```

```
          group.
<220> FEATURE:
<221> NAME/KEY: Misc_feature
<222> LOCATION: (8)..(8)
<223> OTHER INFORMATION: CONH2 is bound to L (Leucine).

<400> SEQUENCE: 36

Tyr Lys Gly Gly Gly Lys Ala Leu
1               5

<210> SEQ ID NO 37
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: MOD_RES
<222> LOCATION: (1)..(1)
<223> OTHER INFORMATION: The Tyr residue is substituted with a
      fluorinated heteroaromatic group.
<220> FEATURE:
<221> NAME/KEY: Misc_feature
<222> LOCATION: (1)..(1)
<223> OTHER INFORMATION: AcNH is bound to Y (Tyrosine)
<220> FEATURE:
<221> NAME/KEY: MOD_RES
<222> LOCATION: (2)..(2)
<223> OTHER INFORMATION: The Lys residue is substituted with a
      fluorinated heteroaromatic group.
<220> FEATURE:
<221> NAME/KEY: MOD_RES
<222> LOCATION: (6)..(6)
<223> OTHER INFORMATION: The Lys residue is substituted with a
      fluorinated heteroaromatic group.
<220> FEATURE:
<221> NAME/KEY: Misc_feature
<222> LOCATION: (8)..(8)
<223> OTHER INFORMATION: CONH2 is bound to L (Leucine).

<400> SEQUENCE: 37

Tyr Lys Gly Gly Gly Lys Ala Leu
1               5

<210> SEQ ID NO 38
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (1)..(1)
<223> OTHER INFORMATION: AcNH is bound to Y (Tyrosine)
<220> FEATURE:
<221> NAME/KEY: MOD_RES
<222> LOCATION: (2)..(2)
<223> OTHER INFORMATION: The Lys residue is substituted with a
      fluorinated heteroaromatic group.
<220> FEATURE:
<221> NAME/KEY: MOD_RES
<222> LOCATION: (6)..(6)
<223> OTHER INFORMATION: The Lys residue is substituted with a
      fluorinated heteroaromatic group.
<220> FEATURE:
<221> NAME/KEY: Misc_feature
<222> LOCATION: (8)..(8)
<223> OTHER INFORMATION: CONH2 is bound to L (Leucine).

<400> SEQUENCE: 38

Tyr Lys Gly Gly Gly Lys Ala Leu
1               5
```

```
<210> SEQ ID NO 39
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: MOD_RES
<222> LOCATION: (1)..(1)
<223> OTHER INFORMATION: The Tyr residue is substituted with a
      fluorinated heteroaromatic group.
<220> FEATURE:
<221> NAME/KEY: Misc_feature
<222> LOCATION: (1)..(1)
<223> OTHER INFORMATION: AcNH is bound to Y (Tyrosine)
<220> FEATURE:
<221> NAME/KEY: MOD_RES
<222> LOCATION: (2)..(2)
<223> OTHER INFORMATION: The Lys residue is substituted with a
      fluorinated heteroaromatic group.
<220> FEATURE:
<221> NAME/KEY: MOD_RES
<222> LOCATION: (6)..(6)
<223> OTHER INFORMATION: The Lys residue is substituted with a
      fluorinated heteroaromatic group.
<220> FEATURE:
<221> NAME/KEY: Misc_feature
<222> LOCATION: (8)..(8)
<223> OTHER INFORMATION: CONH2 is bound to L (Leucine).

<400> SEQUENCE: 39

Tyr Lys Gly Gly Gly Lys Ala Leu
1               5

<210> SEQ ID NO 40
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (1)..(1)
<223> OTHER INFORMATION: AcNH is bound to Y (Tyrosine)
<220> FEATURE:
<221> NAME/KEY: MOD_RES
<222> LOCATION: (2)..(2)
<223> OTHER INFORMATION: The Lys residue is substituted with a
      fluorinated bicyclic heteroaromatic group.
<220> FEATURE:
<221> NAME/KEY: MOD_RES
<222> LOCATION: (6)..(6)
<223> OTHER INFORMATION: The Lys residue is substituted with a
      fluorinated bicyclic heteroaromatic group.
<220> FEATURE:
<221> NAME/KEY: Misc_feature
<222> LOCATION: (8)..(8)
<223> OTHER INFORMATION: CONH2 is bound to L (Leucine).

<400> SEQUENCE: 40

Tyr Lys Gly Gly Gly Lys Ala Leu
1               5

<210> SEQ ID NO 41
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: MIsc_feature
<222> LOCATION: (1)..(1)
<223> OTHER INFORMATION: AcNH is bound to Y (Tyrosine)
<220> FEATURE:
<221> NAME/KEY: MOD_RES
```

```
<222> LOCATION: (2)..(2)
<223> OTHER INFORMATION: The Lys residue is substituted with a
      fluorinated heteroaromatic group.
<220> FEATURE:
<221> NAME/KEY: MOD_RES
<222> LOCATION: (6)..(6)
<223> OTHER INFORMATION: The Lys residue is substituted with a
      fluorinated heteroaromatic group.
<220> FEATURE:
<221> NAME/KEY: MIsc_feature
<222> LOCATION: (8)..(8)
<223> OTHER INFORMATION: CONH2 is bound to L (Leucine).

<400> SEQUENCE: 41

Tyr Lys Gly Gly Gly Lys Ala Leu
1               5

<210> SEQ ID NO 42
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (1)..(1)
<223> OTHER INFORMATION: AcNH is bound to Y (Tyrosine)
<220> FEATURE:
<221> NAME/KEY: MOD_RES
<222> LOCATION: (2)..(2)
<223> OTHER INFORMATION: The Lys residue is substituted with a
      haloginated heteroaromatic group.
<220> FEATURE:
<221> NAME/KEY: MOD_RES
<222> LOCATION: (6)..(6)
<223> OTHER INFORMATION: The Lys residue is substituted with a
      haloginated heteroaromatic group.
<220> FEATURE:
<221> NAME/KEY: Misc_feature
<222> LOCATION: (8)..(8)
<223> OTHER INFORMATION: CONH2 is bound to L (Leucine).

<400> SEQUENCE: 42

Tyr Lys Gly Gly Gly Lys Ala Leu
1               5

<210> SEQ ID NO 43
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (1)..(1)
<223> OTHER INFORMATION: AcNH is bound to Y (Tyrosine)
<220> FEATURE:
<221> NAME/KEY: MOD_RES
<222> LOCATION: (2)..(2)
<223> OTHER INFORMATION: The Lys residue is substituted with a
      haloginated heteroaromatic group.
<220> FEATURE:
<221> NAME/KEY: MOD_RES
<222> LOCATION: (6)..(6)
<223> OTHER INFORMATION: The Lys residue is substituted with a
      haloginated heteroaromatic group.
<220> FEATURE:
<221> NAME/KEY: Misc_feature
<222> LOCATION: (8)..(8)
<223> OTHER INFORMATION: CONH2 is bound to L (Leucine).

<400> SEQUENCE: 43

Tyr Lys Gly Gly Gly Lys Ala Leu
1               5
```

```
<210> SEQ ID NO 44
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: MOD_RES
<222> LOCATION: (1)..(1)
<223> OTHER INFORMATION: The Tyr residue is substituted with a
      haloginated heteroaromatic group.
<220> FEATURE:
<221> NAME/KEY: misc_feature
<222> LOCATION: (1)..(1)
<223> OTHER INFORMATION: AcNH is bound to Y (Tyrosine)
<220> FEATURE:
<221> NAME/KEY: MOD_RES
<222> LOCATION: (2)..(2)
<223> OTHER INFORMATION: The Lys residue is substituted with a
      haloginated heteroaromatic group.
<220> FEATURE:
<221> NAME/KEY: MOD_RES
<222> LOCATION: (6)..(6)
<223> OTHER INFORMATION: The Lys residue is substituted with a
      haloginated heteroaromatic group.
<220> FEATURE:
<221> NAME/KEY: misc_feature
<222> LOCATION: (8)..(8)
<223> OTHER INFORMATION: CONH2 is bound to L (Leucine).

<400> SEQUENCE: 44

Tyr Lys Gly Gly Gly Lys Ala Leu
1               5

<210> SEQ ID NO 45
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: AcNH is bound to Y (Tyrosine)
<220> FEATURE:
<221> NAME/KEY: MOD_RES
<222> LOCATION: (2)..(2)
<223> OTHER INFORMATION: The Lys residue is substituted with a
      haloginated heteroaromatic group.
<220> FEATURE:
<221> NAME/KEY: MOD_RES
<222> LOCATION: (6)..(6)
<223> OTHER INFORMATION: The Lys residue is substituted with a
      haloginated heteroaromatic group.
<220> FEATURE:
<221> NAME/KEY: misc_feature
<222> LOCATION: (8)..(8)
<223> OTHER INFORMATION: CONH2 is bound to L (Leucine).

<400> SEQUENCE: 45

Tyr Lys Gly Gly Gly Lys Ala Leu
1               5

<210> SEQ ID NO 46
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: MOD_RES
<222> LOCATION: (1)..(1)
<223> OTHER INFORMATION: The Tyr residue is substituted with a
```

```
      haloginated heteroaromatic group.
<220> FEATURE:
<221> NAME/KEY: misc_feature
<222> LOCATION: (1)..(1)
<223> OTHER INFORMATION: AcNH is bound to Y (Tyrosine)
<220> FEATURE:
<221> NAME/KEY: MOD_RES
<222> LOCATION: (2)..(2)
<223> OTHER INFORMATION: The Lys residue is substituted with a
      haloginated heteroaromatic group.
<220> FEATURE:
<221> NAME/KEY: MOD_RES
<222> LOCATION: (6)..(6)
<223> OTHER INFORMATION: The Lys residue is substituted with a
      haloginated heteroaromatic group.
<220> FEATURE:
<221> NAME/KEY: misc_feature
<222> LOCATION: (8)..(8)
<223> OTHER INFORMATION: CONH2 is bound to L (Leucine).

<400> SEQUENCE: 46

Tyr Lys Gly Gly Gly Lys Ala Leu
1               5

<210> SEQ ID NO 47
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: CONH2 is bound to Y (Tyrosine)
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MOD_RES
<222> LOCATION: (2)..(2)
<223> OTHER INFORMATION: The amino acid residue is substituted with a
      generic Y group.
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: MOD_RES
<222> LOCATION: (6)..(6)
<223> OTHER INFORMATION: The amino acid residue is substituted with a
      generic Z group.
<220> FEATURE:
<221> NAME/KEY: misc_feature
<222> LOCATION: (7)..(7)
<223> OTHER INFORMATION: ACNH is bound to A (Alanine)

<400> SEQUENCE: 47

Tyr Xaa Gly Gly Gly Xaa Ala Leu
1               5

<210> SEQ ID NO 48
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: AcNH is bound to Y (Tyrosine)
<220> FEATURE:
<221> NAME/KEY: MOD_RES
<222> LOCATION: (2)..(2)
<223> OTHER INFORMATION: The Cys residue is substituted with a generic R
```

```
            group.
<220> FEATURE:
<221> NAME/KEY: MOD_RES
<222> LOCATION: (6)..(6)
<223> OTHER INFORMATION: The Cys residue is substituted with a generic R
      group.
<220> FEATURE:
<221> NAME/KEY: misc_feature
<222> LOCATION: (8)..(8)
<223> OTHER INFORMATION: CONH2 is bound to L (Leucine).

<400> SEQUENCE: 48

Tyr Cys Gly Gly Gly Cys Ala Leu
1               5

<210> SEQ ID NO 49
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: AcNH is bound to Y (Tyrosine)
<220> FEATURE:
<221> NAME/KEY: MOD_RES
<222> LOCATION: (2)..(2)
<223> OTHER INFORMATION: The Cys residue is substituted with a
      fluorinated heteroaromatic group.
<220> FEATURE:
<221> NAME/KEY: MOD_RES
<222> LOCATION: (6)..(6)
<223> OTHER INFORMATION: The Cys residue is substituted with a
      fluorinated heteroaromatic group.
<220> FEATURE:
<221> NAME/KEY: misc_feature
<222> LOCATION: (8)..(8)
<223> OTHER INFORMATION: CONH2 is bound to L (Leucine).

<400> SEQUENCE: 49

Tyr Cys Gly Gly Gly Cys Ala Leu
1               5

<210> SEQ ID NO 50
<211> LENGTH: 9
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: AcNH is bound to first Phe residue
<220> FEATURE:
<221> NAME/KEY: MOD_RES
<222> LOCATION: (4)..(4)
<223> OTHER INFORMATION: The Cys residue is substituted with a
      fluorinated heteroaromatic group.
<220> FEATURE:
<221> NAME/KEY: MOD_RES
<222> LOCATION: (8)..(8)
<223> OTHER INFORMATION: The Cys residue is substituted with a
      fluorinated heteroaromatic group.
<220> FEATURE:
<221> NAME/KEY: misc_feature
<222> LOCATION: (9)..(9)
<223> OTHER INFORMATION: CONH2 is bound to terminal Ala residue.

<400> SEQUENCE: 50

Phe Lys Ala Cys Gly Lys Gly Cys Ala
1               5
```

```
<210> SEQ ID NO 51
<211> LENGTH: 9
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: AcNH is bound to first Phe residue (1)
<220> FEATURE:
<221> NAME/KEY: MOD_RES
<222> LOCATION: (2)..(2)
<223> OTHER INFORMATION: The Lys residue is substituted with a
      fluorinated heteroaromatic group.
<220> FEATURE:
<221> NAME/KEY: MOD_RES
<222> LOCATION: (4)..(4)
<223> OTHER INFORMATION: The Cys residue is substituted with a
      fluorinated heteroaromatic group.
<220> FEATURE:
<221> NAME/KEY: MOD_RES
<222> LOCATION: (6)..(6)
<223> OTHER INFORMATION: The Lys residue is substituted with a
      fluorinated heteroaromatic group.
<220> FEATURE:
<221> NAME/KEY: MOD_RES
<222> LOCATION: (8)..(8)
<223> OTHER INFORMATION: The Cys residue is substituted with a
      fluorinated heteroaromatic group.
<220> FEATURE:
<221> NAME/KEY: misc_feature
<222> LOCATION: (9)..(9)
<223> OTHER INFORMATION: CONH2 is bound to terminal Ala residue (9).

<400> SEQUENCE: 51

Phe Lys Ala Cys Gly Lys Gly Cys Ala
1               5

<210> SEQ ID NO 52
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: MOD_RES
<222> LOCATION: (1)..(1)
<223> OTHER INFORMATION: The Tyr residue is substituted with a
      fluorinated heteroaromatic group.
<220> FEATURE:
<221> NAME/KEY: misc_feature
<222> LOCATION: (1)..(1)
<223> OTHER INFORMATION: AcNH is bound to Y (Tyrosine)
<220> FEATURE:
<221> NAME/KEY: MOD_RES
<222> LOCATION: (2)..(2)
<223> OTHER INFORMATION: The Cys residue is substituted with a
      fluorinated heteroaromatic group which is also bonded to the
      further Cys residue (6), thereby cyclising the peptide.
<220> FEATURE:
<221> NAME/KEY: MOD_RES
<222> LOCATION: (6)..(6)
<223> OTHER INFORMATION: The Cys residue is substituted with a
      fluorinated heteroaromatic group which is also bonded to the
      further Cys residue (6), thereby cyclising the peptide.
<220> FEATURE:
<221> NAME/KEY: misc_feature
<222> LOCATION: (8)..(8)
<223> OTHER INFORMATION: CONH2 is bound to L (Leucine).

<400> SEQUENCE: 52

Tyr Cys Gly Gly Gly Cys Ala Leu
1               5
```

```
<210> SEQ ID NO 53
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: MOD_RES
<222> LOCATION: (1)..(1)
<223> OTHER INFORMATION: The Tyr residue is substituted with a
      fluorinated heteroaromatic group.
<220> FEATURE:
<221> NAME/KEY: misc_feature
<222> LOCATION: (1)..(1)
<223> OTHER INFORMATION: AcNH is bound to Y (Tyrosine)
<220> FEATURE:
<221> NAME/KEY: MOD_RES
<222> LOCATION: (2)..(2)
<223> OTHER INFORMATION: The Cys residue is substituted with a
      fluorinated heteroaromatic group which is also bonded to the
      further Cys residue (6), thereby cyclising the peptide.
<220> FEATURE:
<221> NAME/KEY: MOD_RES
<222> LOCATION: (6)..(6)
<223> OTHER INFORMATION: The Cys residue is substituted with a
      fluorinated heteroaromatic group which is also bonded to the
      further Cys residue (6), thereby cyclising the peptide.
<220> FEATURE:
<221> NAME/KEY: misc_feature
<222> LOCATION: (8)..(8)
<223> OTHER INFORMATION: CONH2 is bound to L (Leucine).

<400> SEQUENCE: 53

Tyr Cys Gly Gly Gly Cys Ala Leu
1               5

<210> SEQ ID NO 54
<211> LENGTH: 10
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: AcNH is bound to first Phe residue (1)
<220> FEATURE:
<221> NAME/KEY: MOD_RES
<222> LOCATION: (2)..(2)
<223> OTHER INFORMATION: The Cys residue is substituted with
      acetamidomethyl (Acm).
<220> FEATURE:
<221> NAME/KEY: MOD_RES
<222> LOCATION: (5)..(5)
<223> OTHER INFORMATION: The Cys residue is substituted with a
      fluorinated heteroaromatic group.
<220> FEATURE:
<221> NAME/KEY: MOD_RES
<222> LOCATION: (8)..(8)
<223> OTHER INFORMATION: The Cys residue is substituted with
      acetamidomethyl (Acm).
<220> FEATURE:
<221> NAME/KEY: misc_feature
<222> LOCATION: (10)..(10)
<223> OTHER INFORMATION: CONH2 is bound to terminal Leu residue (10).

<400> SEQUENCE: 54

Phe Cys Gly Gly Cys Gly Gly Cys Ala Leu
1               5                   10

<210> SEQ ID NO 55
<211> LENGTH: 10
<212> TYPE: PRT
<213> ORGANISM: Artificial Sequence
<220> FEATURE:
```

```
<223> OTHER INFORMATION: Synthetic sequence
<220> FEATURE:
<221> NAME/KEY: misc_feature
<222> LOCATION: (1)..(1)
<223> OTHER INFORMATION: AcNH is bound to first Phe residue (1)
<220> FEATURE:
<221> NAME/KEY: MOD_RES
<222> LOCATION: (2)..(2)
<223> OTHER INFORMATION: The Cys residue is substituted with
      acetamidomethyl (Acm).
<220> FEATURE:
<221> NAME/KEY: MOD_RES
<222> LOCATION: (5)..(5)
<223> OTHER INFORMATION: The Cys residue is substituted with a
      fluorinated heteroaromatic group.
<220> FEATURE:
<221> NAME/KEY: MOD_RES
<222> LOCATION: (8)..(8)
<223> OTHER INFORMATION: The Cys residue is substituted with
      acetamidomethyl (Acm).
<220> FEATURE:
<221> NAME/KEY: misc_feature
<222> LOCATION: (10)..(10)
<223> OTHER INFORMATION: CONH2 is bound to terminal Leu residue (10).

<400> SEQUENCE: 55

Phe Cys Gly Gly Cys Gly Gly Cys Ala Leu
1               5                   10

<210> SEQ ID NO 56
<211> LENGTH: 10
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: AcNH is bound to Ala residue (1)
<220> FEATURE:
<221> NAME/KEY: MOD_RES
<222> LOCATION: (2)..(2)
<223> OTHER INFORMATION: The Cys residue is substituted with a
      fluorinated heteroaromatic group which is also bonded to the
      further Ser residue (5), thereby cyclising the peptide.
<220> FEATURE:
<221> NAME/KEY: MOD_RES
<222> LOCATION: (5)..(5)
<223> OTHER INFORMATION: The Ser residue is substituted with a
      fluorinated heteroaromatic group which is also bonded to the
      further Cys residue (2), thereby cyclising the peptide.
<220> FEATURE:
<221> NAME/KEY: misc_feature
<222> LOCATION: (10)..(10)
<223> OTHER INFORMATION: CONH2 is bound to Thr residue (10).

<400> SEQUENCE: 56

Ala Cys Trp Gly Ser Ile Leu Ala Arg Thr
1               5                   10

<210> SEQ ID NO 57
<211> LENGTH: 10
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: AcNH is bound to Ala residue (1)
<220> FEATURE:
<221> NAME/KEY: MOD_RES
<222> LOCATION: (2)..(2)
<223> OTHER INFORMATION: The Cys residue is substituted with a
      fluorinated heteroaromatic group which is also bonded to the
```

```
          further Tyr residue (3), thereby cyclising the peptide.
<220> FEATURE:
<221> NAME/KEY: MOD_RES
<222> LOCATION: (3)..(3)
<223> OTHER INFORMATION: The Tyr residue is substituted with a
          fluorinated heteroaromatic group which is also bonded to the
          further Cys residue (2), thereby cyclising the peptide.
<220> FEATURE:
<221> NAME/KEY: misc_feature
<222> LOCATION: (10)..(10)
<223> OTHER INFORMATION: CONH2 is bound to Thr residue (10).

<400> SEQUENCE: 57

Ala Cys Tyr Gly Ser Ile Leu Ala Arg Thr
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: AcNH is bound to Ala residue (1)
<220> FEATURE:
<221> NAME/KEY: MOD_RES
<222> LOCATION: (2)..(2)
<223> OTHER INFORMATION: The Cys residue is substituted with a
          haloginated heteroaromatic group.
<220> FEATURE:
<221> NAME/KEY: MOD_RES
<222> LOCATION: (3)..(3)
<223> OTHER INFORMATION: The Tyr residue is substituted with a
          haloginated heteroaromatic group.
<220> FEATURE:
<221> NAME/KEY: MOD_RES
<222> LOCATION: (5)..(5)
<223> OTHER INFORMATION: The Ser residue is substituted with a
          haloginated heteroaromatic group.
<220> FEATURE:
<221> NAME/KEY: misc_feature
<222> LOCATION: (10)..(10)
<223> OTHER INFORMATION: CONH2 is bound to Thr residue (10).
<220> FEATURE:
<221> NAME/KEY: MOD_RES
<222> LOCATION: (10)..(10)
<223> OTHER INFORMATION: The Thr residue is substituted with a
          haloginated heteroaromatic group.

<400> SEQUENCE: 58

Ala Cys Tyr Gly Ser Ile Leu Ala Arg Thr
1               5                   10

<210> SEQ ID NO 59
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: AcNH is bound to Phe residue (1)
<220> FEATURE:
<221> NAME/KEY: MOD_RES
<222> LOCATION: (2)..(2)
<223> OTHER INFORMATION: The Cys residue is substituted with a
          fluorinated heteroaromatic group which is also bonded to the
          further Cys residue (6), thereby cyclising the peptide.
<220> FEATURE:
<221> NAME/KEY: MOD_RES
<222> LOCATION: (6)..(6)
<223> OTHER INFORMATION: The Cys residue is substituted with a
```

```
        fluorinated heteroaromatic group which is also bonded to the
        further Cys residue (2), thereby cyclising the peptide.
<220> FEATURE:
<221> NAME/KEY: misc_feature
<222> LOCATION: (8)..(8)
<223> OTHER INFORMATION: CONH2 is bound to Leu residue (8).

<400> SEQUENCE: 59

Phe Cys Gly Gly Gly Cys Ala Leu
1               5

<210> SEQ ID NO 60
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: AcNH is bound to Phe residue (1)
<220> FEATURE:
<221> NAME/KEY: MOD_RES
<222> LOCATION: (2)..(2)
<223> OTHER INFORMATION: The Cys residue is substituted with a
        fluorinated bicyclic heteroaromatic group.
<220> FEATURE:
<221> NAME/KEY: MOD_RES
<222> LOCATION: (6)..(6)
<223> OTHER INFORMATION: The Cys residue is substituted with a
        fluorinated bicyclic heteroaromatic group.
<220> FEATURE:
<221> NAME/KEY: misc_feature
<222> LOCATION: (8)..(8)
<223> OTHER INFORMATION: CONH2 is bound to Leu residue (8).

<400> SEQUENCE: 60

Phe Cys Gly Gly Gly Cys Ala Leu
1               5

<210> SEQ ID NO 61
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: AcNH is bound to Phe residue (1)
<220> FEATURE:
<221> NAME/KEY: MOD_RES
<222> LOCATION: (2)..(2)
<223> OTHER INFORMATION: The Cys residue is substituted with a
        fluorinated bicyclic heteroaromatic group which is also bonded to
        the further Cys residue (6), thereby cyclising the peptide.
<220> FEATURE:
<221> NAME/KEY: MOD_RES
<222> LOCATION: (6)..(6)
<223> OTHER INFORMATION: The Cys residue is substituted with a
        fluorinated bicyclic heteroaromatic group which is also bonded to
        the further Cys residue (2), thereby cyclising the peptide.
<220> FEATURE:
<221> NAME/KEY: misc_feature
<222> LOCATION: (8)..(8)
<223> OTHER INFORMATION: CONH2 is bound to Leu residue (8).

<400> SEQUENCE: 61

Phe Cys Gly Gly Gly Cys Ala Leu
1               5

<210> SEQ ID NO 62
<211> LENGTH: 8
```

```
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: AcNH is bound to Phe residue (1)
<220> FEATURE:
<221> NAME/KEY: MOD_RES
<222> LOCATION: (2)..(2)
<223> OTHER INFORMATION: The Cys residue is substituted with a
      haloginated heteroaromatic group.
<220> FEATURE:
<221> NAME/KEY: MOD_RES
<222> LOCATION: (6)..(6)
<223> OTHER INFORMATION: The Cys residue is substituted with a
      haloginated heteroaromatic group.
<220> FEATURE:
<221> NAME/KEY: misc_feature
<222> LOCATION: (8)..(8)
<223> OTHER INFORMATION: CONH2 is bound to Leu residue (8).

<400> SEQUENCE: 62

Phe Cys Gly Gly Gly Cys Ala Leu
1               5

<210> SEQ ID NO 63
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: AcNH is bound to Phe residue (1)
<220> FEATURE:
<221> NAME/KEY: MOD_RES
<222> LOCATION: (2)..(2)
<223> OTHER INFORMATION: The Cys residue is substituted with a
      haloginated heteroaromatic group which is also bonded to the
      further Cys residue (6), thereby cyclising the peptide.
<220> FEATURE:
<221> NAME/KEY: MOD_RES
<222> LOCATION: (6)..(6)
<223> OTHER INFORMATION: The Cys residue is substituted with a
      haloginated heteroaromatic group which is also bonded to the
      further Cys residue (2), thereby cyclising the peptide.
<220> FEATURE:
<221> NAME/KEY: misc_feature
<222> LOCATION: (8)..(8)
<223> OTHER INFORMATION: CONH2 is bound to Leu residue (8).

<400> SEQUENCE: 63

Phe Cys Gly Gly Gly Cys Ala Leu
1               5

<210> SEQ ID NO 64
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: AcNH is bound to Phe residue (1)
<220> FEATURE:
<221> NAME/KEY: MOD_RES
<222> LOCATION: (2)..(2)
<223> OTHER INFORMATION: The Cys residue is substituted with a
      haloginated heteroaromatic group.
<220> FEATURE:
<221> NAME/KEY: MOD_RES
```

```
<222> LOCATION: (6)..(6)
<223> OTHER INFORMATION: The Cys residue is substituted with a
      haloginated heteroaromatic group.
<220> FEATURE:
<221> NAME/KEY: misc_feature
<222> LOCATION: (8)..(8)
<223> OTHER INFORMATION: CONH2 is bound to Leu residue (8).

<400> SEQUENCE: 64

Phe Cys Gly Gly Gly Cys Ala Leu
1               5

<210> SEQ ID NO 65
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: AcNH is bound to Phe residue (1)
<220> FEATURE:
<221> NAME/KEY: MOD_RES
<222> LOCATION: (2)..(2)
<223> OTHER INFORMATION: The Cys residue is substituted with a
      haloginated heteroaromatic group which is also bonded to the
      further Cys residue (6), thereby cyclising the peptide.
<220> FEATURE:
<221> NAME/KEY: MOD_RES
<222> LOCATION: (6)..(6)
<223> OTHER INFORMATION: The Cys residue is substituted with a
      haloginated heteroaromatic group which is also bonded to the
      further Cys residue (2), thereby cyclising the peptide.
<220> FEATURE:
<221> NAME/KEY: misc_feature
<222> LOCATION: (8)..(8)
<223> OTHER INFORMATION: CONH2 is bound to Leu residue (8).

<400> SEQUENCE: 65

Phe Cys Gly Gly Gly Cys Ala Leu
1               5

<210> SEQ ID NO 66
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: AcNH is bound to Phe residue (1)
<220> FEATURE:
<221> NAME/KEY: MOD_RES
<222> LOCATION: (2)..(2)
<223> OTHER INFORMATION: The Cys residue is substituted with a
      haloginated heteroaromatic group which is also bonded to the
      further Cys residue (6), thereby cyclising the peptide.
<220> FEATURE:
<221> NAME/KEY: MOD_RES
<222> LOCATION: (6)..(6)
<223> OTHER INFORMATION: The Cys residue is substituted with a
      haloginated heteroaromatic group which is also bonded to the
      further Cys residue (2), thereby cyclising the peptide.
<220> FEATURE:
<221> NAME/KEY: misc_feature
<222> LOCATION: (8)..(8)
<223> OTHER INFORMATION: CONH2 is bound to Leu residue (8).

<400> SEQUENCE: 66

Phe Cys Gly Gly Gly Cys Ala Leu
1               5
```

```
<210> SEQ ID NO 67
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: AcNH is bound to Phe residue (1)
<220> FEATURE:
<221> NAME/KEY: MOD_RES
<222> LOCATION: (2)..(2)
<223> OTHER INFORMATION: The Ser residue is substituted with a
      fluorinated heteroaromatic group.
<220> FEATURE:
<221> NAME/KEY: misc_feature
<222> LOCATION: (8)..(8)
<223> OTHER INFORMATION: CONH2 is bound to Leu residue (8).

<400> SEQUENCE: 67

Phe Ser Gly Gly Gly Ser Ala Leu
1               5

<210> SEQ ID NO 68
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: AcNH is bound to Phe residue (1)
<220> FEATURE:
<221> NAME/KEY: MOD_RES
<222> LOCATION: (2)..(2)
<223> OTHER INFORMATION: The Ser residue is substituted with a
      fluorinated heteroaromatic group.
<220> FEATURE:
<221> NAME/KEY: MOD_RES
<222> LOCATION: (6)..(6)
<223> OTHER INFORMATION: The Ser residue is substituted with a
      fluorinated heteroaromatic group.
<220> FEATURE:
<221> NAME/KEY: misc_feature
<222> LOCATION: (8)..(8)
<223> OTHER INFORMATION: CONH2 is bound to Leu residue (8).

<400> SEQUENCE: 68

Phe Ser Gly Gly Gly Ser Ala Leu
1               5

<210> SEQ ID NO 69
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: AcNH is bound to Phe residue (1)
<220> FEATURE:
<221> NAME/KEY: MOD_RES
<222> LOCATION: (2)..(2)
<223> OTHER INFORMATION: The Ser residue is substituted with a
      fluorinated heteroaromatic group which is also bonded to the
      further Ser residue (6), thereby cyclising the peptide.
<220> FEATURE:
<221> NAME/KEY: MOD_RES
<222> LOCATION: (6)..(6)
<223> OTHER INFORMATION: The Ser residue is substituted with a
      fluorinated heteroaromatic group which is also bonded to the
``` further Ser residue (2), thereby cyclising the peptide.
<220> FEATURE:
<221> NAME/KEY: misc_feature
<222> LOCATION: (8)..(8)
<223> OTHER INFORMATION: CONH2 is bound to Leu residue (8).

<400> SEQUENCE: 69

Phe Ser Gly Gly Gly Ser Ala Leu
1               5

<210> SEQ ID NO 70
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: AcNH is bound to Phe residue (1)
<220> FEATURE:
<221> NAME/KEY: MOD_RES
<222> LOCATION: (2)..(2)
<223> OTHER INFORMATION: The Ser residue is substituted with a
      fluorinated bicyclic heteroaromatic group.
<220> FEATURE:
<221> NAME/KEY: MOD_RES
<222> LOCATION: (6)..(6)
<223> OTHER INFORMATION: The Ser residue is substituted with a
      fluorinated bicyclic heteroaromatic group.
<220> FEATURE:
<221> NAME/KEY: misc_feature
<222> LOCATION: (8)..(8)
<223> OTHER INFORMATION: CONH2 is bound to Leu residue (8).

<400> SEQUENCE: 70

Phe Ser Gly Gly Gly Ser Ala Leu
1               5

<210> SEQ ID NO 71
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: AcNH is bound to Phe residue (1)
<220> FEATURE:
<221> NAME/KEY: MOD_RES
<222> LOCATION: (2)..(2)
<223> OTHER INFORMATION: The Ser residue is substituted with a
      fluorinated bicyclic heteroaromatic group which is also bonded to
      the further Ser residue (6), thereby cyclising the peptide.
<220> FEATURE:
<221> NAME/KEY: MOD_RES
<222> LOCATION: (6)..(6)
<223> OTHER INFORMATION: The Ser residue is substituted with a
      fluorinated bicyclic heteroaromatic group which is also bonded to
      the further Ser residue (2), thereby cyclising the peptide.
<220> FEATURE:
<221> NAME/KEY: misc_feature
<222> LOCATION: (8)..(8)
<223> OTHER INFORMATION: CONH2 is bound to Leu residue (8).

<400> SEQUENCE: 71

Phe Ser Gly Gly Gly Ser Ala Leu
1               5

<210> SEQ ID NO 72
<211> LENGTH: 8
<212> TYPE: PRT

```
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: AcNH is bound to Tyr residue (1)
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: CONH2 is bound to Leu residue (8).

<400> SEQUENCE: 72

Tyr Xaa Gly Gly Gly Xaa Ala Leu
1               5

<210> SEQ ID NO 73
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: AcNH is bound to Tyr residue (1)
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MOD_RES
<222> LOCATION: (2)..(2)
<223> OTHER INFORMATION: The Xaa residue is substituted with a
      fluorinated heteroaromatic group which is also bonded to the
      further Xaa residue (6), thereby cyclising the peptide.
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: MOD_RES
<222> LOCATION: (6)..(6)
<223> OTHER INFORMATION: The Xaa residue is substituted with a
      fluorinated heteroaromatic group which is also bonded to the
      further Xaa residue (2), thereby cyclising the peptide.
<220> FEATURE:
<221> NAME/KEY: misc_feature
<222> LOCATION: (8)..(8)
<223> OTHER INFORMATION: CONH2 is bound to Leu residue (8).

<400> SEQUENCE: 73

Tyr Xaa Gly Gly Gly Xaa Ala Leu
1               5

<210> SEQ ID NO 74
<211> LENGTH: 10
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
```

```
<222> LOCATION: (1)..(1)
<223> OTHER INFORMATION: AcNH is bound to Xaa residue (1)
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: CONH2 is bound to Leu residue (10).

<400> SEQUENCE: 74

Xaa Gly Ala Xaa Gly Gly Gly Xaa Ala Leu
1               5                   10

<210> SEQ ID NO 75
<211> LENGTH: 10
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (1)..(1)
<223> OTHER INFORMATION: AcNH is bound to Xaa residue (1)
<220> FEATURE:
<221> NAME/KEY: MOD_RES
<222> LOCATION: (1)..(1)
<223> OTHER INFORMATION: The Xaa residue is substituted with a
      fluorinated heteroaromatic group which is also bonded to the
      further Xaa residues (4) and (8), thereby cyclising the peptide.
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MOD_RES
<222> LOCATION: (4)..(4)
<223> OTHER INFORMATION: The Xaa residue is substituted with a
      fluorinated heteroaromatic group which is also bonded to the
      further Xaa residues (1) and (8), thereby cyclising the peptide.
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: MOD_RES
<222> LOCATION: (8)..(8)
<223> OTHER INFORMATION: The Xaa residue is substituted with a
      fluorinated heteroaromatic group which is also bonded to the
      further Xaa residues (1) and (4), thereby cyclising the peptide.
<220> FEATURE:
<221> NAME/KEY: misc_feature
<222> LOCATION: (10)..(10)
<223> OTHER INFORMATION: CONH2 is bound to Leu residue (10).

<400> SEQUENCE: 75

Xaa Gly Ala Xaa Gly Gly Gly Xaa Ala Leu
1               5                   10

<210> SEQ ID NO 76
<211> LENGTH: 8
<212> TYPE: PRT
<213> ORGANISM: Artificial Sequence
<220> FEATURE:
<223> OTHER INFORMATION: Synthetic sequence
<220> FEATURE:
```

```
<221> NAME/KEY: misc_feature
<222> LOCATION: (1)..(1)
<223> OTHER INFORMATION: AcNH is bound to Tyr residue (1)
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: CONH2 is bound to Leu residue (8).

<400> SEQUENCE: 76

Tyr Xaa Gly Gly Gly Xaa Ala Leu
1               5

<210> SEQ ID NO 77
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: AcNH is bound to Tyr residue (1)
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MOD_RES
<222> LOCATION: (2)..(2)
<223> OTHER INFORMATION: The Xaa residue is substituted with a
      fluorinated heteroaromatic group.
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: MOD_RES
<222> LOCATION: (6)..(6)
<223> OTHER INFORMATION: The Xaa residue is substituted with a
      fluorinated heteroaromatic group.
<220> FEATURE:
<221> NAME/KEY: misc_feature
<222> LOCATION: (8)..(8)
<223> OTHER INFORMATION: CONH2 is bound to Leu residue (8).

<400> SEQUENCE: 77

Tyr Xaa Gly Gly Gly Xaa Ala Leu
1               5

<210> SEQ ID NO 78
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: AcNH is bound to Tyr residue (1)
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
```

```
<220> FEATURE:
<221> NAME/KEY: misc_feature
<222> LOCATION: (8)..(8)
<223> OTHER INFORMATION: CONH2 is bound to Leu residue (8).

<400> SEQUENCE: 78

Tyr Xaa Gly Gly Gly Xaa Ala Leu
1               5

<210> SEQ ID NO 79
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: MOD_RES
<222> LOCATION: (1)..(1)
<223> OTHER INFORMATION: The Tyr residue is substituted with an R group
      which can be a H or a perfluoroheteroaromatic.
<220> FEATURE:
<221> NAME/KEY: Misc_feature
<222> LOCATION: (1)..(1)
<223> OTHER INFORMATION: AcNH is bound to Tyr residue (1)
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MOD_RES
<222> LOCATION: (2)..(2)
<223> OTHER INFORMATION: The Xaa residue is substituted with fluorinated
      heteroaromatic group which is also bonded to the further Xaa
      residue (6), thereby cyclising the peptide.
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: MOD_RES
<222> LOCATION: (6)..(6)
<223> OTHER INFORMATION: The Xaa residue is substituted with fluorinated
      heteroaromatic group which is also bonded to the further Xaa
      residue (2), thereby cyclising the peptide.
<220> FEATURE:
<221> NAME/KEY: Misc_feature
<222> LOCATION: (8)..(8)
<223> OTHER INFORMATION: CONH2 is bound to Leu residue (8).

<400> SEQUENCE: 79

Tyr Xaa Gly Gly Gly Xaa Ala Leu
1               5
```